(12) United States Patent
Shoshi et al.

(10) Patent No.: US 8,871,861 B2
(45) Date of Patent: Oct. 28, 2014

(54) SILICONE COMPOUND, PHOTOCURABLE LIQUID INK USING THE SILICONE COMPOUND, AND METHOD OF MANUFACTURING THE INK

(75) Inventors: Masayuki Shoshi, Kanagawa (JP); Soh Noguchi, Kanagawa (JP); Tetsurou Sasamoto, Kanagawa (JP); Takeshi Hihara, Kanagawa (JP); Tsuneo Kurotori, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 142 days.

(21) Appl. No.: 13/461,142

(22) Filed: May 1, 2012

(65) Prior Publication Data

US 2012/0283378 A1 Nov. 8, 2012

(30) Foreign Application Priority Data

May 2, 2011 (JP) .................................. 2011-102849
Jan. 16, 2012 (JP) .................................. 2012-006584
Mar. 27, 2012 (JP) .................................. 2012-072616

(51) Int. Cl.
| | |
|---|---|
| C09D 11/10 | (2014.01) |
| C09D 133/04 | (2006.01) |
| C09D 143/04 | (2006.01) |
| C07F 7/08 | (2006.01) |
| C07F 7/10 | (2006.01) |

(52) U.S. Cl.
CPC .............. C07F 7/0847 (2013.01); C07F 7/0852 (2013.01)
USPC ........... 524/588; 524/556; 556/437; 556/440; 548/406

(58) Field of Classification Search
None
See application file for complete search history.

(56) References Cited

U.S. PATENT DOCUMENTS

| | | | |
|---|---|---|---|
| 4,633,003 A | 12/1986 | Falcetta et al. | |
| 5,824,632 A * | 10/1998 | Flaningam et al. | 510/411 |
| 6,399,734 B1 | 6/2002 | Hodd et al. | |
| 6,439,708 B1 | 8/2002 | Kato et al. | |
| 8,431,655 B2 * | 4/2013 | Dershem | 525/533 |
| 2003/0088044 A1 | 5/2003 | Hodd et al. | |

(Continued)

FOREIGN PATENT DOCUMENTS

| | | |
|---|---|---|
| EP | 0455343 A1 | 11/1991 |
| JP | 6-236078 | 8/1994 |

(Continued)

OTHER PUBLICATIONS

STN Structure Search Results (Nov. 14, 2013).*

(Continued)

*Primary Examiner* — Vu A Nguyen
(74) *Attorney, Agent, or Firm* — Cooper & Dunham LLP

(57) ABSTRACT

A silicone compound represented by the following Chemical Structure 1:

Chemical Structure 1

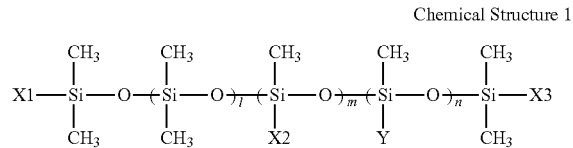

wherein Y represents a substituted or non-substituted alkyl group having one to ten carbon atoms, X1, X2, and X3 independently represent methyl groups or any of Substituents A-1 to A-7, and l, m, and n are independently zero or an integer of from 1 to 6.

7 Claims, 38 Drawing Sheets

(56) References Cited

U.S. PATENT DOCUMENTS

| | | | |
|---|---|---|---|
| 2005/0197505 A1* | 9/2005 | Molock et al. | 556/437 |
| 2009/0176926 A1* | 7/2009 | Hoogmartens | 524/543 |
| 2011/0060100 A1 | 3/2011 | Kimura et al. | |
| 2012/0086762 A1 | 4/2012 | Noguchi et al. | |
| 2012/0147103 A1 | 6/2012 | Hasegawa et al. | |
| 2012/0176456 A1 | 7/2012 | Maekawa et al. | |
| 2012/0242768 A1 | 9/2012 | Seno et al. | |

FOREIGN PATENT DOCUMENTS

| | | | | |
|---|---|---|---|---|
| JP | 2000-206738 | | 7/2000 | |
| JP | 2002-241647 | | 8/2002 | |
| JP | 2004035688 A | * | 2/2004 | C09J 153/02 |
| JP | 2008-24881 | | 2/2008 | |
| JP | 2010-148776 | | 7/2010 | |
| WO | WO00/06390 | | 2/2000 | |
| WO | WO00/22460 | | 4/2000 | |
| WO | WO 2007091867 A1 | * | 8/2007 | H01M 10/40 |
| WO | WO2011/049078 | | 4/2011 | |
| WO | WO2011/103176 | | 8/2011 | |

OTHER PUBLICATIONS

European search report dated Sep. 25, 2012 in corresponding European patent application No. 1266287.8.

Maudgal S et al: "Siloxane Containing Addition Polymides" Sampe Quarterly Engineers, Asuza, CA, vol. 15, No. 3, Jan. 1, 1984, pp. 24-30, XP009141788.

Choi K M et al: "A Photocurable Poly(dimethylsiloxane) Chemistry Designed for Soft Lithographic Molding and Printing in the Nanometer Regime", Journal of The American Chemical Society, ACS Publications, US, vol. Jan. 1, 2003 pp. 4060-4061, XP002323413.

Ohno, Tadayoshi, et al. (1981), "Electrostatic Pull Type Ink Jet Facsimile," The Journal of the Institute of Image Electronics Engineers of Japan, vol. 10 (No. 3), pp. 157-163.

Ichinose, Susumu, et al. (1983), "Solidstate Scanning Ink Jet Recording with Slit Type Head," IEICE Transations on Fundamentals of Electronics, Communications and Computer Sciences, vol. J66-C (No. 1), pp. 47-54.

* cited by examiner

SILICONE COMPOUND, PHOTOCURABLE LIQUID INK USING THE SILICONE COMPOUND, AND METHOD OF MANUFACTURING THE INK

CROSS-REFERENCE TO RELATED APPLICATION

This patent application is based on and claims priority pursuant to 35 U.S.C. §119 to Japanese Patent Applications Nos. 2011-102849, 2012-006584, and 2012-072616, filed on May 2, 2011, Jan. 16, 2012, and Mar. 27, 2012, respectively the entire disclosures of which are hereby incorporated by reference herein.

BACKGROUND OF THE INVENTION

1. Field of the Invention

The present invention relates to a silicone compound, photocurable liquid ink using the silicone compound, and a method of manufacturing the ink.

2. Description of the Background Art

Printers using blocks have generally been used to print images having a relatively long run length such as local advertisement, materials prepared for meeting, etc. in office, and large posters. In recent years, instead of such typical printers, on-demand printers that respond to diversified needs quickly and reduce the stock have begun to gain acceptance. Electrophotographic image forming apparatuses using dry toner and liquid toner and ink jet printers capable of producing quality images at high speeds have been expected as such on-demand printers.

On-demand printers are known to use solvent ink or solvent liquid toner containing pigments and organic solvents as the printers using blocks. However, in this technology, such organic solvents evaporate in an amount to an impermissible level when used to print images with a significant run length. This causes an atmosphere contamination problem by vaporized organic solvents. Therefore, it is necessary to provide a facility for waste of the organic solvents and/or a mechanism to retrieve the solvents.

In inkjet printers, the solvent ink can be used in a close system until the ink is discharged to a printed surface. Therefore, the atmosphere contamination problem is more or less relieved by taking a suitable measure for wasting.

However, different from the ink for use in printers using blocks, the ink for use in inkjet printers is required to have suitable fluidity for discharging ink. Therefore, with regard to the technology described above, it is necessary to increase the solvent density in the ink. The problem of atmosphere contamination ascribable to the organic solvents is inherently unsolved.

In addition, when solvent ink is used, the image quality is affected by the printing surface. For example, a permeable printing surface tends to blur but an impermeable printing surface makes it difficult to fix images. Furthermore, it takes some time before the ink layer formed on the printing surface becomes dried. Therefore, when a thick image is formed in a large printing surface, blurred images are easily produced due to the fluidity. That is, it is not easy to produce quality images with this technology.

The problem of atmosphere contamination ascribable to organic solvents for the inkjet printer still remains with regard to the liquid toner.

As a solution to this problem, using coloring particulates dispersed in a non-volatile liquid such as silicone oil is known. However, in such liquid toner, bonding of coloring resin particulates tends to be inhibited by the presence of non-volatile liquid when fixing images on a recording medium. Therefore, it is necessary to remove insulating liquid (carrier liquid) in the liquid toner using multiple removing rollers before image fixing, which complicates an image forming apparatus using the liquid toner. This is disadvantageous to demand for high speed performance.

As technologies to the problems described above, using a photosensitive ink and a printer system have begun to be appealing. This technology is to quickly optically-cure photosensitive ink discharged on printing surfaces. The photosensitive ink contains polymerizable monomers or oligomers, photopolymerization initiators, and pigments and is capable of producing images quickly by curing the ink by polymerization reaction upon application of light such as ultraviolet.

Furthermore, according to this technology, since the ink layer can be non-fluidized upon application of light, relatively high quality images can be produced. For example, as the liquid ink for use for inkjet, Japanese Patent Application Publication No. 2008-24881 (JP-2008-24881-A) describes curable compositions that contain ethylene-based unsaturated compounds such as (meth)acrylates and polystyrenes as ethylene-based unsaturated compounds having particular structures.

In addition, Japanese Patent No. 3985459 (JP-3985459-B) describes active energy line curable inkjet ink containing a compound having two or more acrylate bondings which contain two or more ethylene-based double bonding and 2-phenoxy ethylacrylate having one ethylene-based double bonding. However, although (meth)acrylates having a relatively low molecular weight for use in the ink satisfy the basic properties such as viscosity and optical curing speed, they have problems with regard to handling properties such as odor and skin sensitization. Having a good combination of the basic properties of optical curing and handling properties is difficult.

Furthermore, as the liquid ink for electrophotography, JP-3442406-B describes curable liquid vehicle having a particular viscosity range and a particular resistance range such as (meth)acrylic-modified silicones.

To be specific, the silicone portion is described to have an aliphatic or aromatic siloxane chain or ring having a particular dimethylsiloxane unit.

In addition, JP-4150118-B describes containing reactive silicone compounds in molecules. The reactive silicone compounds have functional groups such as isocyanates group, Si—H group, vinyl group, amino group, hydroxyl group, epoxy group, and methacylic group in molecules and in particular the silicone compounds having methacrylic groups are described in Examples.

However, since (meth)acrylic compounds for use in such ink have silicone portions in the molecules, the concentration of the reactive portion decreases (the number of collisions decreases) so that the optical curing speed is insufficient. Therefore, it is difficult to meet the demand about high speed performance

SUMMARY OF THE INVENTION

In view of the foregoing, the present invention provides silicone compound represented by the following Chemical Structure 1:

Chemical Structure 1

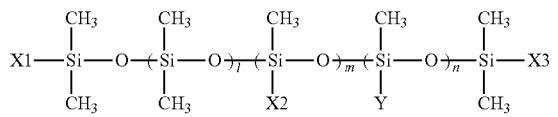

wherein Y represents a substituted or non-substituted alkyl group having one to ten carbon atoms, X1, X2, and X3 independently represent methyl groups or any of the following Substituents A-1 to A-7, at least one of X1, X2, and X3 is any of the Substituents A-1 to A-7, and l, m, and n are independently zero or an integer of from 1 to 6, Substituent A-1

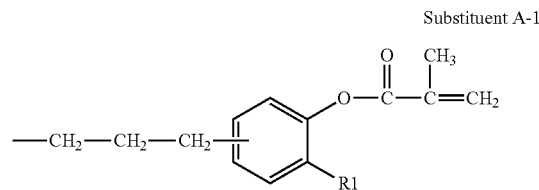

wherein R1 is a hydrogen atom, an alkyl group having one to four carbon atoms, or an alkoxy group having one to four carbon atoms, Substituent A-2

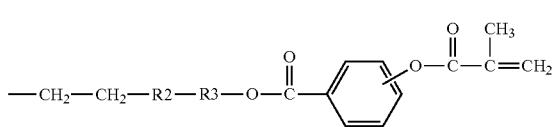

wherein R2 represents a single bonding or an alkylene group having one to four carbon atoms and R3 represents a single bonding or an alkyleneoxy group having one to four carbon atoms, Substituent A-3

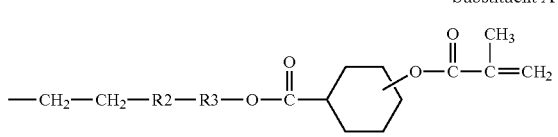

wherein R2 represents a single bonding or an alkylene group having one to four carbon atoms and R3 represents a single bonding or an alkyleneoxy group having one to four carbon atoms, Substituent A-4

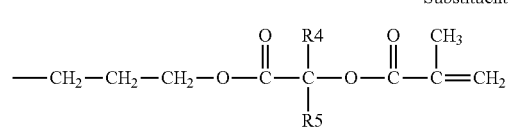

wherein R4 and R5 independently represent hydrogen atoms or methyl groups,

Substituent A-5

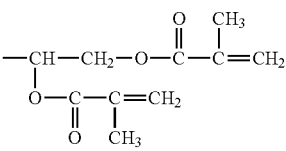

Substituent A-6

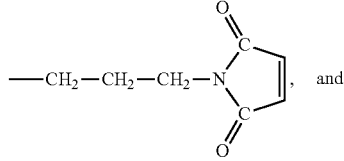

and

Substituent A-7

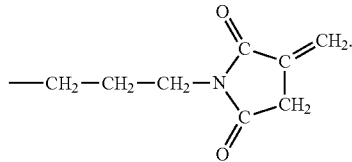

As another aspect of the present invention, a photocurable liquid ink is provided which includes a coloring agent, and a photocurable liquid including the silicone compound mentioned above.

As another aspect of the present invention, a method of manufacturing photocurable liquid ink is provided which includes dispersing a coloring resin particle having an acid group on the surface thereof in liquid that contains at least one of a silicone compound having an epoxy group and a long chain alkyl compound having an epoxy group to conduct reaction of the coloring resin particle and the at least one of a silicone compound having an epoxy group and a long chain alkyl compound having an epoxy group to chemically modify the coloring resin particle to obtain a liquid dispersion, and blending a photocurable liquid containing the silicone compound mentioned above with the liquid dispersion.

BRIEF DESCRIPTION OF THE SEVERAL VIEWS OF THE DRAWINGS

Various other objects, features and attendant advantages of the present invention will be more fully appreciated as the same becomes better understood from the detailed description when considered in connection with the accompanying drawings, in which like reference characters designate like corresponding parts throughout and wherein.

DETAILED DESCRIPTION OF THE INVENTION

Figure 1:
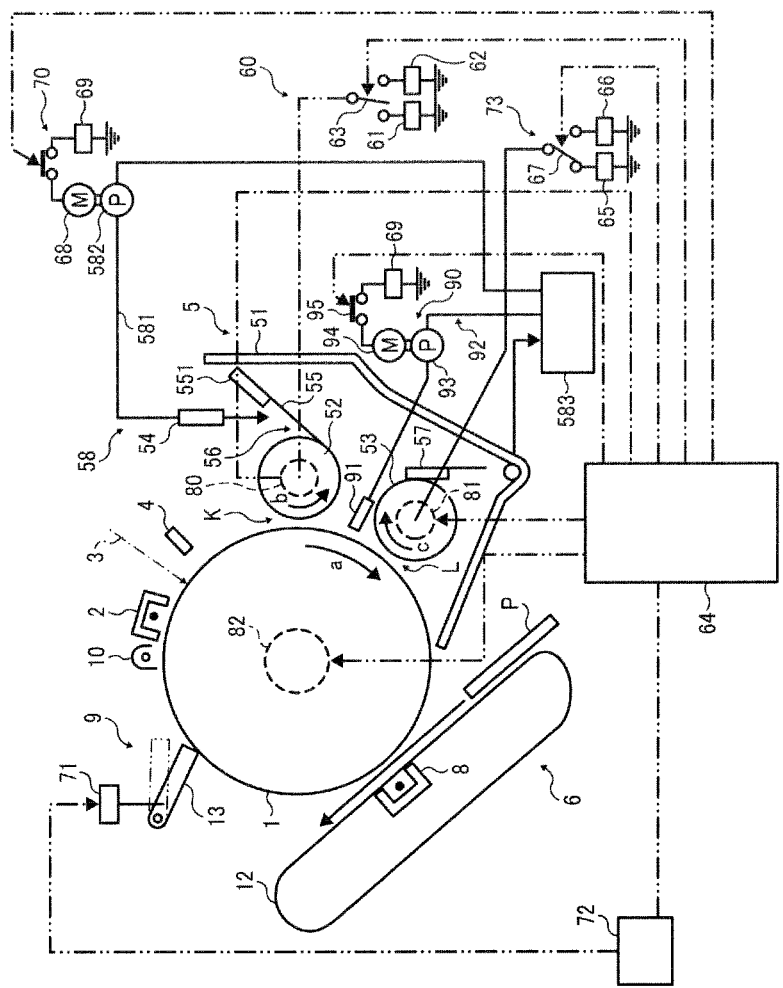
FIG. 1 is a schematic graph illustrating an example of an image forming apparatus employing electrophotography.

The present disclosure will be described below in detail with reference to several embodiments and accompanying drawings. The present inventors have investigated photocurable liquid ink that contains a coloring agent and photocurable liquid that contains a silicone compound 1 represented by the following Chemical structure 1.

This is because since the silicone compound 1 has a low viscosity so that the photocurable liquid can have a relatively high molecular weight, it is inferred that the ink is advantageous to reduce odor and skin sensitivity.

Silicone compound 1 represented by the following Chemical Structure 1:

Chemical Structure 1

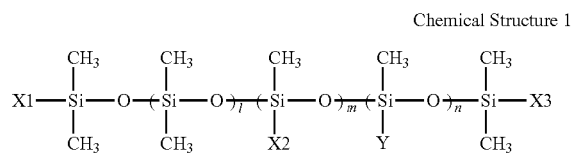

wherein Y represents a substituted or non-substituted alkyl group having one to ten carbon atoms, X1, X2, and X3 independently represent methyl groups or any of the following Substituents A-1 to A-7, at least one of X1, X2, and X3 is any of the Substituents A-1 to A-7, and l, m, and n are independently zero or an integer of from 1 to 6, Substituent A-1

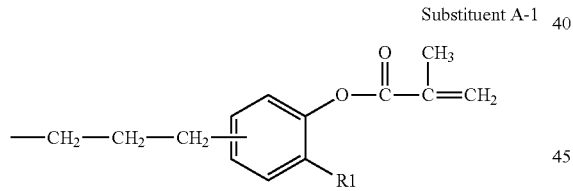

wherein R1 is a hydrogen atom, an alkyl group having one to four carbon atoms, or an alkoxy group having one to four carbon atoms, Substituent A-2

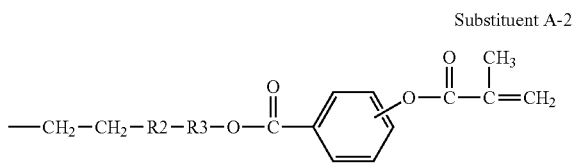

wherein R2 represents a single bonding or an alkylene group having one to four carbon atoms and R3 represents a single bonding or an alkyleneoxy group having one to four carbon atoms, Substituent A-3

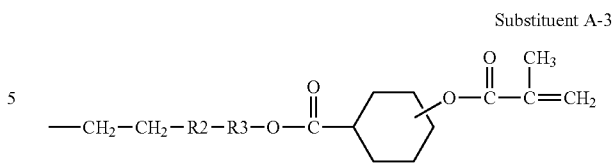

wherein R2 represents a single bonding or an alkylene group having one to four carbon atoms and R3 represents a single bonding or an alkyleneoxy group having one to four carbon atoms, Substituent A-4

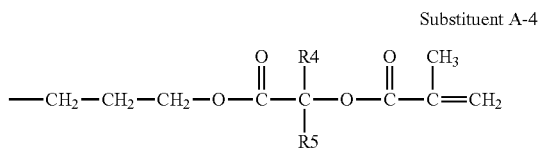

wherein R4 and R5 independently represent hydrogen atoms or methyl groups,

Substituent A-5

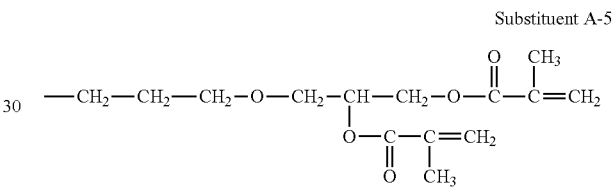

Substituent A-6

Substituent A-7

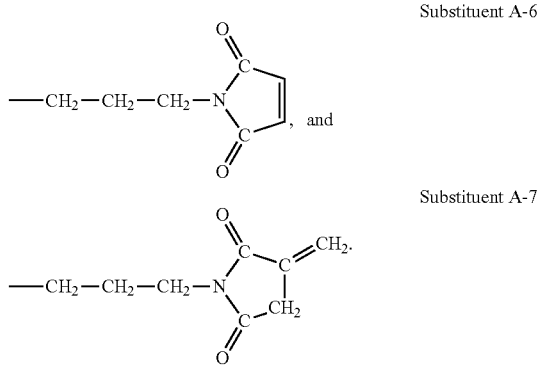

As a result, by irradiating the photocurable liquid ink that contains the photocurable liquid with light, the photocurable liquid is fixed on a recording medium with the coloring agent by polymerization reaction of the aromatic ester segments of the Substituents A-1 to A-7 to produce high definition images free from blurring and/or change in the color ascribable to the recording medium.

Furthermore, in the inkjet method, in comparison with typical natural drying, the performance of an image forming apparatus is improved and the strength of printed portions increases.

In addition, fusing toner by heat for fixing is obviated in electrophotography, thereby increasing the image forming speed of an image forming apparatus and reducing the energy consumption.

In spite that the photocurable liquid that contains the silicone compound 1 has a lower viscosity, less odor, and lower skin sensitization than typical compounds having functional groups such as (meth)acryloyloxy group in molecules, the photocurability of the photocurable liquid is excellent.

This mechanism is not clear but it is inferred that the silicone compound 1 causes weak repulsion against the mutual interaction between the silicone main chain and the aromatic ester segments and consequently "micro phase separation" is formed in the molecule or intermolecular of the silicone compound 1, thereby partially condensing the aromatic ester segment portion, which lead to achieving the excellent photocurability.

It is also inferred that the aromatic portion of the aromatic ester segment is deeply involved in this mutual interaction in this case.

In the silicone compound 1 for use in the present disclosure, the substituted or non-substituted alkyl group of Y having one to ten carbon atoms provides the reaction field for the Substituents A-1 to A-7 and is used to adjust the physical properties such as viscosity, resistance, and dielectric constant of the silicone compound 1.

Specific examples of the substituted or non-substituted alkyl group having one to ten carbon atoms include, but are not limited to, the alkyl compounds represented by the following Substituent D.

$$CH_2\text{—}CH_2\text{—}Z1 \hspace{2cm} \text{Substituent D}$$

In the Substituent D, Z1 represents an alkyl group having one to eight carbon atoms.

Specific examples of the alkyl group having one to eight carbon atoms of Z1 include, but are not limited to, methyl group, ethyl group, propyl group, butyl group, pentyl group, hexyl group, heptyl group, octyl group, and position isomers thereof.

Specific examples of substituents thereto include, but are not limited to, hydrocarbon groups such as cyclopentyl group, cyclohexyl group, and phenyl group; alkoxy groups such as methoxy group, ethoxy group, propioxy group, buthoxy group, penthyloxy group, hexyloxy group, heptyloxy group, octyloxy group, and position isomers thereof; alkoxy groups having an aromatic ring such as alkoxy group, phenyloxy group, benziloxy group, and phenthyloxy group; alkoxy groups via a low molecular weight alkylene group such as methylene group, ethylene group, and propylene group; and alkoxy group having an aromatic group via a low molecular weight alkylene group such as methylene group, ethylene group, and propylene group.

In addition, specific examples of the alkyl groups having a substituent of Y include, but are not limited to, siloxane compounds represented by the following substituent E.

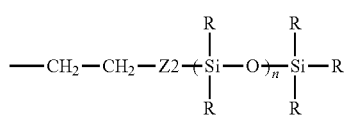

Substituent E

In the Substituent E, Z2 represents a single bonding or an alkylene group having one to four carbon atoms, R independently represents methyl group or phenyl group, and a symbol n represents 0 or an integer of from 1 to 10.

Specific examples of the alkylene group having one to four carbon atoms of Z2 include, but are not limited to, methylene group, ethylene group, trimethylene group, tetramethylene group, and position isomers thereof.

The silicone compound 1 can be manufactured by conducting hydrosilylation reaction between methyl hydrogen silicone compounds in which at least one of X1, X2, and X3 is a hydrogen atom and alkenyl compounds corresponding to the Substituents A-1 to A-7, the substituent D, and the substituent E. Use of the alkenyl compounds corresponding to the Substituents A-1 to A-7 is a requisite. To be specific, the alkenyl compounds of the substituent A-1 are represented by the following Alkenyl Compound for Substituent A-1.

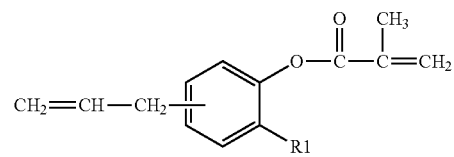

Alkenyl Compound for Substituent A-1

In the Alkenyl Compound for Substituent A-1, R1 represents a hydrogen atom, an alkyl group having one to four carbon atoms, and an alkoxy group having one to four carbon atoms.

The alkenyl compounds for the substituent A-1 can be manufactured by conducting known esterification reaction (condensation reaction) of A-1-1 (phenol body) and A-1-2 (carboxylic acid body) such as chemical reaction 1.

For example, a target alkenyl body of the substituent A-1 can be significantly quantitatively manufactured by adding diisopropyl carbodiimide (1.2 mol) as esterification catalyst in a toluen solution in which 1 mol of A-1-1 (phenol body), 1.2 mol of A-1-2 (carboxylic acid body), and 0.1 mol of catalyst of N,N-dimethylamino pyridine.

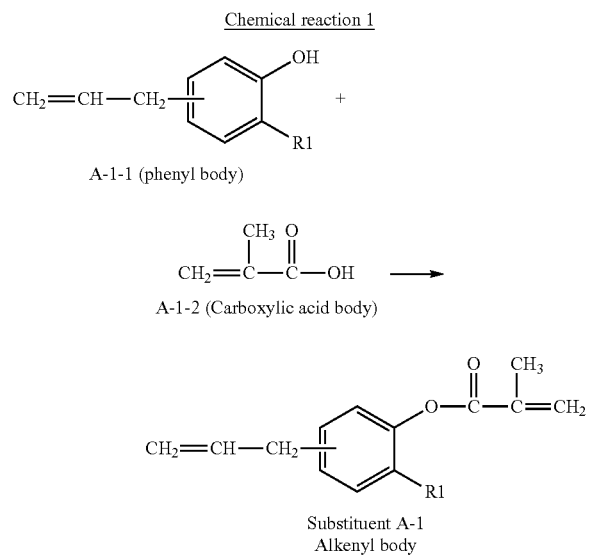

Chemical reaction 1

A-1-1 (phenyl body)

A-1-2 (Carboxylic acid body)

Substituent A-1
Alkenyl body

In the chemical reaction 1, R1 represents a hydrogen atom, an alkyl group having one to four carbon atoms, and an alkoxy group having one to four carbon atoms.

With regard to manufacturing an alkenyl body of the substituent A-1, A-1-1 (phenol body) can be easily manufactured by, for example, Claisen Rearrangement of A-1-5 (arylated phenol body) manufactured from the following A-1-3 (arylbromide) and A-1-4 (phenol compound) as in chemical reaction 2.

Chemical reaction 2

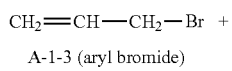
A-1-3 (aryl bromide)

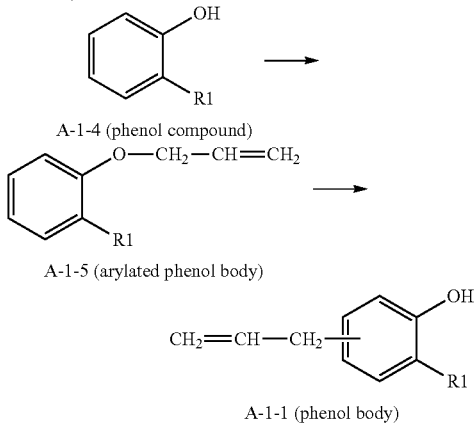

In the chemical reaction 2, R1 represents a hydrogen atom, an alkyl group having one to four carbon atoms, and an alkoxy group having one to four carbon atoms. In addition, among A-1-1 (phenol body), 2-arylphenol and 2-methoxy-4-arylphenol (eugenol) are available from the market and usable.

In addition, the alkenyl compound of the substituent A-2 is represented by the following:

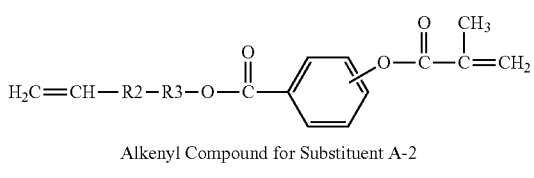

Alkenyl Compound for Substituent A-2

In the Alkenyl Compound for Substituent A-2, R2 represents a single bond and an alkylene group having one to four carbon atoms R3 represents a single bond and an alkyleneoxy group having one to four carbon atoms. Specific examples of the alkylene group having one to four carbon atoms of R2 and R3 include, but are not limited to, methylene group, ethylene group, propylene group, butylene group, and position isomers thereof The alkenyl compounds for the substituent A-2 can be manufactured by conducting known esterification reaction (condensation reaction) of A-2-1 (phenol body) and A-2-2 (carboxylic acid body) as in the chemical reaction 3.

For example, a target alkenyl body of the substituent A-2 can be significantly quantitatively manufactured by adding 1.2 mol of diisopropyl carbodiimide as an esterification catalyst in a toluen solution in which 1 mol of A-2-1 (phenol body), 1 mol of A-2-2 (carboxylic acid body), and 0.1 mol of catalyst of N,N-dimethylamino pyridine.

Chemical reaction 3

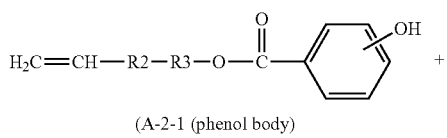
(A-2-1 (phenol body)

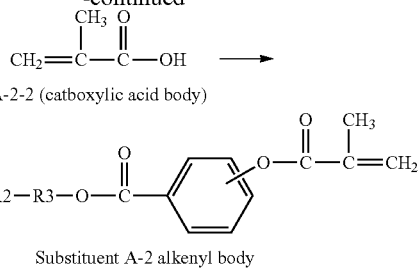
A-2-2 (catboxylic acid body)

Substituent A-2 alkenyl body

In the chemical reaction 3, R2 represents a single bonding and an alkylene group having one to four carbon atoms and R3 represents a single bond, and an alkyleneoxy group having one to four carbon atoms.

In addition, the alkenyl compound of the substituent A-3 is represented by the following:

Alkenyl Compound for Substituent A-3

In the Alkenyl Compound for Substituent A-3, R2 represents a single bonding and an alkylene group having one to four carbon atoms, R3 represents a single bonding and an alkyleneoxy group having one to four carbon atoms.

The alkenyl compounds for the substituent A-3 can be manufactured by conducting known esterification reaction (condensation reaction) of A-3-1 (phenol body) and A-3-2 (carboxylic acid body) as in the chemical reaction 4.

For example, a target alkenyl body of the substituent A-3 can be significantly quantitatively manufactured by adding 1.2 mol of diisopropyl carbodiimide as esterification catalyst in a toluen solution in which 1 mol of A-3-1 (phenol body), 1.2 mol of A-3-2 (carboxylic acid body), and 0.1 mol of catalyst of N,N-dimethylamino pyridine.

Chemical reaction 4

(A-3-1 (phenol body)

A-3-2 (carboxylic acid body)

Substituent A-3 (alkenyl body)

In the chemical reaction 4, R2 represents a single bonding and an alkylene group having one to four carbon atoms and R3 represents a single bonding and an alkyleneoxy group having one to four carbon atoms.

In addition, the alkenyl compound of the substituent A-4 is represented by the following:

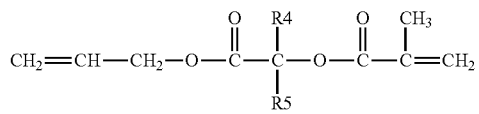

Alkenyl Compound for Substituent A-4

In the Alkenyl Compound for Substituent A-4, R4 and R5 independently represent hydrogen atoms or methyl groups.

The alkenyl compounds for the substituent A-4 can be manufactured by conducting known esterification reaction (condensation reaction) of A-4-1 (phenol body) and A-4-2 (carboxylic acid body) as in the following chemical reaction 5.

For example, a target alkenyl body of the substituent A-4 can be significantly quantitatively manufactured by adding 1.1 mol of diisopropyl carbodiimide as esterification catalyst in a toluen solution in which 1 mol of A-4-1 (alcohol body), 1.1 mol of A-4-2 (carboxylic acid body), and 0.1 mol of catalyst of N,N-dimethylamino pyridine.

Chemical reaction 5

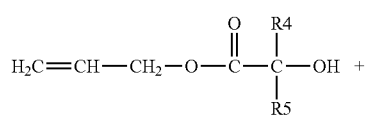

A-4-1 (alcohol body)

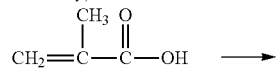

A-4-2 (carboxylic acid body)

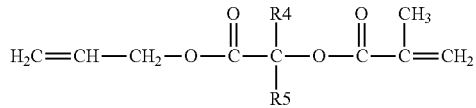

Substituent A-4 (alkenyl body)

In the chemical reaction 5, R4 and R5 independently represent hydrogen atoms and methyl groups.

In addition, the alkenyl compound of the substituent A-5 is represented by the following:

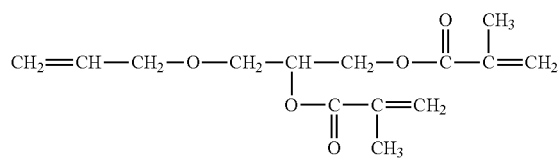

Alkenyl Compound for Substituent A-5

The alkenyl compounds for the substituent A-5 can be manufactured by conducting known esterification reaction (condensation reaction) of A-5-1 (alcohol body) and A-5-2 (carboxylic acid body) as in the following chemical reaction 6.

For example, a target alkenyl body of the substituent A-5 can be significantly quantitatively manufactured by adding diisopropyl carbodiimide (2.2 mol) as esterification catalyst in a toluen solution in which 1 mol of A-5-1 (alcohol body), 2.2 mol of A-5-2 (carboxylic acid body), and 0.2 mol of catalyst of N,N-dimethylamino pyridine.

Chemical reaction 6

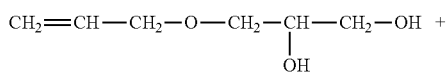

A-5-1 (alcohol body)

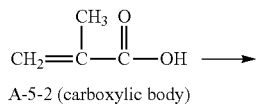

A-5-2 (carboxylic body)

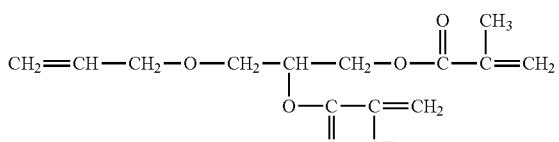

Substituent A-5 (alkenyl body)

In addition, the alkenyl compound of the substituent A-6 is represented by the following: Alkenyl Compound for Substituent A-6

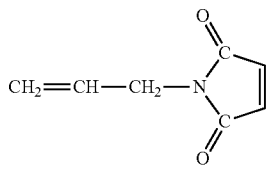

Alkenyl Compound for Substituent A-6

The alkenyl compound for substituent A-6 can be manufactured from A-6-1 (maleic anhydride) and A-6-2 (arylamine) according to J. Org. Chem. 62, 2652-2654 (1997) as in the following chemical reaction 7. For example, maleic acid arylamide acid is synthesized from 1.1 mol of A-6-1 (maleic anhydride) and 1 mol of A-6-2 (arylamine) and the resultant is dehydrated by hexamethylene disilazane (HMDS) under the presence of Lewis acid to obtain the target alkenyl compound for substituent A-6.

Chemical reaction 7

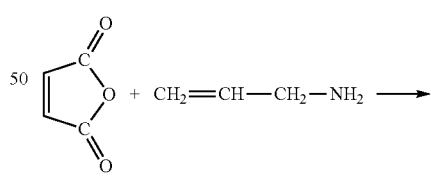

A-6-1          A-6-2

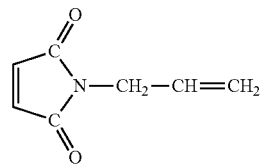

Alkenyl body of Substituent A-6

In addition, the Alkenyl compound of the substituent A-7 is represented by the following: Alkenyl Compound for Substituent A-7

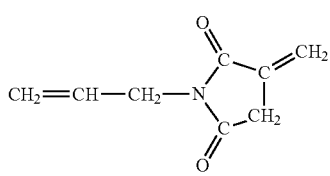

Alkenyl Compound for Substituent A-7

The alkenyl compounds for the substituent A-7 can be manufactured from A-7-1 (itaconic anhydride) and A-7-2 (arylamine) as in the following chemical reaction 8. For example, arylamide itaconate methyl ester is synthesized from 1.1 mol of A-7-1 (monomethyl itaconate) and 1 mol of A-7-2 (arylamine) followed by removing methanol by heating to manufacture the target alkenyl compounds for the substituent A-7.

Chemical reaction 8

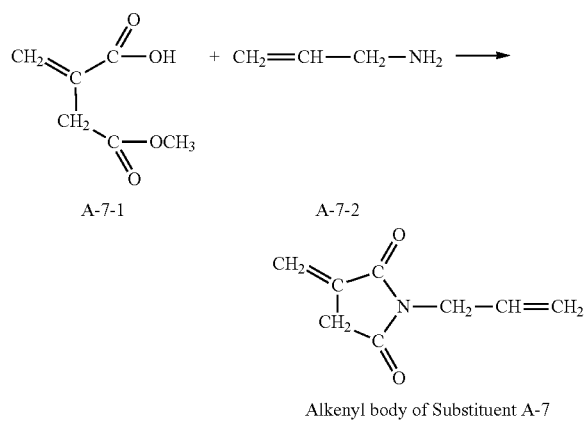

Alkenyl body of Substituent A-7

The alkenyl compound corresponding to the substituent D and the alkenyl compound corresponding to the substituent E are as follows:

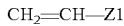  (Alkenyl Compound for Substituent D)

In the Alkenyl Compound for Substituent D, Z1 represents an alkyl group having one to eight carbon atoms.

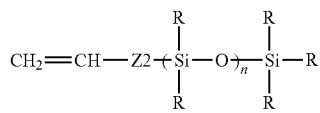

Alkenyl Compound for Substituent E

In Substituent E, Z2 represents a single bonding or an alkylene group having one to four carbon atoms, R independently represents methyl group or phenyl group, and a symbol n represents 0 or an integer of from 1 to 10.

Hydrosilylation reaction mentioned above is conducted preferably under the presence of a catalyst at room temperature or by heat with or without a solvent. For example, under the presence of a platinum catalyst, the silicone compound 1 is synthesized in a solvent at room temperature or by heating to 150° C. Furthermore, after the reaction, it is preferable to remove products having a low molecular weight and non-reacted materials with a reduced pressure. Furthermore, it is preferable to refine the resultant by distillation.

Specific examples of the platinum catalyst include, but are not limited to, simple platinum, mixtures in which platinum is borne on alumina, silica, carbon black, etc, chloroplatinic acid, platinum-olefin complexes, platinum-vinyl siloxane complexes, platinum-phosphite complexes, dicarbonyl dichloro platinum, and Karstedt catalysts.

Among these, chloroplatinic acid, platinum-olefin complexes, and platinum-vinylsiloxane complexes are preferable in terms of catalyst activity.

In addition, these catalysts can be used alone or in combination. In addition, there is no specific limit to the amount of use of the catalyst. Preferably, the platinum catalyst is used in an amount of from 10-1 to 10-band preferably from 10-3 to 10-6 based on 1 mol of an alkenyl group. When the amount of catalyst is too small, hydrosilylation reaction may not sufficiently proceed.

In addition, an amount of catalyst that is too large tends to cause problems such as increase in cost, coloring or reduction of transparency of target products by mingling of catalyst residual. Specific examples of the solvents for use in hydrosilylation reaction include, but are not limited to, hydrocarbons, halogenized hydrocarbons, ethers, and esters. It is preferable to use heptane, hexane, benzene, toluene, xylene, etc.

Methylhydrogen silicone compounds for use in manufacturing the silicone compound 1 are available from the market.

For example, specific examples thereof having both-terminal type include, but are not limited to, 423785 (average molecular weight: up to 580, available from Aldrich), 482064 (average molecular weight: up to 17,500, available from Aldrich), DMS-H-03 (molecular weight: 400 to 500, available from Gelest), and DMS-H-11 (molecular weight: 1,000 to 1,100, available from Gelest).

Specific examples of the silicone compound 1 having a branch-chain type include, but are not limited to, 482196 (average molecular weight: up to 950, available from Aldrich), 482374 (average molecular weight: up to 13,000, available from Aldrich), HMS-501 (molecular weight: 900 to 1,200, available from Gelest), HMS-031 (molecular weight: 1,900 to 2,000, available from Gelest), HMS-071 (molecular weight: 1,900 to 2,000, available from Gelest), HMS-151 (molecular weight: 1,900 to 2,000, available from Gelest), HMS-991 (molecular weight: 1,400 to 1,800, available from Gelest), SH-1107 (Viscosity: 20 mm$^2$/s, available from Dow Corning Toray), KF-99 Viscosity: 20 mm$^2$/s, available from Shin-Etsu Chemicals Co., Ltd.), and KF-9901 Viscosity: 20 mm$^2$/s, available from Shin-Etsu Chemicals Co., Ltd.).

Furthermore, hydrosilylation reaction can be conducted under the presence of an antioxidant. As the antioxidant, it is suitable to use phenol-based anti-oxidants having the feature of radical chain inhibitors such as 2,6-di-tert-butyl-p-cresol and 2,6-di-tert-butylphenol. Also, amine-based antioxidants can be similarly used as the radical chain inhibitors. Specific examples thereof include, but are not limited to, N-phenyl-β-nephtyl amine, N,N'-di-sec-butyl-p-phenylene diamine, and phenothiazine.

In addition, among the silicone compound 1, the following silicone compounds 2 to 6 represented by the following Chemical structures 2 to 6, respectively, are preferable.

Silicone compound 2

(Chemical Structure 2)

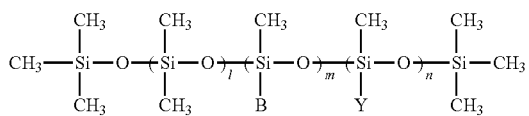

wherein Y represents a substituted or non-substituted alkyl group having one to ten carbon atoms, B represents any of the following Substituents B-1 to B-3, and l, m, and n are independently zero or an integer of from 1 to 6, wherein Y represents a substituted or non-substituted alkyl group having one to ten carbon atoms, C' represents the following Substituent C, and l, m, and n independently represent zero or an integer of from 1 to 6,

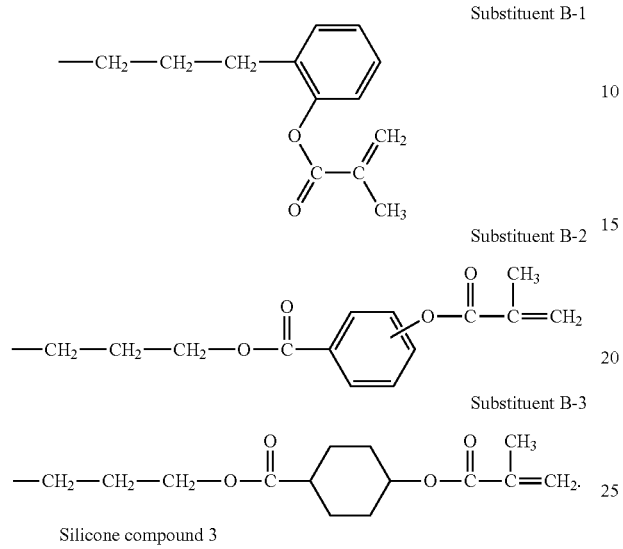

Silicone compound 3

(Chemical Structure 3)

wherein B represents any of the following Substituents B-1 to B-3 and l is zero or an integer of from 1 to 6,

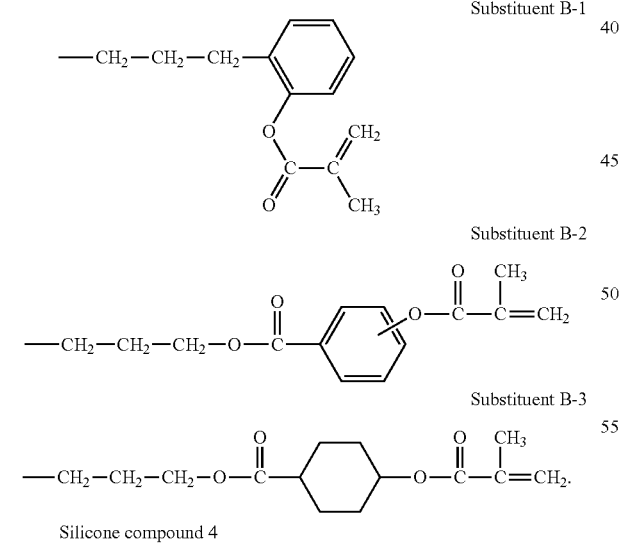

Silicone compound 4

(Chemical Structure 4)

wherein C' represents the following Substituent C and l presents zero or an integer of from 1 to 6, wherein Y represents a substituted or non-substituted alkyl group having one to ten carbon atoms, A represents any of the following Substituents A-4 to A-7, and l, m, and n are independently zero or an integer of from 1 to 6,

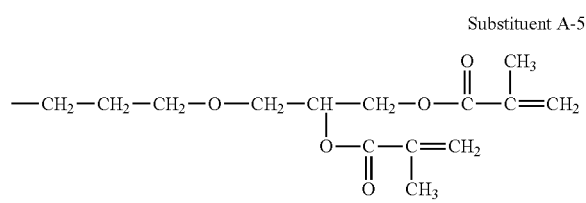

wherein R4 and R5 independently represent hydrogen atoms or methyl groups,

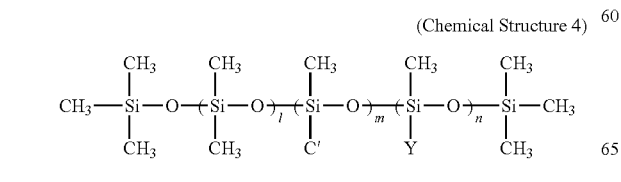

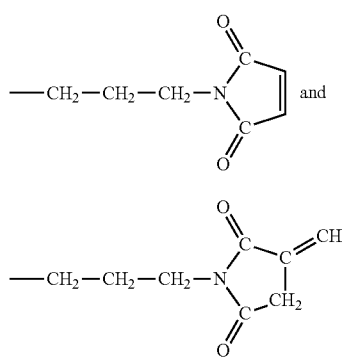

Substituent A-6 and Substituent A-7

Next, the coloring agents contained in the photocurable liquid ink of the present disclosure are described. The coloring agent is dispersed in a photocurable liquid using a dispersant and dispersion stabilizer. There is no specific limit to the dispersing device for use in dispersion treatment of the coloring agent. Preferred specific examples thereof include, but are not limited to, ultrasonic dispersing devices, pressure dispersing devices such as mechanical homogenizers and pressure-type homogenizers, and medium-type dispersing devices such as sand grinders, diamond fine mills, and bead mills.

However, it is preferable to form coloring resin particles using a resin optionally followed by dispersion in a photocurable liquid using a dispersant and a dispersion stabilizer in terms of the uniformity of the photocurable liquid ink. The coloring resin particles optionally contain additives such as charge control agents and waxes and can be manufactured by suitably selected known methods according to the resin components and desired particle diameters or forms. For example, specific examples of such manufacturing methods include, but are not limited to, wet manufacturing methods such as suspension polymerization methods, emulsification polymerization methods, dispersion polymerization methods, emulsification dispersion granulation methods, coacervation methods, and seed polymerization methods and dry manufacturing methods such as pulverization methods and spray drying methods. The wet manufacturing methods are preferable in terms of the yield of uniform spherical coloring resin particles.

Furthermore, to manufacture coloring resin particles having an acid group on the surface, the wet manufacturing method that uses an aqueous medium as a continuous phase is advantageous in terms that acid groups serving as polar groups are specifically formed on the surface of the particles in the formation of the coloring resin particles. Also, it is preferable (to self-dispersion type) because the acid group formed on the surface significantly contributes to dispersion stabilization of the formed coloring resin particles. Furthermore, among the wet manufacturing methods, it is preferable to use coloring resin particles obtained by the emulsification granulation method and the coacervation method in light of the variety of resins available, easiness of adjusting of the molecular weight and the sharpness of the particle diameter distribution.

The emulsification dispersion granulation method and the coacervation method are known granulation methods based on the difference in the solubility of the resins. For example, in the emulsification dispersion granulation method, a resin solution in which resins are dissolved in a non-aqueous organic solvent is emulsified and dissolved in an aqueous continuous phase to form O/W type emulsion and thereafter the organic solvent is removed from the O/W type emulsion to precipitate resin particles.

In addition, in the coacervation method, resins are dissolved in an aqueous solvent and the resin solution is dripped to a poor solvent (aqueous continuous phase) while stirring. In this case, in the resin or the liquid dispersion that contains the resin, optional additives such as dispersants, thermal stabilizers, anti-oxidants, and ultraviolet absorbents in addition to the coloring agents are uniformly dissolved and dispersed. By using these, the processes are simplified so that the resin particles are obtained by relatively simple operations. Therefore, the production efficiency can be improved and the cost is reduced.

There is a salting-out method, which is similar to the emulsification dispersion granulation method and the coacervation method and also a furthermore devised granulation method based on the difference of the solubility of the resins used. In the salting-out method, the coloring agent is dispersed at a particular temperature in a solvent in which resins having an acid group are neutralized in order to be soluble in an aqueous medium. This liquid dispersion is stably dispersed in the aqueous medium by function of an electric double layer in which the coloring agent is taken in by a salt of the acid group. Next, in this liquid dispersion, by an addition of electrolytes to destroy or reduce the electric double layer, the neutralized resin is disstabilized and precipitates on the coloring agent to form the coloring resin particles.

In the salting-out method, since the resins precipitate from a uniform resin solution, extremely uniform coloring resin particles are obtained. Furthermore, this method is simple and minimizes the amount of the dispersant or dispersion stabilizer or dispenses therewith, thereby reducing the amount of the dispersant or dispersion stabilizer attached to the coloring particles.

Next, the neutralized resin by the acid is returned to the acid form (fixing), segregated by filtering, etc., washed with water, etc. followed by drying to manufacture coloring resin particles having an acid group on the surface.

The salting-out is conducted at the glass transition temperature (Tg) or lower. [Tg–50° C.] or lower is preferable. In the range of Tg to 50° C. lower than Tg, aggregation tends to occur during granulation although depending on the salting-out conditions.

To neutralize the resin having an acid value, it is suitable to use base compounds such as sodium hydroxide, potassium hydroxide, sodium carbonate, potassium carbonate, and ammonium.

Specific examples of the electolytes include, but are not limited to, acidic materials such as hydrochloric acid, sulfuric acid, phosphoric acid, acetic acid, and oxalic acid and organic or inorganic aqueous salts such as sodium sulfate, ammonium sulfate, potassium sulfate, magnesium sulfate, sodium phosphorate, sodium chloride, potassium chloride, and sodium acetate. These electrolytes are used alone or in combination. Among these, it is preferable to use a monovalent cationic sulfate such as sodium sulfate, ammonium sulfate, and potassium sulfate in terms of uniform salting-out. Although these electrolytes can be added as powder while stirring, an aqueous solution of the electrolytes is preferably dripped while stirring to secure the uniformity furthermore. In this case, in the resin or the resin solution, optional additives such as dispersants, thermal stabilizers, antioxidants, and ultraviolet absorbents are uniformly dissolved and dispersed.

The particle diameter distribution of the coloring resin particulates is reflected in the particle diameter distribution of the coloring resin particles the surface of which is modified in the photocurable liquid ink to be manufactured. Therefore, the coloring resin particles having a high mono-dispersion property are preferable. The relative standard deviation (CV) thereof having 50% or lower is preferable.

When the relative standard deviation is too high, the particle diameter distribution of the coloring resin particles the surface of which is modified in the photocurable liquid ink tends to be broad, thereby significantly degrading the characteristics of the particles due to non-uniformityl of the particle diameter. For example, the dispersion property and the dispersion stability of the photocurable liquid ink tends to deteriorate.

The relative standard deviation is calculated by the following relationship: Relative standard deviation (CV value (%)= (sd/m)×100, where sd represent the standard deviation of the particle diameter and m represents the average particle diameter. sd and m are obtained by a particle diameter analyzer (FPAR-1000, manufactured by Otsuka Electronics Co., Ltd.) using Dynamic Light Scattering method.

Specific examples of the resins include, but are not limited to, synthetic resins such as acrylic resins, styrene resins, epoxy resins, urethane resins, vinyl resins, phenol resins, polyeste resins, polyamide resins, and melamine resins, natural resins such as gelatin, cazein, and cellulose starch, and copolymer resins thereof. Any resins to which carbozyl group and sulfone group as an acid group or salts thereof are introduced can be suitably used.

In addition, these resins may form a cross-linking structure according to the purpose of use. It is preferable to blend the resin having the acid group such that the acid value ranges from 10 to 300 (mgKOH/g). When the acid value is too low, the solubility of the resin in an aqueous medium tends to deteriorate, resulting in deterioration of the uniformity of the particles, which may increase the relative standard deviation greater than 50%. In addition, when the acid value is too high, the characteristics are hardly improved while just increasing the cost for neutralization. In the range of the acid value of from 10 to 300 (mgKOH/g), the dispersion stability during the particle manufacturing is improved, the amount of use of the dispersant or the dispersion stabilizer is reduced (self-dispersion type), consequently particles having a good mono-dispersion property can be manufactured, and the number of washing decreases, which is advantageous in terms of the operation and environment. Therefore, the monomer having the acid value is further preferably blended such that the acid value ranges from 10 to 300.

The aqueous medium represents an aqueous solution of hydrophilic organic solvent. The hydrophilic organic solvent means an organic solvent having a solubility of 2% by weight or greater in water at 20° C. Specific examples of the hydrophilic organic solvents include, but are not limited to, alcohols such as methyl alcohol, ethyl alcohol, modified ethyl alcohol, isopropyl alcohol, n-butyl alcohol, isobutyl alcohol, tert-butyl alcohol, sec-butyl alcohol, tert-amyl alcohol, 3-pentanol, benzil alcohol, cyclohexanol, ethylene glycol, glycerin, and diethylene glycol; ether alcohols such as methyl cellosolve, ethyl cellosolve, isopropyl cellosolve, butyl cellosolve, diethylene glycol monomethyl ether, and diethylene glycol monoethyl ether; ethers such as tetrahydrofuran, ethylene glycol dimethyl ether, and dioxane, and organic solvents that contain nitrogen atoms such as pyridine and dimethyl formamide.

These can be used alone or in combination. Among these, lower alcohols such as methyl alcohol, ethyl alcohol, and isopropyl alcohol are preferable.

It is possible to control the dispersion stability of the resin solution by a liquid mixture of the hydrophillic organic solvent and water. The content ratio of the hydrophillic organic solvent to the aqueous medium when prescribing the aqueous medium is preferably 50% by weight or lower. When the ratio of the hydrophillic organic solvent is too high, the coloring resin particles tend to agglomerate so that the particle diameter and the particle size distribution is uncontrollable.

In such a case, the particle diameter and the particle size distribution are controlled by the precipitation speed of the neutralized resin during salting-out. That is, when the precipitation speed is fast, coloring resin particles having a small particle diameter tend to be formed. When the precipitation speed is slow, coloring resin particles having a great particle diameter tend to be formed. In particular, to manufacture coloring resin particles having a relatively large particle diameter, low stirring speed and low electrolyte addition speed are required, which increases the possibility of agglomeration of the coloring resin particles. Therefore, supplement treatment such as a liquid mixture (aqueous medium) of the hydrophillic organic solvent and water or additives such as dispersion stabilizer may be necessary.

The coloring resin particles having an acid group are preferably manufactured by salting-out to have an average particle diameter of from 0.01 μm to 5 μm.

The acid value (mgKOH/g) of the manufactured coloring resin particles preferably ranges from 3 to 200. When the acid value is too small, the reaction tends to be limited in the chemical modification by a silicone compound having an epoxy group and/or long chain alkyl compound having an epoxy group in the next process, thereby limiting demonstration of the features of the silicone group and/or the long chain alkyl group on the surface of the coloring resin particles.

Therefore, good dispersion property and dispersion stability are not obtained. When the acid value is too large, the characteristics are hardly ameliorated. This is inferred to be that the feature of the silicone group and/or the long chain alkyl group on the surface of the coloring resin particle is almost saturated.

Next, the additives for use in manufacturing the coloring resin particle having an acid group are described. To manufacture the coloring resin particle having an acid group, a surface active agent can be optionally added. The blending amount of the surface active agent preferably ranges from 0.1 parts by weight to 5 parts by weight based on 100 parts of the total amount of monomer. There is no specific limit to the selection of the surface active agent. Preferred specific examples thereof include, but are not limited to, the following ionic or non-ionic surface active agent.

Specific examples of the ionic surface active agent include, but are not limited to, sulfonates such as dodecyl benzene sodium sulfonate, aryl alkyl polyether sodium sulfonate, 3,3-disulphone diphenyl urinate, and 4,4-diazobis-amino-8-naphthol-6-sodium sulfonate; esters of sulfuric acid such as dodecyl sodium sulfonate, tetradecyl sodium sulfonate, pentadecyl sodium sulfonate, and dialkyl sulfosuccinic acid ester sodium; and aliphatic acid salts such as sodium oleate, sodium laurate, sodium caprate, sodium caproate, and potassium stearate. Specific examples of the non-ionic surface active agent include, but are not limited to, polyethylene oxide, polypropylene oxide, a combination thereof, high aliphatic acid esters of polyethylene glycol, high aliphatic acid esters of polyproyene oxide, alkylphenol polyethlene oxide, alkylphenol polypropylene oxide, polyethylene oxide alkyl ether, polypropylene oxide alkyl ether glycol, and sorbitan ester.

Furthermore, dispersion stabilizers can be added. Specific examples of the dispersion stabilizers include, but are not limited to, dispersion stabilizer polymers such as sodium salts of partially-saponified polyvinyl alcohol, poly(meth)acrylic acid, polystyrenepoly(meth)acrylic acid copolymer, ester copolymers of poly(meth)acrylic acid-poly(meth)acrylic acid, polyvinyl pyrolidone, polyvinylether, gelatin, methyl cellulose, ethylcellulose, hydroxyethyl cellulose, carboxymethyl cellulose and inorganic dispersion stabilizers such as calcium phosphate, magnesium phosphate, aluminum phosphate, calcium carbonate, magnesium carbonate, barium sulfate, magnesium hydroxide, and bentonite.

Any known pigments and dyes can be used as the coloring agent. There is no specific limit to the selection of organic pigments. Specific examples thereof include, but are not limited to, aniline blue, charcoal blue, chrome yellow, chrome yellow, ultramarine blue, Dupon oil red, quinoline yellow, methylene blue chloride, copper phthalocyanine, Malachite Green oxalate, Lamp black, Rose Bengal, C.I. Pigment Red 48:1, C.I. Pigment Red 122, C.I. Pigment Red 57:1, C.I. Pigment Red 184, C.I. Pigment Yellow 97, C.I. Pigment Yellow 12, C.I. Pigment Yellow 17, C.I. Solvent Yellow 162, C.I. Pigment Yellow 180, C.I. Pigment Yellow 185, C.I. Pigment Blue 15:1, and C.I. Pigment Blue 15:3.

There is no specific limit to the selection of inorganic pigments. Specific examples thereof include, but are not limited to, carbon black, titanium oxide, colcothar, ferrite, and magnetite. These can be used alone or in combination.

In addition, so-called processed coloring agent (coloring resin particle) which are preliminarily covered with a resin can be used. To be specific, it is suitable to use the processed coloring agent available from the market such as so-called Color Chip manufactured by mixing and kneading a coloring agent and a resin by a two-roll by heating (manufactured by Taihei Chemical Industrial Co., Ltd., Taisei Kako CO., LTD., etc.) and Microlith (manufactured by Ciba Specialty Chemicals).

The content of the coloring agent is from 10% by weight to 80% by weight and preferably from 30% by weight to 60% by weight based on the coloring resin particles (including coloring resin particle having an acid group on the surface). In addition, there is no specific limit to the Tg of the coloring resin particles (including coloring resin particle having an acid group on the surface). Tg is preferably from 50° C. to 120° C. There is not specific limit to the molecular weight of the coloring resin particles. Preferably, the weight average molecular weight thereof is from 2,000 to 50,000.

The surface-treated coloring resin particles are described next. The surface-treated coloring resin particles are obtained by chemically modifying the coloring resin particle having an acid group on the surface described above with at least one kind of the silicone compound having an epoxy group and/or the long chain alkyl compound having an epoxy group. Chemical modification is mainly due to the chemical reaction between the acid group on the surface of the coloring resin particles and epoxy group. The coloring resin particles are covered with the silicone group and/or the long-chain alkyl group by directly bonding the silicone group and/or the long-chain alkyl group with the surface of the coloring resin particles via the ester group. Without agglomeration and fusion between the coloring resin particles, the obtained coloring resin particles have good (re-)dispersion property and the dispersion stability over an extended period of time.

In general, the chemical modification is conducted by treating the coloring resin particle having an acid group on the surface and the silicone compound having an epoxy group and/or the long chain alkyl compound having an epoxy group in an organic solvent. There is no specific limit to the organic solvent as long as it dissolves all or some of the silicone compound having an epoxy group and/or the long chain alkyl compound having an epoxy group without dissolving the coloring resin particle having an acid group. Reaction inert organic solvents such as hydrocarbon solvent or silicone oil are suitable.

The silicone compound having an epoxy group has, for example, a molecular structure represented by the following chemical formula 1.

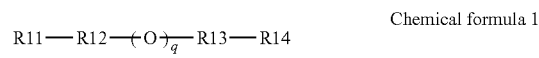

Chemical formula 1

In the chemical formula 1, R11 represents epoxy group, a group having an epoxy group such as epoxy cyclohexane group, q represents 0 or 1, R12 and R13 independently a single bonding or alkylene group having one to four carbon atoms such as methylene group, ethylene group, trimethylene group, tetramethylene group, and position isomers thereof, R14 has a dimethylpolysiloxane skeleton preferably with a lower alkyl group having one to six carbon atoms at the terminal substituent and the number of dimethyl siloxane units (polymerizatoin degree) is preferably from 1 to 50 and more preferably from 1 to 16.

Such a silicone compound having an epoxy group is available from the market. Preferred specific examples thereof include, but are not limited to, epoxy-modified silicones having a low molecular weight such as (3-glycidoxy propyl)bis (trimethylsiloxy)methyl silane (manufactured by Tokyo Chemical Industry Co., Ltd.), (3-glycidoxy propyl) pentamethyldisiloxane (manufactured by AZmax. Co) and epoxy-modified silicones having a high molecular weight such as MCR-E11 (manufactured by AZmax. Co), MCR-E21 (manufactured by AZmax. Co), X-22-173DX (manufactured by Shin-Etsu Chemicals Co. Ltd.), FZ-3720 (manufactured by Dow Corning Toray), BY16-839 (manufactured by Dow Corning Toray), and SF8411 (manufactured by Dow Corning Toray).

In addition, preferred specific examples of the long-chain alkyl compounds having an epoxy group include, but are not limited to, 1,2-epoxyhexane, 1,2-epoxyheptane, 1,2-epoxy octane, 1,2-epoxy decane, 1,2-epoxy dodecane, 1,2-epoxy tetradecane, 1,2-epoxy hexadecane, 1,2-epoxy octadecane, 1,2-epoxy eicosan, alkyl glycidyl ethers such as butylglycidyl ether, 2-ethylhexyl glycidyl ether, and benzil glycidyl ether, and long-chain alkyl carboxylic acid ester compounds such as butylic acid glycidyl ester, and stearic acid glycidyl ester, and neodecane acid glycidyl ester.

In manufacturing of the surface treated coloring resin particles, basically, the acid group on the surface of the coloring resin particles and the epoxy group in the silicone compound having an epoxy group and/or the long chain alkyl compound having an epoxy group collide in an organic solvent to conduct esterification of the acid group. In the initial reaction state, the coloring resin particles having an acid group on the surface agglomerate and as the reaction proceeds, the compatibility with the organic solvent increases. As a result, in the last stage of the reaction, most of the agglomerated particles are considered to change into the primary particle dispersion state.

Therefore, the surface treatment is preferably conducted while stirring. It is suitable to use a stirrer such as a three one motor to a degree that the entire liquid mixes and flows. As a stirring wing, a flat turbine wing, a propeller wing, an anchor wing can be used. Furthermore, pressure dispersion machine such as an ultrasonic dispersion device, a mechanical homogenizer, and a pressure homogenizer and medium type dispersion machine such as sand grinder, diamond fine mill, and bead mill can be used. Among these, ultrasonic dispersion machines are suitable in terms of dispersion efficiency. Furthermore, the surface treatment can be conducted under heat. The temperature is from room temperature to 80° C. and preferably from room temperature to 50° C.

The silicone compound having an epoxy group and/or the long chain alkyl compound having an epoxy group are preferably added to one to five times equivalent to the acid value of the coloring resin particle having an acid group on the surface.

In particular, in the liquid toner for electrophotography, by using the coloring resin particles surface-treated with a small amount of the compound having an epoxy group, the impact on the properties of such as resistance of the liquid toner is minimized to produce high quality images. In addition, that coloring resin particle having an acid group on the surface is manufactured by the salting-out method means uniform particles are manufactured by an extremely simple method to produce high quality images.

The photocurable liquid ink of the present disclosure is manufactured by: (i) a method of chemically-modifying processed coloring agents (coloring resin particle having an acid group on the surface) with the silicone compound having an epoxy group and/or the long chain alkyl compound having an epoxy group in the photocurable liquid; and (ii) a method of chemically-modifying processed coloring agents (coloring resin particle having an acid group on the surface) with the silicone compound having an epoxy group and/or the long chain alkyl compound having an epoxy group in an organic solvent to obtain coloring resin particles, removing the organic solvent or separating the simple surface-treated coloring resin particles by filtration, and dispersing the resultant in the photocurable liquid again. With regard to the photocurable liquid ink of the present disclosure, (i) is advantageous in which the surface-treated coloring resin particles are manufactured in curable liquid in a single step. This is because the reaction of the silicone compound having an epoxy group and/or the long chain alkyl compound having an epoxy group of the coloring resin particle having an acid group on the surface resultantly produces only ester groups and alcoholic hydroxyl group and no additive is required so that the impact on the properties of the photocurable ink is extremely small.

Furthermore, it is possible to add non-reactive liquid such as highly pure oil and silicone oil to the photocurable liquid ink of the present disclosure to adjust the properties of the liquid such as viscosity, resistance, and dielectric constant. Specific examples of the highly pure oil available in the market include, but are not limited to, ISOPAR G, H, L, and M (manufactured by ExxonMobil Chemical) and NORPAR 12 (manufactured by ExxonMobil Chemical).

Specific examples of the silicon oil available in the market include, but are not limited to, SH-200 series (manufactured by Dow Corning Toray), KF-96 series (ShinEtsu Chemical Co., Ltd.), L-45 series (manufactured by Nippon Unicar Company Limited), and AK-series (Wacker Asahikasei Silicone Co., Ltd). Among these, silicone oil is preferably used. The content of the non-reactive liquid is from 0 to 20% by weight. A content that is too large may invite a curing problem, which is not preferable.

The content of the surface-treated coloring resin particles is preferably from 0.5% by weight to 50% by weight and more preferably from 1% by weight to 30% by weight based on the total amount of the photocurable liquid ink. When the content of the surface-treated coloring resin particles is too small, the coloring ability tends to be poor so that images having a sufficient image density may not be obtained. When the content of the surface-treated coloring resin particles is too large, the viscosity of the photocurable liquid ink tends to increase so that the transferability, extendability, and photocurability of the photocurable liquid ink in an image forming apparatus deteriorate, which leads to production of defective images.

In addition, the average particle diameter (weight average particle diameter) of the surface-treated coloring resin particles is preferably from 0.01 µm to 5 µm. Coloring resin particles that are too large tend to degrade the image quality and settle out while stood still, which leads to agglomeration of the coloring resin particles. Coloring resin particles that are too small tend to increase the agglomeration force, thereby making handling difficult.

As other components to be blended in the photocurable liquid ink of the present disclosure, wax, charge control agents, etc., are suitably added.

There is no specific limit to the selection of the wax and any known wax can be suitably used. Specific examples thereof include, but are not limited to, paraffin wax, polyethylene wax, polypropylene wax, polyester wax, alcohol wax, and urethane wax. These waxes can be used alone or in combination.

There is no specific limit to the selection of the charge control agent and any charge control agent can be suitably used. Specific examples thereof include, but are not limited to, metal salts of sulfosuccinate such as cobalt dialkyl sulfosuccinate, manganese dialkyl sulfosuccinate, zirconium dialkyl sulfosuccinate, and nickel dialkyl sulfosuccinate; metal salts of naphthenate such as manganese naphthenate, calcium naphthenate, zirconium naphthenate, cobalt naphthenate, iron naphthenate, and nickel naphthenate; metal salts of octylate such as manganese octylate, zirconium octylate, calcium octylate, iron octylate, and cobalt octylate; metal salts of dodecylate such as calcium dodecylate, manganese dodecylate, zirconium dodecylate, and magnesium dodecylate; metal salts of alkyl benzene sulfonate such as dodecyl benzene sodium sulfonate, dodecyl benzene calcium sulfonate, and dodecyl benzene barium sulfonate; pigments containing metals such as lecitin, fluorine-containing surface active agents, metal complexes of salicylic acid, and azo compounds; and adine pigments such as quaternary ammonium salts and nigrosine. These waxes can be used alone or in combination.

Known additives can be optionally added to the photocurable liquid ink of the present disclosure. Specific examples thereof include, but are not limited to, dispersing agents, thermostabilizers, antiseptic agents, surface tension adjusting agents, polymerization inhibitors, anti-oxidants, near-infrared absorbents, ultraviolet absorbents, fluorescing agents, and fluorescent brightening agents.

In particular, the polymerization inhibitors are added to inhibit reaction of monomers or oligomers having functional unsaturated group of the curable liquid by heat, etc. Specific examples of the polymerization inhibitors include, but are not limited to, 2,6-di-tert-butyl-4 crezol, anthraquinone, hydroquinone, and hydroquinone monomethylether. Among these, 2,6-di-tert-butyl-4 crezol is preferable because it has an extremely small impact on the liquid properties of the photocurable liquid ink. These can be used alone or in combination.

Figure 2:
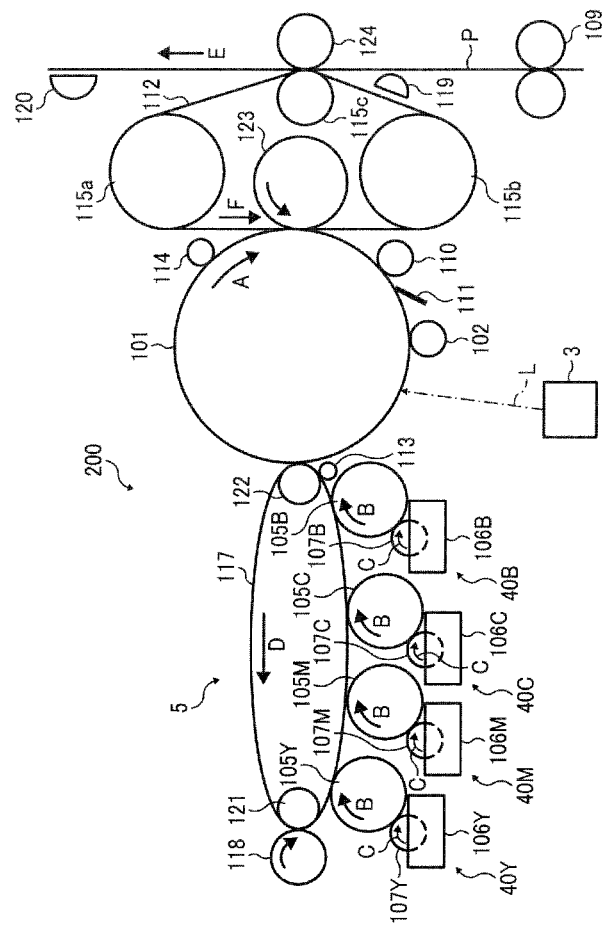
FIG. 2 is a schematic graph illustrating an example of an image forming apparatus that forms color images.

Development devices and image forming apparatuses to which the photocurable liquid ink of the present disclosure is applied are described with reference to FIGS. 1 and 2. FIG. 1 is a schematic diagram illustrating an example of an image forming apparatus employing electrophotography and FIG. 2 is a schematic diagram illustrating an example of a color image forming apparatus employing electrophotography.

The image forming apparatus illustrated in FIG. 1 has a photoreceptor drum 1 (e.g., organic photoconductor) serving as a latent image bearing member in the center.

The photoreceptor drum 1 is provided to rotate the rotation axis perpendicular to the surface of the FIG. 1. Above the photoreceptor drum 1, a manual platform to place manuals are provided. The manual image on the manual platform is read into an image reading element as image signals. The image signals are digitized followed by image processing and transferred to an optical writing unit 3. The optical writing unit 3 optically writes the image on the photoreceptor drum 1.

A latent electrostatic image is formed on the surface of the photoreceptor drum 1 uniformly charged by a charger 2 that has reached the optical writing unit 3.

After the latent electrostatic image on predetermined areas is removed by an erase lamp 4, the latent electrostatic image reaches a development device 5 provided facing the photoreceptor drum 1 on the lateral side of the photoreceptor drum 1. The development device 5 develops the latent electrostatic image with the development liquid to obtain a visual image (toner image). The toner image reaches a transfer device 6 and is transferred to a transfer sheet P as a recording medium fed from a sheet feeder unit by corona discharging of a transfer charger 8. Thereafter, the transfer sheet P to which the toner image is transferred is separated from the surface of the photoreceptor drum 1 by a separating charger, fixed on the transfer sheet P at a fixing unit, and discharged to a discharging tray outside the frame of the image forming apparatus.

The development liquid remaining on the surface of the photoreceptor drum 1 is removed by a cleaner 9 after the toner image is transferred and discharged by a discharging lamp 10 to be ready for the next image formation.

The development device 5, the transfer device 6, and the cleaner 9 in FIG. 1 are described furthermore. The development device 5 is a wet type development device using liquid ink containing carrier liquid containing curable liquid in which toner particles having a coloring agent are dispersed. The development device 5 has a container 51 supported by a base frame and having an opening mouth toward the outer surface of the photoreceptor drum 1, a developing roller 52 serving as a development electrode rotatably supported in the container 51, a squeeze roller 53 serving as a remaining liquid remover, a developing roller scraper 55 with the bottom end slidably abrading the developing roller 52 while supported at the inner wall of the container 51, a squeeze roller scraper 57 to remove the liquid ink on the outer surface of the squeeze roller 53 while supported at the inner wall of the container 51, and a supplying nozzle 54 of a liquid ink supplying tube system 58. Both rotation axes of the developing roller 52 and the squeeze roller 53 are perpendicular to the surface of FIG. 1. The developing roller 52 and the squeeze roller 53 are arranged serially upstream and downstream, respectively relative to the rotation direction of the outer surface of the photoreceptor drum 1.

The developing roller 52 is arranged with a gap K between the outer surface of the developing roller 52 and the outer surface of the photoreceptor drum 1 and the outer surface of the developing roller 52 is driven by a rotation driving device 80 to rotate tin the same rotation direction b as the rotation direction a of the photoreceptor drum 1. The development roller 53 is arranged with a gap L between the outer surface of the development roller 1 and the outer surface of the photoreceptor drum 1 and the outer surface of the development roller 81 is driven by a rotation driving device 80 to rotate in the rotation direction c opposite to the rotation direction a of the photoreceptor drum 1.

The rear end of the developing roller scraper 55 is supported by a slidably abrading actuator 551 and the slidably abrading actuator 551 is connected to a control unit 64 via a connecting circuit. The developing roller scraper 55 is arranged in such a manner that the developing roller scraper 55 can be moved forward and back between the slidably abrading position where the bottom end of the developing roller scraper 55 slidably abrades the outer surface of the developing roller 52 and the retreat position where the bottom end retreats from the outer surface.

Each rotation driving device 80 and 81 is linked to a motor side serving as the rotation power force connected to each rotation transmission system and controllably driven by the control unit 64 in order for both of the developing roller 52 and the squeeze roller 53 to rotate at predetermined rotation velocities. The photoreceptor drum 1 has a rotation driving device 82, which is also controllably driven by the control unit 64.

The lower end of the developing roller scraper 55 is in contact with and slidably abrades the outer circumferential surface of the developing roller 52 on the side opposite to the photoreceptor drum 1, and a wedge portion 56 is formed between the developing roller and the developing roller scraper. Above the wedge portion 56, a supply nozzle 54 of the liquid ink supplying tube system 58 is placed facing the wedge portion. The liquid ink supplying tube system 58 is joined to a liquid ink tank 583 via the pipe 581 equipped with a pump 582. The liquid ink tank 583 accommodates the liquid ink returned from the container 51 and a toner concentration adjusting unit controls the ratio between the carrier liquid and the toner within a constant allowable range. A pump motor 68 to drive the pump 582 is connected to a power source 69 via a drive switch 70 and this drive switch 70 is turned on/off by the control unit 64.

The developing roller 52 also serves as a developing electrode, in which a conductive member is provided inside the surface of a dielectric body and the conductive member is connected to a bias circuit 60.

This bias circuit 60 connects the developing roller 52 to first and second power sources 61 and 62 via a bias voltage switch 63. The first power source 61 applies a voltage to attract the toner in the liquid ink toward the developing roller 52, the second power source 62 applies a voltage to pull the toner away the toner in the liquid ink from the developing roller 52, and switching of the bias voltage switch 63 is controlled by the control unit 64. It should be noted that the bias voltage switch 63 may be dispensed with, by employing the first power source 61 as the only power source.

The squeeze roller 53 rotationally moves in the opposite direction to the moving direction of the surface of the photoreceptor drum 1 with the gap L maintained. This is to regulate the liquid film thickness of the liquid ink attached to the surface of the image bearing member (photoreceptor drum 1) and the scraped liquid ink flows down to the bottom of the container 51 by the squeeze roller scraper 57. Regarding the squeeze roller 53, a conductive member is provided inside the surface of the dielectric body and the conductive member is connected to a bias circuit 73. This bias circuit 73 connects the squeeze roller 53 to first and second power sources 65 and 66 in a switchable manner via a bias voltage switch 67.

The first power source 65 applies a voltage to attract the toner in the liquid ink toward the developing roller 53, the second power source 66 applies a voltage to pull away the toner in the liquid ink from the developing roller 53, and switching of the bias voltage switch 67 is controlled by the control unit 64. Placed facing the outer circumferential surface of the photoreceptor drum 1, a liquid ink supply unit 90 is positioned downstream from the place where the developing roller 52 faces the photoreceptor drum 1 and upstream from the place where the squeeze roller 53 faces the photoreceptor drum 1.

This developing liquid supply unit 90 can directly supply the liquid ink as a supplementary liquid to a supply position where the squeeze roller 53 faces the surface of the photoreceptor drum 1.

The liquid ink supply unit 90 includes a supplemental liquid nozzle 91 placed facing the surface of the photoreceptor drum 1; a supplemental liquid supply pipe 92 which joints this nozzle and the developing liquid tank 583; and a pump 93 on the supplementary liquid supply pipe 92. A pump motor 94 to drive the pump 93 is connected to a power source 69 via a drive switch 95, and this drive switch 95 is turned on/off by the control unit 64.

The transfer device 6 has a belt form and includes a transfer member 12 whose surface is covered with a dielectric body and a transfer charger 8 placed facing the photoreceptor surface at the transfer position via the transfer member 12. When the transfer device 6 is driven, the transfer device 6 transfers the toner image formed on the photoreceptor drum 1 onto the transfer paper P by corona discharging by the transfer charger 8.

At this point of time, the belt-form transfer member 12 is operated to move at the same speed as the outer circumferential surface of the photoreceptor drum 1 by means of a driving unit, moves the fed transfer paper P at the same speed while bringing it into contact with the surface of the photoreceptor drum 1, and transfers the toner image formed on the photoreceptor surface onto the transfer paper P by the electric force imparted by the transfer charger 8.

The cleaner 9 is to remove the liquid ink remaining on the photoreceptor drum 1 after transferring the toner image and includes a movable plate member 13 which is detachably attachable to the photoreceptor drum 1 and an actuator 71 which switches the movable plate member 13 between the cleaning position shown by the solid line and the retreat position shown by the broken line.

The actuator 71 is a solenoid and its driving power is output from a drive circuit 72 instructed by the control unit 64. As described above, the liquid ink color image transferred on to the transfer sheet P is fixed on the transfer sheet P by optical curing upon irradiation of ultraviolet by a light irradiation unit 120 for fixing in FIG. 2.

As described above, a color image containing coloring resin particles is appropriately fixed on the transfer sheet P to securely prevent the color image from peeling off from the transfer sheet P.

Next, the mechanism of forming color images on the transfer sheet P is described with reference to FIG. 2. An electrophotographic image forming apparatus 200 to form color images shown in FIG. 2 includes a drum-form photoconductor 101 as an image bearing member which rotates in the direction indicated by the arrow A; a developing device 5 including liquid ink supply units 40Y, 40M, 40C and 40B configured to supply photocurable liquid ink of yellow, magenta, cyan, and black, respectively; and an intermediate transfer belt 112 having an endless form which is supported by a drive roller 115a and support rollers 115b and 115c and moved in the direction indicated by the arrow F.

The developing device 5 also includes a conveyance belt 117 in the form of an endless belt, supported by a drive roller 121 and a support roller 122 and moved in the direction of the arrow D. The photocurable liquid ink of yellow, magenta, cyan, and black are supplied to this conveyance belt 117 from the liquid ink supply units 40Y, 40M, 40C, and 40B respectively, the toner particles containing coloring agent in the photocurable liquid ink are charged by a corona discharge unit 113, and the photocurable liquid ink is supplied to the photoconductor 101 on the support roller 122. A reference numeral 102 represents a corona charger to charge the photoconductor 101.

The liquid ink supply units 40Y, 40M, 40C, and 40B include liquid ink containers 106Y, 106M, 106C, and 106B, respectively, that accommodate the yellow, magenta, cyan, and black photocurable liquid ink each including the toner particles and the photocurable liquid containing the silicone compound 1. Furthermore, the liquid ink supply units 40Y, 40M, 40C, and 40B include liquid ink supply rollers 107Y, 107M, 107C, and 107B which lift the photocurable liquid ink from the liquid ink containers 106Y, 106M, 106C, and 106B while rotating in the direction indicated by the arrow C and developing rollers 105Y, 105M, 105C, and 105B which supply the photocurable liquid ink supplied from the liquid ink supply rollers 107Y, 107M, 107C, and 107B in such a manner as to have a predetermined coating thickness to the surface of the conveyance belt 117 while rotating in the direction indicated by the arrow B.

In this case, the photocurable liquid ink of yellow, magenta, cyan and black is supplied from the liquid ink supply units 40Y, 40M, 40C, and 40B to the conveyance belt 117 in such a manner that the corresponding ink is supplied to latent electrostatic images for each color formed on the photoconductor 101 by a writing unit according to image information for each color.

Specifically, when a latent electrostatic image of yellow is formed, only the yellow photocurable liquid ink is supplied from the yellow liquid ink supply unit 40Y to the latent electrostatic image on the photoconductor 101 via the conveyance belt 117 to develop the latent electrostatic image with the yellow curable liquid ink.

The thus-formed yellow liquid curable liquid ink image is charged by a corona discharger 114 and transferred onto the intermediate transfer belt 112 by a primary transfer roller 123. Similarly, when a liquid ink image corresponding to a magenta image is formed, the magenta photocurable liquid ink is supplied from the liquid ink supply unit 40M to the photoconductor 101 so as to form a magenta curable liquid ink image. This magenta curable liquid ink image is transferred and superimposed onto the yellow curable liquid ink image that has been transferred onto the intermediate transfer belt 112.

Similarly, cyan and black curable liquid ink images are transferred and superimposed onto the liquid ink images on the intermediate transfer belt 112 so that a color image is formed.

The thus-formed curable color liquid ink image on the intermediate transfer belt 112 is partially cured by a pre-transfer light irradiation unit 119 to demonstrate the surface adhesiveness. The curable liquid ink image to which the surface adhesiveness is provided is synchronously transferred by a secondary transfer roller 124 onto the transfer sheet P (recording medium) conveyed in the direction indicated by the arrow E by a registration roller 109.

The color liquid ink image transferred onto the transfer sheet P is optically cured upon irradiation of ultraviolet by a fixation light irradiation unit 120 and fixed on the recording medium P.

In the image forming apparatus 200, the photocurable liquid ink remaining on the conveyance belt 117 and/or the photoconductor 101 is removed by a cleaning roller 118, a cleaning roller 110, and a cleaning blade 111 to return the photoconductor 101 to the initial state. As described above, a color image containing a coloring agent is appropriately fixed on the transfer sheet P to securely prevent the color image from peeling off from the transfer sheet P.

The following describes a case in which the photocurable liquid ink according to the present disclosure is applied to an inkjet recording method of printing images formed of recording dots by flying the photocurable liquid ink to a recording medium.

The inkjet recording method of printing images formed of recording dots by flying the photocurable liquid ink to a recording medium is appealing as a non-impact recording method that facilitates colorization and enables direct recording onto plain paper. Printers employing this method have started to gain acceptance in the market.

The inkjet recording methods are broadly classified into on-demand (on-demand jetting) methods and continuous (continuous jetting) methods. Furthermore, known examples of the continuous methods are electrostatic methods (Sweet type, Hertz type), and known examples of the on-demand methods include, but are not limited to, piezoelectric methods, shear-mode piezoelectric methods, and thermal inkjet methods. For instance, the method referred to as "electrostatic acceleration type inkjet method" or "slit jet method", described in "IEICE TRANSACTIONS on Fundamentals of Electronics, Communications and Computer Sciences Vol. J66-C (No. 1), P47 (1983) by Susumu Ichinose and Yuji Oba", and "The Journal of the Institute of Image Electronics Engineers of Japan Vol. 10 (no.3), P157 (1981) by Tadayoshi Ohno and Mamoru Mizuguchi", is known as one of the on-demand inkjet recording methods.

The photocurable liquid ink including the silicone compound 1 of the present disclosure is suitably used in the piezoelectric method and the shear-mode piezoelectric method. What is different from the photocurable liquid ink used in an electrophotographic method is that the particle diameter of the coloring resin particles is basically required to be smaller than the nozzle diameter of an inkjet head.

Specifically, the diameter of the surface-treated coloring resin particles is preferably in the range of from 0.01 μm to 0.5 μm and more preferably, 0.01 μm to 0.3 μm.

Moreover, instead of using the coloring resin particles having a small particle diameter manufactured by a salting-out method, etc. as described above, it is possible to simply use a method in which a commercially available coloring agent or the processed coloring agent (coloring resin particles) described above is dispersed in the photocurable liquid containing the silicone compound 1. In this case, a dispersant or a dispersion stabilizer is optionally added. As the dispersant and the dispersion stabilizer, polyether-modified silicone oils can be suitably used. Specific examples of the commercially-available polyether-modified silicone oils include, but are not limited to, KF-945, KF-6020, KF-352A, KF-353, KF-615A, X-22-4515, KF-6012, KF-6015 and KF-6017 (manufactured by Shin-Etsu Chemical Co., Ltd.), and FZ-2154, FZ-2191, FZ-2130, SH-8400 and FZ-2123 (manufactured by Dow Corning Toray Co., Ltd.).

Among these, it is suitable to use polyether-modified silicone oils having HLB values of from 2 to 10, in particular, polyether-modified silicone oils having HLB values of 4 to 7 such as KF-945, KF-6020, FZ-2154 and FZ-2130.

Furthermore, with regard to pigment dispersion methods, any of the processed coloring agents (coloring resin particles) can be suitably used. That is, among the processed coloring agent described above, the processed coloring agent having an acidic group on the surface based upon an acidic group-containing resin used as a carrier resin is chemically modified with the silicone compound having an epoxy group and/or the long chain alkyl compound having an epoxy group in the photocurable liquid which contains the silicone compound 1 to disperse the coloring agent and stabilize the dispersion by the reaction between the acidic group of the carrier resin and the epoxy group simultaneously, resulting in production of extremely excellent photocurable liquid ink.

Also, since the electrostatic acceleration type inkjet method basically uses an inkjet head having no nozzles, meaning that there is no limit to the particle diameter of the coloring resin particles, it is possible to use any liquid ink of a photocurable ink for electrophotography, a photocurable liquid ink for a piezoelectric method and a photocurable liquid ink for a shear-mode piezoelectric method.

Next, a method of photocuring the photocurable liquid ink according to the present invention will be described. After an image formed with the photocurable liquid ink of the present disclosure is developed, the developed liquid ink image is irradiated with light so as to solidify the photocurable liquid on the liquid ink image.

The photocuring can be conducted before and/or after the image is transferred to a recording medium. The pre-transfer light irradiation partially cures the formed liquid ink image before the image transfer, imparts the formed liquid ink image with surface adhesiveness, and promotes the transfer thereof to the recording medium (adhesive transfer method). The post-transfer light irradiation accelerates curing of the developed liquid ink image, thereby promoting attachment of the liquid ink image to the recording medium. The photocuring can be suitably conducted by a known method.

When a photopolymerization initiator is used, curing is conducted by irradiating and exposing the liquid ink image to active energy rays such as ultraviolet rays having a wavelength to which the initiator is sensitive.

As the active energy rays, electron rays, ultraviolet rays, and visible rays are suitable. The peak wavelength of the active energy rays is, for example, preferably in the range of from 300 nm to 450 nm, although depending upon the absorption properties of a sensitizer. The active energy ray used for the curing system applied to the photocurable liquid ink of the present disclosure preferably has an exposure surface illuminance of 10 mW/cm$^2$ to 2,000 mW/cm$^2$.

As active energy ray sources, mercury lamps and gas/solid-state lasers are dominantly used. In particular, as the light source for use to cure ultraviolet curable liquid ink, mercury lamps and metal halide lamps are widely diffused. However, at present, use of mercury-free sources is strongly demanded to protect the environment.

Therefore, replacing the mercury-based sources with GaN-based semiconductor ultraviolet devices is extremely advantageous in terms of industry and environment. Furthermore, LEDs (light emitting diodes) (UV-LEDs) and LDs (UV-LDs) are expected as the light source for photocurable liquid ink because they are compact, efficient, and long-lasting.

Furthermore, the photocurable liquid ink of the present disclosure optionally include a photopolymerization initiator to initiate curing of the photocurable liquid which contains any of the silicone compounds 1 to 6.

There is no specific limit to the selection of the photopolymerization initiator and any known photopolymerization initiator is suitably used. Specific examples of photopolymerization initiators include, but are not limited to, benzoin, benzoin methyl ether, benzoin ethyl ether, benzoin isopropyl ether, benzoin-n-butyl ether, benzoin isobutyl ether, acetophenone, dimethylacetophenone, 2,2-dimethoxy-2-phenylacetophenone, 2,2-diethoxy-2-phenylacetophenone, 2-hydroxy-2-methyl-1-phenylpropane-1-one, 1-hydroxycyclohexyl phenyl ketone, 2-methyl-1-[4-(methylthio)phenyl]-

2-morpholino propane-1-one, 4-(2-hydroxyethoxy)phenyl-2-hydroxy-2-propylketone, benzophenone, p-phenylbenzophenone, 4,4-diethylamino benzophenone, dichlorobenzophenone, 2-methylanthraquinone, 2-ethylanthraquinone, 2-tert-butylanthraquinone, 2-aminoanthraquinone, 2-methylthioxanthone, 2-ethylthioxanthone, 2-isopropylthioxanthone, 2-chlorothioxanthone, 2,4-dimethylthioxanthone, 2,4-diethylthioxanthone, benzyl dimethyl ketal, acetophenone dimethyl ketal, 2,4,6-trimethyl benzoyl-diphenyl phosphine oxide, 6-trimethyl benzoyl diphenylphosphine oxide, 2-benzyl-2-dimethylamino-1-(4-morpholinophenyl)-butan-1-one, bis(2,6-dimethoxybenzoyl)-2,4,4-trimethylpentylphosphine oxide, and p-dimethyl aminobenzoate. These can be used alone or in combination. The content of the photopolymerization initiator ranges from 0.05% by weight to 20% by weight and preferably 0.2% by weight to 15% by weight, relative to the total amount of the photocurable liquid ink. Any of these photopolymerization initiators can be added before or after the image development.

In general, properties required for the photocurable liquid ink are as follows:

Curability

Naturally, high productivity is demanded to form an image for graphic art, a sign, a display, a label, etc. using the photocurable liquid ink. Moreover, the photocurable liquid ink provided to a recording medium flows on the recording medium due to its fluidity, thereby causing flowing, smearing, or rejecting, which degrades the image quality. Accordingly, to avoid or prevent such problems, the photocurable liquid ink is required to cure quickly upon irradiation of light and fix on a recording medium.

Liquid Properties

With regard to the photocurable liquid ink provided to a recording medium, it is preferable that the photocurable liquid ink has a relatively low viscosity and excellent dispersability and dispersion stability of the coloring agent or the coloring resin particles in terms of achieving high-speed driving.

Also, demand for reducing the particle diameter of the coloring agent or the coloring resin particles has been strong as the image quality improves. Satisfying these conflicting matters including low viscosity, high dispersibility, and particle size reduction at the same time at a high level is inevitable.

Curable Film Properties

There are broadly three properties required for the cured film of the ink. The first of the properties is strength of the cured film In the case where an image is used for a display, label, etc., the image may be damaged owing to rubbing, scratching, or memo by a user, the effects of dust, etc. Therefore, the image is required to have durability to such damage.

The second of the properties is adhesion of the cured film to a recording medium. The image should stay on the recording medium without lifting or peeling off even when exposed to an unfavorable environment or under a force caused by rolling or folding. Therefore, the cured film is required to stick firmly and uniformly to the recording medium.

The third of the properties is stickiness of the cured film. For example, a cured film having stickiness like glue tends to cause images to stick to each other, adsorb dust or contamination, which may degrade the value of the images. Therefore, reducing stickiness of a cured film is inevitable.

Stability

Similar to commonplace ink, the photocurable liquid ink circulates and retains in the market and possibly accumulates in an apparatus. Accordingly, it is necessary to avoid thickening, curing, or decomposition of ingredients, resulting in degradation of the performance of the liquid ink in a period of time which is too short in terms of social acceptance. Sustaining curability is also required. In addition, although the photocurable liquid ink is mixed with additives such as a charge control agent in most cases, it is inevitable to avoid degrading the intended properties of the photocurable liquid ink by additives.

The silicone compounds 1 to 6 have a low viscosity and are easy to handle and in addition have a high curability in comparison with typical silicone compounds having a functional group such as methacryloxy group in its molecule.

The photocurable liquid ink having the silicone compound 1 to 6 satisfies the characteristics mentioned above and high-resolution images without background fouling or image blur can be produced by using photocurable liquid ink.

Furthermore, homogeneous coloring resin particles having a relatively high mono-dispersion property can be easily manufactured by a salting-out method and fundamental properties related to the liquid such as viscosity, resistance, and dielectric constant are stabilized. Further, the presence of the siloxyl group and/or the long-chain alkyl group on the surfaces of the coloring resin particles gives the coloring resin particles excellent dispersibility and re-dispersibility with little or no additives such as dispersants. As a result of the total of these, the photocurable liquid ink of the present disclosure has stable ink characteristics and stably and reliably forms high-definition quality images.

Having generally described (preferred embodiments of) this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, the present disclosure is furthermore described in detail with reference to Examples but not limited thereto.

The methods and instrument used in measuring the photocurable liquid are as follows.

Measurement of Average Particle Diameter and Relative Standard Deviation (CV Value)

Measuring instrument: Particle Size Analyzer FPAR-1000 (manufactured by Otsuka Electronics Co., Ltd.)

Sample: 1.0% by weight aqueous solution of the photocurable liquid ink

Measurement of Acid Value

The acid value is measured in accordance with JIS K0070.

Measurement of Curing Speed

Measuring Instrument Viscosity/Viscoelasticity Measuring Instrument (VAR-200AD, manufactured by Reologica Instruments)

Light source: LED light source C-L1 (manufactured by Hamamatsu Photonics K.K., 365 nm)

Measuring frequency: 1 Hz Measuring stress: 150 Pa

Measuring plate: 20 mm φ (gap: 10 μm)

Under the conditions mentioned above, preliminarily set the irradiation surface illuminance to be 50 mW/cm$^2$, transfuse the sample in the measuring plate, and measure the irradiation time required for curing to calculate the curing energy.

The indication of curing is an elasticity of $1 \times 10^4$ Pa.

Synthesis Example I-1

Manufacturing of Coloring Resin Particle Having Acid Group on Surface by Salting-Out Method Prepare a 10% by weight aqueous solution of UC-3910 containing 380.5 parts of water, 249.5 1N-potassium hydroxide, and 70 parts of styrene/acrylic resin: UC 3910 (Mw=8, 500, Tg=85° C., acid value: 200 mgKOH/g, manufactured by Toagosei Co., Ltd.) and conduct a ball mill treatment for 70 parts of 10% by weight aqueous solution of UC-3910 and 7 parts of carbon black #5B (manufactured by Mitsubishi Chemical Corporation) with a 2 mm φ zirconia ball for 12 hours to obtain a ball-mill coloring agent liquid dispersion.

Thereafter, pour a coloring agent liquid dispersion obtained by removing the zirconia ball from the ball-mill coloring agent liquid dispersion and 123 parts of water in a flask equipped with a stirrer, a thermometer, and a dripping funnel followed by cooling down to 5° C. while stirring and drip 102.6 parts of saturated ammonium sulfate to the flask in one hour in cooling condition.

Furthermore, stir the resultant for two hours under the same condition followed by acidization by $0.2N-H_2SO_3$, filter and wash the resultant with water twice. Freeze and dry the resultant to obtain 13.46 parts of coloring resin particles (α) having a carboxyl group on the surface.

The volume average particle diameter of the coloring resin particles (α) is 0.18 μm, the relative standard deviation (CV value) is 28%, and the acid value is 72 mgKOH/g.

Synthesis Example I-2

Manufacturing of Toner Particle by Coacervation Method

Place 800 parts of branch-chained aliphatic hydrocarbon ISOPAR G (manufactured by Exxon Mobil Corporation), 480 parts of toluene, and 300 parts of ethanol first in a container equipped with a thermometer and a reflux cooler and furthermore 40 parts of partially-saponified copolymers of ethylene and vinyl acetate (DUMILAN C-2280, manufactured by Takeda Pharmaceutical Company Limited.), 13.3 parts of carbon black #5B (manufactured by Mitsubishi Chemical Corporation), and 8 parts of phosphporic acid ester surface active agent (PLYSURF AP, manufactured by Dai-Ichi Kogyo Seiyaku CO., LTD.) followed by three-hour vigorous stirring at 70° C. to manufacture liquid dispersion of carbon black.

Gradually cool down this liquid dispersion of carbon black to 30° C. while gently stirring, distill away toluene and ethanol from the liquid dispersion with a reduced pressure to precipitate colored particles, filter the resultant followed by drying with a reduced pressure to obtain 76.4 parts of toner particles (β).

The volume average particle diameter of the toner particles (β) is 0.25 μm, the relative standard deviation (CV value) is 320%.

Synthesis Example a-II-1

Synthesis of Alkenyl Body as Material to Compose Substituent A-1: Compound of R1=H Place 13.42 parts of 2-arylphenol, 10.33 parts of methacrylic acid, and 180 parts of toluene in a container equipped with a stirrer, a thermometer, and a dripping funnel and drip 15.14 part of diisopropyl carbodimide in about 30 minutes to the container at room temperature while stirring.

Furthermore, drip toluen solution containing 1.22 parts of dimethylamino pyridine to the container in about ten minutes to obtain a reaction product after six-hour stirring at room temperature. Next, condense the reaction product to about a half by volume followed by silica gel chromatography using toluene as a developing solvent to obtain 20.11 parts of 2-methachloxy aryl benzene (Compound a-II-1).

Figure 3A:
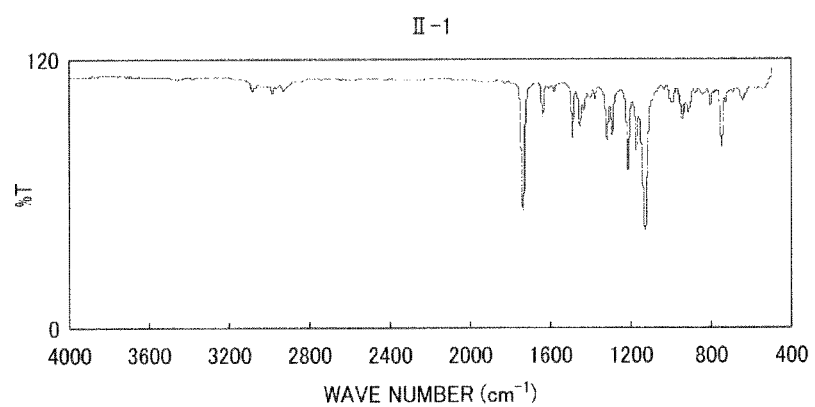
FIG. 3A is a graph illustrating an infrared absorption spectrum of a compound a-II-1.

The infra-red absorption spectrum graph is shown as FIG. 3A.

Synthesis Example a-II-1

Synthesis of Alkenyl Body as Material to Compose Substituent A-1: Compound of $R1=CH_3$ Place 14.82 parts of 2-aryl-6-methylphenol, 10.33 parts of methacrylic acid, and 180 parts of toluene in a container equipped with a stirrer, a thermometer, and a dripping funnel and drip 15.14 parts of diisopropyl carbodimide in about 30 minutes to the container at room temperature while stirring.

Furthermore, drip toluen solution containing 1.22 parts of dimethylamino pyridine to the container in about ten minutes to obtain a reaction product after six-hour stirring at room temperature.

Next, condense the reaction product to about a half by volume followed by silica gel chromatography using toluene as a developing solvent to obtain 19.31 parts of 2-methachloxy-6-methyl aryl benzene (Compound a-II-2).

Synthesis Example a-III-1

Synthesis of Silicone Compound: l=0, m=1, and n=0 in the Chemical Structure 2

Drip 3.80 parts of the compound a-II-1 (2-methacryloxy aryl benzene), 0.008 parts of a stabilizer (2,6-di-t-butyl-4-methylphenol), 10 parts of toluene, and 0.034 parts of xylene solution of 2% by weight platinum/1,3-divinyl-1,1,3,3-tetramethyl disiloxane complex (manufactured by Sigma-Aldrich Co.) to a solution of 4 parts of methyl hydrogen silicone compound (1,1,1,3,5,5,5-heptamethyl trisiloxane) and 4 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C., and confirm disappearance of absorption (2155 $cm^{-1}$ of Si—H in infra-red absorption spectrum to obtain 7.83 parts of the target silicone compound a-M1.

Figure 3B:
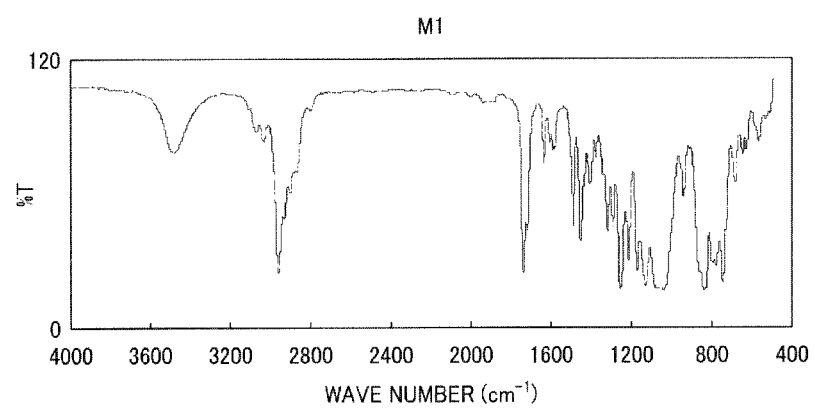
FIG. 3B is a graph illustrating an infrared absorption spectrum of a silicone compound a-M1.

The infra-red absorption spectrum graph is shown as FIG. 3B.

Synthesis Example a-III-2

Synthesis of Silicone Compound: l=0 in the Chemical Structure 3

Drip 6.29 parts of the compound a-II-1 (2-methacryloxy aryl benzene), 0.014 parts of a stabilizer (2,6-di-t-butyl-4-methylphenol), 10 parts of toluene, and 0.057 parts of xylene solution of 2% by weight platinum/1,3-divinyl-1,1,3,3-tetramethyl disiloxane complex (manufactured by Sigma-Aldrich Co.) to a solution of 2 parts of methyl hydrogen silicone compound (1,1,3,3-tetramethyl disiloxane) and 2 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C., and confirm disappearance of absorption (2155 $cm^{-1}$ of Si—H in infra-red absorption spectrum to obtain 8.24 parts of the target silicone compound a-M2.

Figure 3C:
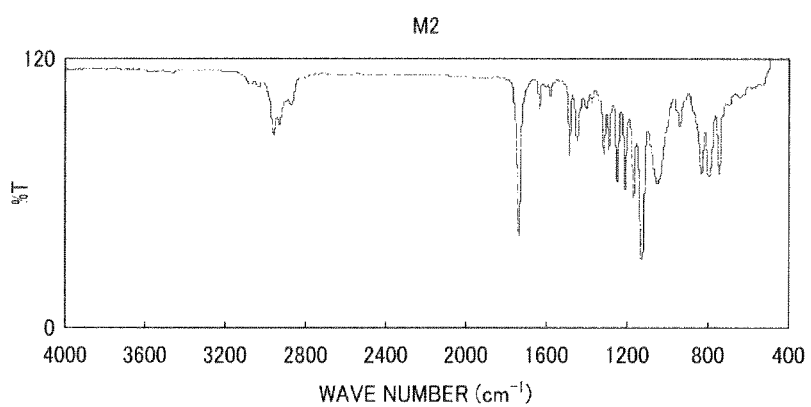
FIG. 3C is a graph illustrating an infrared absorption spectrum of a silicone compound a-M2.

The infra-red absorption spectrum graph is shown as FIG. 3C.

Synthesis Example a-III-3

Synthesis of Silicone Compound: 1=1 in the Chemical Structure 3

Drip 6.08 parts of the compound a-II-1 (2-methacryloxy aryl benzene), 0.013 parts of a stabilizer (2,6-di-t-butyl-4-methylphenol), 10 parts of toluene, and 0.055 parts of xylene solution of 2% by weight platinum/1,3-divinyl-1,1,3,3-tetramethyl disiloxane complex (manufactured by Sigma-Aldrich Co.) to a solution of 3 parts of methyl hydrogen silicone compound (1,1,3,3,5,5,-hexamethyl trisiloxane) and 3 parts of toluene at room temperature in about 60 minutes while stirring followed by reaction under the same condition one night. Thereafter, distill away the solvent with a reduced pressure, conduct stripping treatment for two hours with a reduced pressure of 10 mmHg at 40° C., and confirm disappearance of absorption (2155 cm$^{-1}$ of Si—H in infra-red absorption spectrum to obtain 9.09 parts of the target silicone compound a-M3.

Figure 3D:
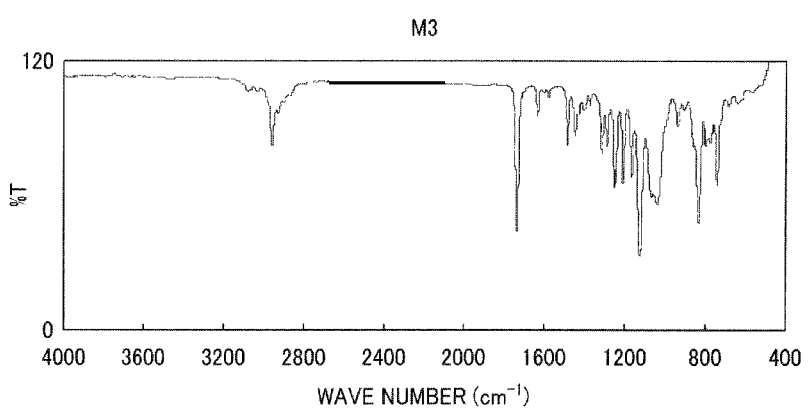
FIG. 3D is a graph illustrating an infrared absorption spectrum of a silicone compound a-M3.

The infra-red absorption spectrum graph is shown as FIG. 3D.

Synthesis Example a-III-4

Synthesis of Silicone Compound 3:1 is Nearly Equal to 6 in the Chemical Structure 3

Drip 3.64 parts of the compound a-II-1 (2-methacryloxy aryl benzene), 0.008 parts of a stabilizer (2,6-di-t-butyl-4-methylphenol), 10 parts of toluene, and 0.033 parts of xylene solution of 2% by weight platinum/1,3-divinyl-1,1,3,3-tetramethyl disiloxane complex (manufactured by Sigma-Aldrich Co.) to a solution of 5 parts of methyl hydrogen silicone compound (polydimethylsiloxane, both ends terminated with hydrogen atom (molecular weight: up to 580, manufactured by Sigma-Aldrich Co.), and 5 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C., and confirm disappearance of absorption (2155 cm$^{-1}$ of Si—H in infra-red absorption spectrum to obtain 8.62 parts of the target silicone compound a-M4.

Figure 3E:
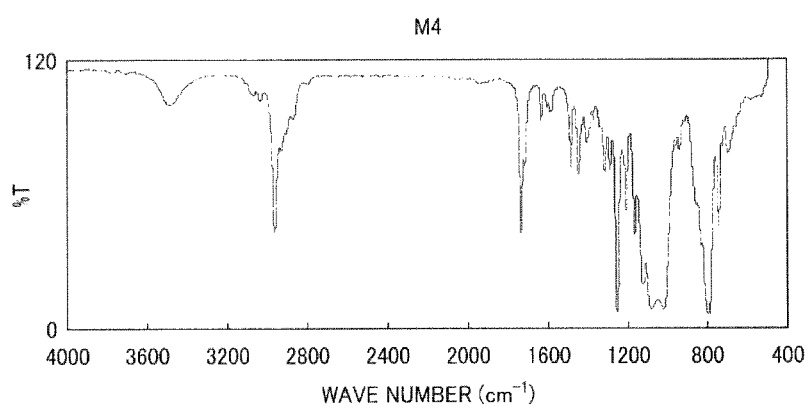
FIG. 3E is a graph illustrating an infrared absorption spectrum of a silicone compound a-M4.

The infra-red absorption spectrum graph is shown as FIG. 3E.

Synthesis Example a-III-5

Synthesis of Silicone Compound: 1=m=6, n=0 in the Chemical Structure 2

Drip 5.22 parts of the compound a-II-1 (2-methacryloxy aryl benzene), 0.011 parts of a stabilizer (2,6-di-t-butyl-4-methylphenol), 0.011 parts of toluene, and 0.047 parts of xylene solution of 2% by weight platinum/1,3-divinyl-1,1,3,3-tetramethyl disiloxane complex (manufactured by Sigma-Aldrich Co.) to a solution of 4 parts of methyl hydrogen silicone compound: copolymer of poly[dimethyl silicone/methylhydro silicone) (mol ratio: 50%)] (molecular weight: up to 950, manufactured by Sigma-Aldrich Co.), and 4 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C., and confirm disappearance of absorption (2155 cm$^{-1}$ of Si—H in infra-red absorption spectrum to obtain 9.41 parts of the target silicone compound a-M5.

Figure 3F:
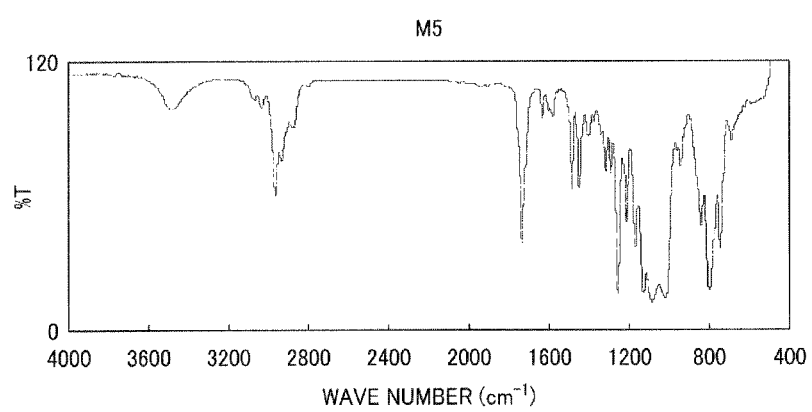
FIG. 3F is a graph illustrating an infrared absorption spectrum of a silicone compound a-M5.

The infra-red absorption spectrum graph is shown as FIG. 3F.

Synthesis Example a-III-6

Synthesis of Silicone Compound: 1=6, m=n=3, Y=Decyl group in the Chemical Structure 2

Drip 1.86 parts of the compound a-II-1 (2-methacryloxy aryl benzene), 1.30 parts of 1-decene, 0.004 parts of a stabilizer (2,6-di-t-butyl-4-methylphenol), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3 parts of methyl hydrogen silicone compound: copolymer of poly[dimethylsilicone/methylhydrosilicone) (mol ratio: 50%), molecular weight: up to 950, manufactured by Sigma-Aldrich Co.), and 3 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C. to obtain 6.35 parts of the target silicone compound a-M6.

Figure 3G:
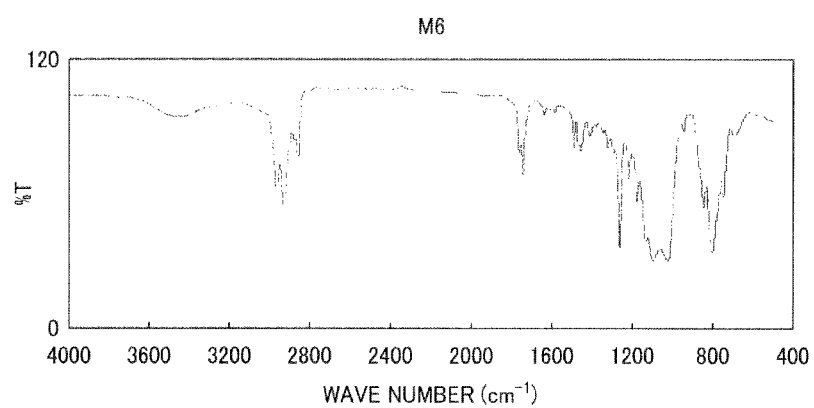
FIG. 3G is a graph illustrating an infrared absorption spectrum of a silicone compound a-M6.

The infra-red absorption spectrum graph is shown as FIG. 3G

Synthesis Example a-III-7

Synthesis of Silicone Compound: 1=6, m=n=3, Y=Phenoxypropyl Group in the Chemical Structure 2

Drip 1.86 parts of the compound a-II-1 (2-methacryloxy aryl benzene), 1.24 parts of arylphenyl ether, 0.004 parts of a stabilizer (2,6-di-t-butyl-4-methylphenol), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3 parts of methyl hydrogen silicone compound: copolymer of poly[dimethylsilicone/methylhydrosilicone) (mol ratio: 50%)] (molecular weight: up to 950, manufactured by Sigma-Aldrich Co.) and 3 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C., and confirm disappearance of absorption (2155 cm$^{-1}$ of Si—H in infra-red absorption spectrum to obtain 6.41 parts of the target silicone compound a-M7.

Figure 3H:
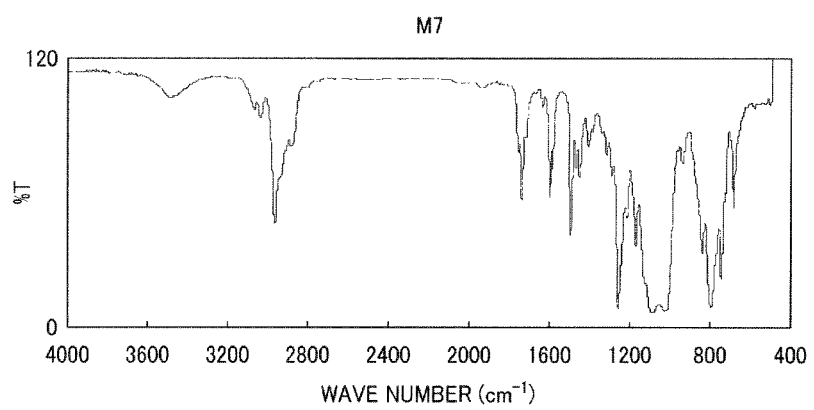
FIG. 3H is a graph illustrating an infrared absorption spectrum of a silicone compound a-M7.

The infra-red absorption spectrum graph is shown as FIG. 3H.

Synthesis Example a-III-8

Synthesis of Silicone Compound: 1=6, m=n=3, Y=2-pentamethyl disiloxyethyl group) in the Chemical Structure 2

Drip 1.86 parts of the compound a-II-1 (2-methacryloxy aryl benzene), 1.61 parts of vinylpentamethyl disiloxane, 0.004 parts of a stabilizer (2,6-di-t-butyl-4-methylphenol), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3 parts of methyl hydrogen silicone compound: copolymer of poly[dimethylsilicone/methylhydrosilicone) (mol ratio: 50%) (molecular weight: up to 950, manufactured by Sigma- Aldrich Co.) and 3 parts of toluene at room temperature in about 60 minutes while stirring followed by reaction under the same condition one night. Thereafter, distill away the solvent with a reduced pressure, conduct stripping treatment for two hours with a reduced pressure of 10 mmHg at 40° C. to obtain 6.16 parts of the target silicone compound a-M8.

Synthesis Example a-IV

Synthesis of Alkenyl Body as Material to Compose Substituent C

Place 16.42 parts of 2-methoxy-4-arylphenol, 9.47 parts of methacrylic acid, and 180 parts of toluene in a container equipped with a stirrer, a thermometer, and a dripping funnel and drip 13.88 parts of diisopropyl carbodimide in about 30 minutes to the container at room temperature while stirring. Furthermore, drip toluen solution containing 1.22 parts of dimethylamino pyridine to the container in about ten minutes to obtain a reaction product after six-hour stirring at room temperature.

Next, condense the reaction product to about a half by volume followed by silica gel chromatography using toluene as a developing solvent to obtain 22.24 parts of 3-methachloxy-4-methacryloxy arylbenzene (Compound a-IV).

Figure 3I:
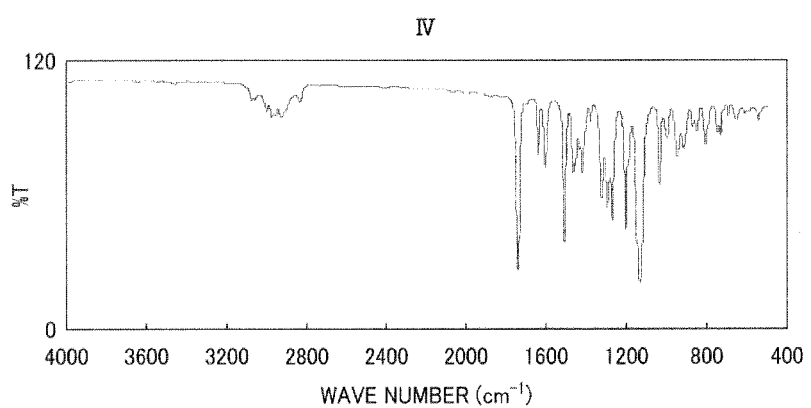
FIG. 3I is a graph illustrating an infrared absorption spectrum of a silicone compound a-IV.

The infra-red absorption spectrum graph is shown as FIG. 3I.

Synthesis Example a-V-1

Synthesis of Silicone Compound: 1 is nearly equal to 6 in the Chemical Structure 5

Drip 2.52 parts of the compound a-IV (3-methoxy-4-methachryloxy aryl benzene), 0.005 parts of a stabilizer (2,6-di-t-butyl-4-methylphenol), 10 parts of toluene, and 0.020 parts of xylene solution of 2% by weight platinum/1,3-divinyl-1,1,3,3-tetramethyl disiloxane complex (manufactured by Sigma-Aldrich Co.) to a solution of 3.0 parts of methyl hydrogen silicone compound (polydimethylsiloxane, both ends terminated with hydrogen atom (molecular weight: up to 580, manufactured by Sigma-Aldrich Co.), and 3.0 parts of toluene at room temperature in about 60 minutes while stirring followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.60 parts of the target silicone compound a-M9.

Figure 3J:
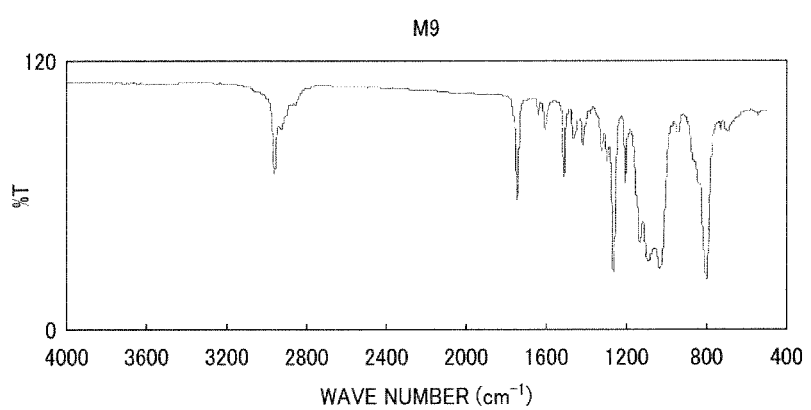
FIG. 3J is a graph illustrating an infrared absorption spectrum of a silicone compound a-M9.

The infra-red absorption spectrum graph is shown as FIG. 3J.

Synthesis Example a-V-2

Synthesis of Silicone Compound: 1=2 in the Chemical Structure 5

Drip 3.45 parts of the compound a-IV (3-methoxy-4-methacryloxy arylbenzene), 0.006 parts of a stabilizer (2,6-di-t-butyl-4-methylphenol), 10 parts of toluene, and 0.027 parts of xylene solution of 2% by weight platinum/1,3-divinyl-1,1,3,3-tetramethyl disiloxane complex (manufactured by Sigma-Aldrich Co.) to a solution of 2.0 parts of methyl hydrogen silicone compound (1,1,3,3,5,5,7,7-octamethyl tetrasiloxane) and 2.0 parts of toluene at room temperature in about 60 minutes while stirring followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.41 parts of the target silicone compound a-M10.

Figure 3K:
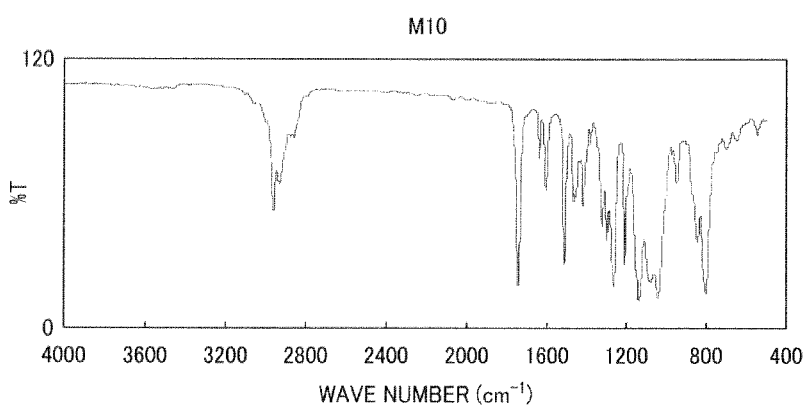
FIG. 3K is a graph illustrating an infrared absorption spectrum of a silicone compound a-M10.

The infra-red absorption spectrum graph is shown as FIG. 3K.

Synthesis Example a-V-3

Synthesis of Silicone Compound: 1=1 in the Chemical structure 5

Drip 4.68 parts of the compound a-IV (3-methoxy-4-methacryloxy aryl benzene), 0.009 parts of a stabilizer (2,6-di-t-butyl-4-methylphenol), 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of methyl hydrogen silicone compound (1,1,3,3,5,5,-hexamethyl trisiloxane) and 2.0 parts of toluene at room temperature in about 60 minutes while stirring followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.86 parts of the target silicone compound a-M11.

Figure 3L:
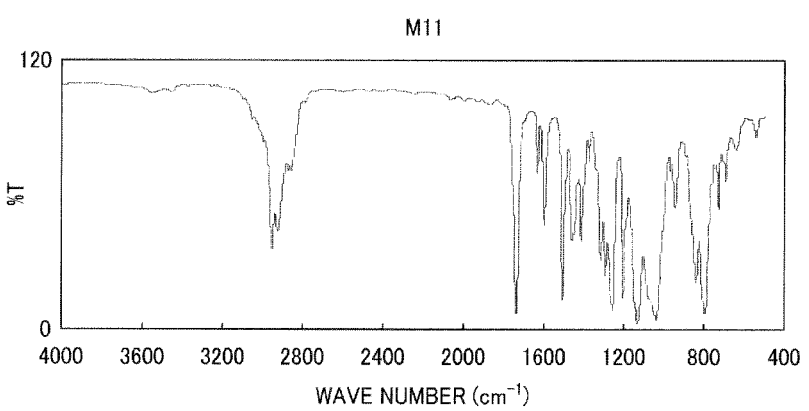
FIG. 3L is a graph illustrating an infrared absorption spectrum of a silicone compound a-Mil.

The infra-red absorption spectrum graph is shown as FIG. 3L.

Synthesis Example a-V-4

Synthesis of Silicone Compound: 1=m=n=0, X1=CH$_3$, X3=3-(3-methoxy-4-methacyloxyphenyl)propyl group in the Chemical Structure 1

Drip 4.11 parts of the compound a-IV (3-methoxy-4-methacryloxy arylbenzene), 0.007 parts of a stabilizer (2,6-di-t-butyl-4-methylphenol), 10 parts of toluene, and 0.032 parts of xylene solution of 2% by weight platinum/1,3-divinyl-1,1,3,3-tetramethyl disiloxane complex (manufactured by Sigma-Aldrich Co.) to a solution of 2.5 parts of methyl hydrogen silicone compound (pentamethyl disiloxane) and 2.5 parts of toluene at room temperature in about 60 minutes while stirring followed by reaction one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.99 parts of the target silicone compound a-M12.

Figure 3M:
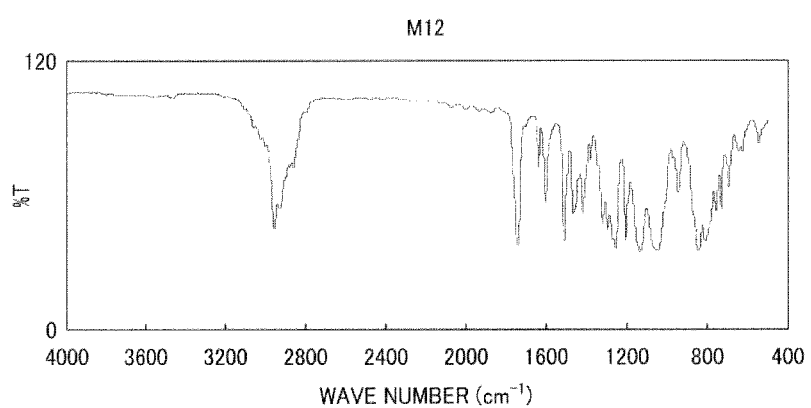
FIG. 3M is a graph illustrating an infrared absorption spectrum of a silicone compound a-M12.

The infra-red absorption spectrum graph is shown as FIG. 3M.

Synthesis of Silicone Compound: 1 and m are nearly equal to 6, n=0 in the Chemical structure 4 Drip 3.76 parts of the compound a-IV (3-methoxy-4-methacryloxy arylbenzene), 0.007 parts of a stabilizer (2,6-di-t-butyl-4-methylphenol), 10 parts of toluene, and 0.029 parts of xylene solution of 2% by weight platinum/1,3-divinyl-1,1,3,3-tetramethyl disiloxane complex (manufactured by Sigma-Aldrich Co.) to a solution of 2.5 parts of methyl hydrogen silicone compound: copolymers of ([poly[dimethylsilicone/methylhydrosilicone (mol ratio: 50%, molecular weight: up to 950) and 2.5 parts of toluene at room temperature in about 60 minutes while stirring followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.49 parts of the target silicone compound a-M13.

Figure 3N:
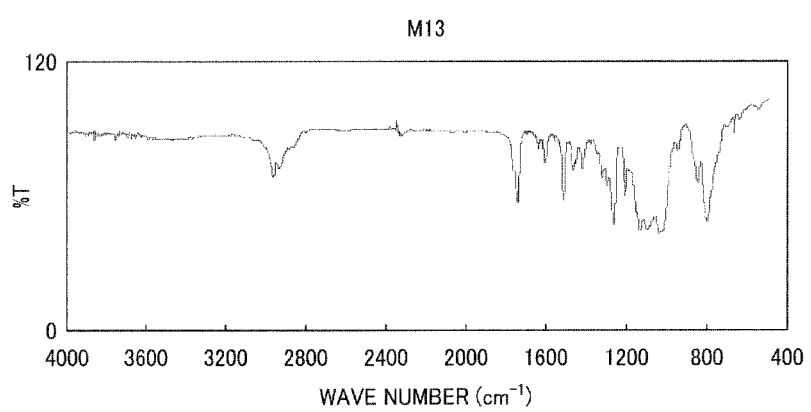
FIG. 3N is a graph illustrating an infrared absorption spectrum of a silicone compound a-M13.

The infra-red absorption spectrum graph is shown as FIG. 3N.

Examples a-1

Place 0.5 parts of the coloring resin particle (α), 4.28 parts of the silicone compound (a-M3), and 0.22 parts of silicone oil compound having an epoxy group (3-glycidoxy propyl) bis(trimethylsiloxy)methylsilane, which is equivalent to the acid value of the coloring resin particles (α) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink a-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Examples a-2

The photocurable liquid ink (a-2) is obtained in the same manner as in Example a-1 except that 0.14 parts of a long-chain alkyl compound having an epoxy group (2-ethylhexyl glycidyl ether), which is 1.2 times the equivalent to the acid value of the coloring resin particles (α) is used instead of the silicone oil compound having an epoxy group.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Examples a-3

Place 0.5 parts of the coloring resin particle (α), 4.28 parts of the silicone compound (a-M5), and 0.32 parts of a silicone oil compound having an epoxy group (3-glycidoxy propyl) bis(trimethylsiloxy)methylsilane), which is 1.5 times the equivalent to the acid value of the coloring resin particles (α) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink 3.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Examples a-4

The photocurable liquid ink (a-4) is obtained in the same manner as in Example a-1 except that 0.14 parts of a long-chain alkyl compound having an epoxy group (2-ethylhexyl glycidyl ether), which is 1.8 times the equivalent to the acid value of the coloring resin particles (α) is used instead of the silicone oil compound having an epoxy group.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Examples a-5

Place 0.5 parts of the coloring resin particle (α), 4.28 parts of the silicone compound (a-M9), and 0.22 parts of a silicone oil compound having an epoxy group (3-glycidoxy propyl) bis(trimethylsiloxy)methylsilane, which is the equivalent to the acid value of the coloring resin particles (α) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink a-5.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Examples a-6

Place 0.5 parts of the coloring resin particle (α), 4.28 parts of the silicone compound (a-M10), and 0.24 parts of a silicone oil compound having an epoxy group (3-glycidoxy propyl) bis(trimethylsiloxy)methylsilane, which is 1.2 times the equivalent to the acid value of the coloring resin particles (α) in a beaker followed by a two-hour dispersion by an ultrasonic dispersion device (output: 130 w, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink a-6.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example a-7

Place 0.5 parts of the coloring resin particle (α), 4.28 parts of the silicone compound (a-M11), and 0.24 parts of a silicone oil compound having an epoxy group (3-glycidoxy propyl) bis(trimethylsiloxy)methylsilane, which is 1.2 times the equivalent to the acid value of the coloring resin particles (α) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink a-7.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example a-8

Place 0.5 parts of the coloring resin particle (α), 4.28 parts of the silicone compound (a-M12), and 0.24 parts of a silicone oil compound having an epoxy group (3-glycidoxy propyl) bis(trimethylsiloxy)methylsilane, manufactured by Tokyo Chemical Industry Co., Ltd., which is 1.2 times the equivalent to the acid value of the coloring resin particles (α) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink a-8.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Examples a-9 to a-12

The photocurable liquid inks a-9, a-10, a-11, and a-12 are manufactured in the same manner as in Example a-1 except that the silicone compound a-M3 is changed to the silicone compounds a-M1, a-M2, a-M4, and a-M7, respectively. These inks have an excellent preservation stability.

Example a-13

Place 0.5 parts of the toner particles (β) and 4.28 parts of the silicone compound (a-M3) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a photocurable liquid ink.

Furthermore, add 1.0 part of polyether modified silicone oil (KF-945) manufactured by Shin-Etsu Chemical Co., Ltd.) followed by ultrasonic dispersion again to obtain a photocurable liquid ink a-13. The volume average particle diameter of the ink is 0.30 μm and the relative standard deviation (CV value) is 160%.

After the ink is preserved for 20 days, no agglomeration is observed. That is, the ink has an excellent preservation stability.

Comparative Example 1

Manufacturing of Liquid Ink Using Non-Curable Type Silicone Oil Compound

Place 0.5 parts of the toner particles (β) and 4.5 parts of the non-curable dimethyl siloxane SH200 (Viscosity: 20 mPa·s, manufactured by Dow Corning Toray) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a liquid ink, in which dispersion is not good.

Furthermore, add 1.0 part of polyether modified silicone oil (KF-945, manufactured by Shin-Etsu Chemical Co., Ltd.) followed by ultrasonic dispersion again to obtain a liquid ink 1. The volume average particle diameter of the ink is 0.52 μm and the relative standard deviation (CV value) is 280%.

After the ink is preserved for 20 days, agglomeration is observed so that the ink is re-dispersed, resulting in poor dispersion again.

Comparative Example 2

Manufacturing of Liquid Ink Using Commercially Available Curable Type Silicone Oil Compound Place 0.5 parts of the toner particles (β) and 4.5 parts of a commercially available curable type silicone compound (X-22-164, manufactured by Shin-Etsu Chemical Co., Ltd.) in a beaker followed by a two-hour dispersion by an ultrasonic dispersion device (output: 130 W, frequency: 20 kHz, pulser system) and add 0.2 parts of 15% by weight of zirconium octylate (manufactured by NIHON KAGAKU SANGYO CO., LTD.) to the liquid dispersion to obtain a liquid ink, in which dispersion is not good.

Furthermore, add 1.0 part of polyether modified silicone oil (KF-945, manufactured by Shin-Etsu Chemical Co., Ltd.) followed by ultrasonic dispersion again to obtain a liquid ink 2. The volume average particle diameter of the ink is 0.40 μm and the relative standard deviation (CV value) is 90%.

After the ink is preserved for 20 days, agglomeration is observed so that the ink is re-dispersed, resulting in poor dispersion again.

Inks of Examples a-1 to a-13 and Comparative Examples 1 and 2 are evaluated in the following evaluation tests 1 to 3.

Evaluation Test 1

Evaluation on Photocurability

Add 5.0 parts of a photopolymerization initiator (IRGACURE 907, manufactured by IRGACURE available from BASF) to each ink of Examples a-1 to a-13 and Comparative Examples 1 and 2 and evaluate the curability by viscoelasticity by curing energy.

The results are shown in Table 1-1. The less the curing energy, the higher the curing speed.

TABLE 1-1

| | Curing energy (mJ/cm$^2$) |
|---|---|
| Example a-1 (Liquid ink a-1) | 950 |
| Example a-2 (Liquid ink a-2) | 920 |
| Example a-3 (Liquid ink a-3) | 520 |
| Example a-4 (Liquid ink a-4) | 580 |
| Example a-5 (Liquid ink a-5) | 262 |
| Example a-6 (Liquid ink a-6) | 226 |
| Example a-7 (Liquid ink a-7) | 214 |
| Example a-8 (Liquid ink a-8) | 405 |
| Example a-9 (Liquid ink a-9) | 990 |
| Example a-10 (Liquid ink a-10) | 850 |
| Example a-11 (Liquid ink a-11) | 1020 |
| Example a-12 (Liquid ink a-12) | 970 |
| Example a-13 (Liquid ink a-13) | 1100 |
| Comparative Example 2 | 1240 |

Evaluation Test 2

Image Evaluation By Electrophotographic Image Forming Apparatus

Using each ink of Examples a-1 to a-13 and Comparative Examples 1 and 2, the image definition of the developed images on the image bearing member formed by the image forming apparatus illustrated in FIG. 1 is evaluated by naked eyes.

The criteria are as follows.

The results are shown in Table 1-2.

Evaluation Criteria

G: Good

B: Bad

TABLE 1-2

| | Definition |
|---|---|
| Example a-1 (Liquid ink a-1) | G |
| Example a-2 (Liquid ink a-2) | G |
| Example a-3 (Liquid ink a-3) | G |
| Example a-4 (Liquid ink a-4) | G |
| Example a-5 (Liquid ink a-5) | G |
| Example a-6 (Liquid ink a-6) | G |
| Example a-7 (Liquid ink a-7) | G |
| Example a-8 (Liquid ink a-8) | G |
| Example a-9 (Liquid ink a-9) | G |
| Example a-10 (Liquid ink a-10) | G |
| Example a-11 (Liquid ink a-11) | G |
| Example a-12 (Liquid ink a-12) | G |
| Example a-13 (Liquid ink a-13) | G |
| Comparative Example 1 | B |
| Comparative Example 2 | B |

Evaluation Test 3
Image Evaluation By Inkjet

Using each ink of Examples a-1 to a-13 and Comparative Examples 1 and 2, the image definition of the developed images on the image bearing member formed by an inkjet printer (IPSiO GX5000, manufactured by Ricoh Co., Ltd.) is evaluated by naked eyes.

The criteria are as follows.
The results are shown in Table 1-3.
Evaluation Criteria
  G: Good
  B: Bad

TABLE 1-3

| | Definition |
|---|---|
| Example a-1 (Liquid ink a-1) | G |
| Example a-2 (Liquid ink a-2) | G |
| Example a-3 (Liquid ink a-3) | G |
| Example a-4 (Liquid ink a-4) | G |
| Example a-5 (Liquid ink a-5) | G |
| Example a-6 (Liquid ink a-6) | G |
| Example a-7 (Liquid ink a-7) | G |
| Example a-8 (Liquid ink a-8) | G |
| Example a-9 (Liquid ink a-9) | G |
| Example a-10 (Liquid ink a-10) | G |
| Example a-11 (Liquid ink a-11) | G |
| Example a-12 (Liquid ink a-12) | G |
| Example a-13 (Liquid ink a-13) | G |
| Comparative Example 1 | B |
| Comparative Example 2 | B |

Synthesis Example b-II

Synthesis of Alkenyl Body of Substituent A-2: $R2=CH_2$, R3=Simple Bonding, and Ortho-Substituent Compound Place 17.82 parts of 2-hydroxy benzoic acid aryl ester, 10.33 parts of methacrylic acid (manufactured by Tokyo Chemical Industry Co., Ltd.), 1.22 parts of dimethylamino pyridine (manufactured by Tokyo Chemical Industry Co., Ltd.), and 180 parts of toluene in a container equipped with a stirrer, a thermometer, and a dripping funnel and drip 15.14 parts of diisopropyl carbodiimide (manufactured by Tokyo Chemical Industry Co., Ltd.) in about 30 minutes to obtain a reaction product while stirring at room temperature followed by six-hour stirring at room temperature to obtain a reactant.

Next, condense the reactant to about a half by volume followed by silica gel chromatography using toluene as a developing solvent to obtain 22.53 parts of 2-methachloxy benzoate aryl ester (Compound b-II).

Figure 4A:
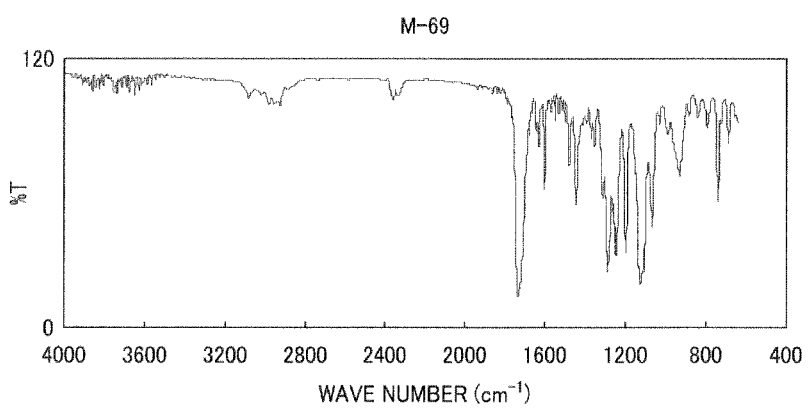
FIG. 4A is a graph illustrating an infrared absorption spectrum of a compound b-II.

The infra-red absorption spectrum graph is shown as FIG. 4A.

Synthesis Example b-III

Synthesis of Alkenyl Body of Substituent A-2: $R2=CH_2$, R3=Simple Bonding, and Metha-Substituent Compound 23.44 parts of the target product (Compound b-III: 3-methacloxy benzoate aryl ester) is obtained in the same manner as in Synthesis Example b-II except that, instead of 17.82 parts of 2-hydroxybenzoate aryl ester, 17.82 parts of 3-hydroxy benzoate aryl ester is used.

Figure 4B:
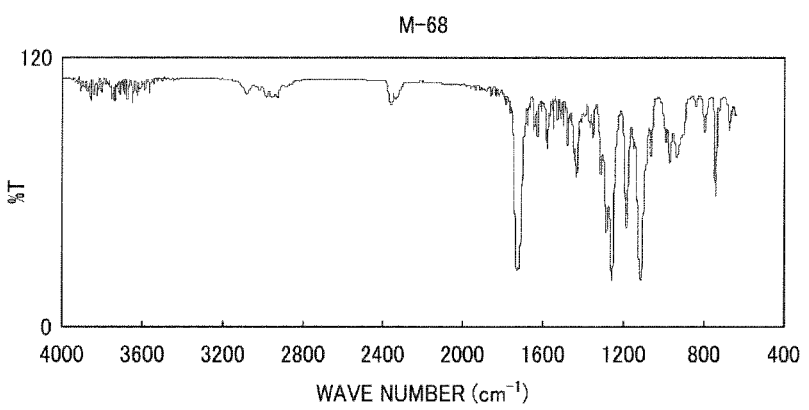
FIG. 4B is a graph illustrating an infrared absorption spectrum of a compound b-III.

The infra-red absorption spectrum graph is shown as FIG. 4B.

Synthesis Example b-IV

Synthesis of Alkenyl Body of Substituent A-2: $R2=CH_2$, R3=Simple Bonding, and Para-Substituent Compound 24.16 parts of the target product (Compound b-IV: 4-methacloxy benzoate aryl ester) is obtained in the same manner as in Synthesis Example b-II except that, instead of 17.82 parts of 2-hydroxybenzoate aryl ester, 17.82 parts of 3-hydroxybenzoate aryl ester is used.

Figure 4C:
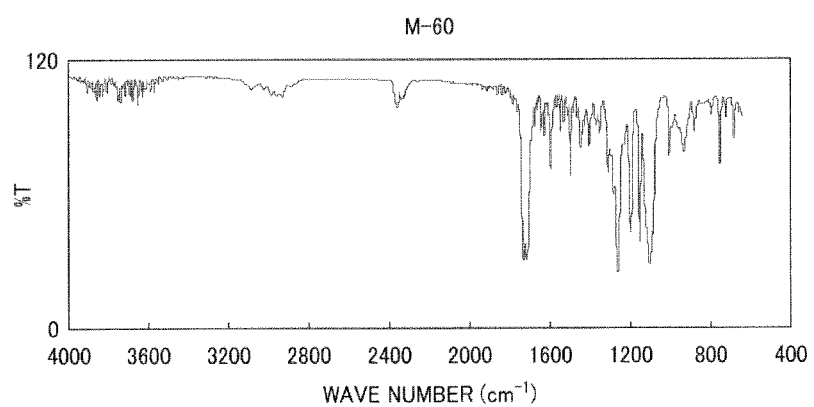
FIG. 4C is a graph illustrating an infrared absorption spectrum of a compound b-IV.

The infra-red absorption spectrum graph is shown as FIG. 4C.

Synthesis Example b-V

Synthesis of Alkenyl Body of Substituent A-2: $R2=CH_2$, $R3=OCH_2CH_2$, and Ortho-Substituent Compound 26.52 parts of the target product (Compound b-V: 2-methacryloxy benzoate (2-aryloxy)ethyl ester) is obtained in the same manner as in Synthesis Example b-II except that, instead of 17.82 parts of 2-hydroxy benzoate aryl ester, 22.02 parts of 2-hydroxy benzoate (2-aryloxy)ethyl ester is used.

Figure 4D:
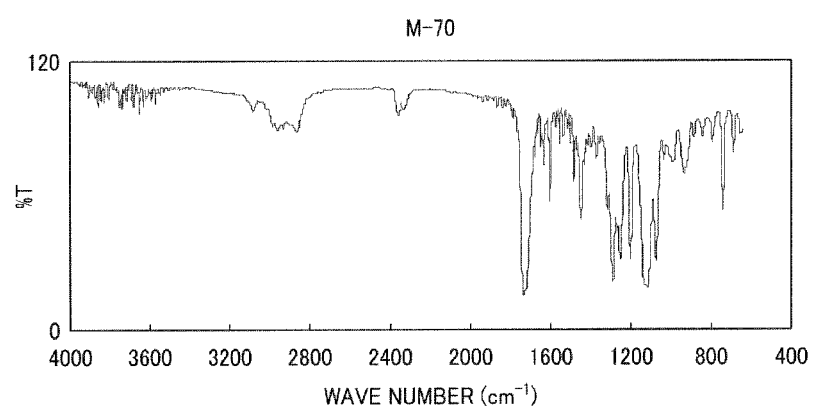
FIG. 4D is a graph illustrating an infrared absorption spectrum of a compound b-V.

The infra-red absorption spectrum graph is shown as FIG. 4D.

Synthesis Example b-VI

Synthesis of Alkenyl Body of Substituent A-2: $R2=CH_2$, $R3=OCH_2CH_2$, and Metha-Substituent Compound 28.37 parts of the Target Product (Compound b-VI: 3-methacryloxy benzoate (2-aryloxy)ethyl ester) is Obtained in the Same Manner as in Synthesis Example b-II Except that, Instead of 17.82 parts of 2-hydroxy benzoate aryl ester, 22.02 Parts of 3-hydroxy benzoate (2-aryloxy) ethyl ester is used.

Figure 4E:
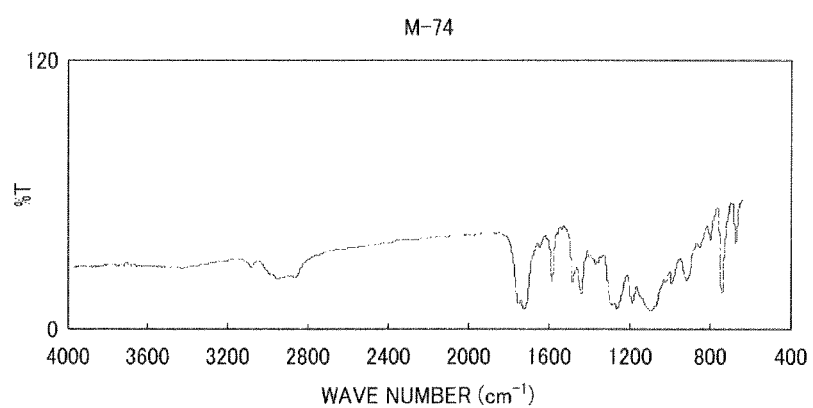
FIG. 4E is a graph illustrating an infrared absorption spectrum of a compound b-VI.

The infra-red absorption spectrum graph is shown as FIG. 4E.

Synthesis Example b-VII-1

Synthesis of Silicone Compound: 1 is nearly equal to 6, m=n=0, X1=X3=Substituent A-2 in the Chemical Structure 1, $R2=CH_2$, R3=Simple Bonding, and Ortho-subtituent in Substituent A-2

Drip 3.40 parts of the compound b-II (2-methacyloxybenzoate aryl ester, 10 parts of toluene, and 0.026 parts of xylene solution of 2% by weight platinum/1,3-divinyl-1,1,3,3-tetramethyl disiloxane complex (manufactured by Sigma-Aldrich Co.) to a solution of 4.0 parts of silicone compound: ([poly[dimethylsilicone having both ends terminated with hydrogen atoms (molecular weight: up to 580, manufactured by Sigma-Aldrich Co.) and 4 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 7.57 parts of the target silicone compound b-M1.

Figure 4F:
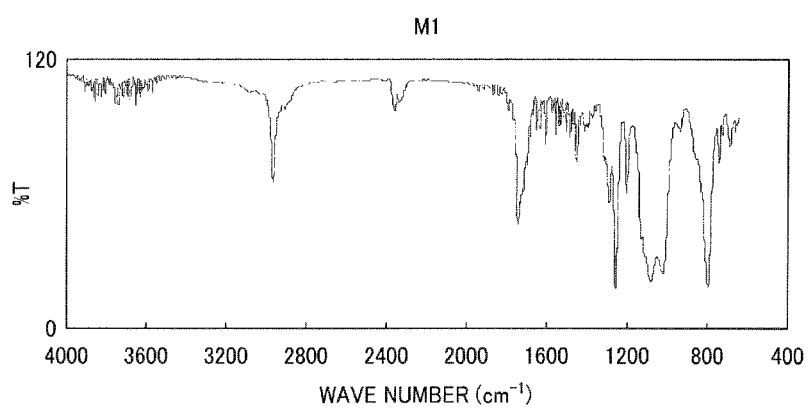
FIG. 4F is a graph illustrating an infrared absorption spectrum of a silicone compound b-M1.

The infra-red absorption spectrum graph is shown as FIG. 4F.

Synthesis Example b-VII-2

Synthesis of Silicone Compound: l=1, m=n=0, X1=X3=Substituent A-2 in the Chemical Structure 1, R2=CH$_2$, R3=Simple Bonding, and Ortho-subtituent in Substituent A-2

Figure 4G:
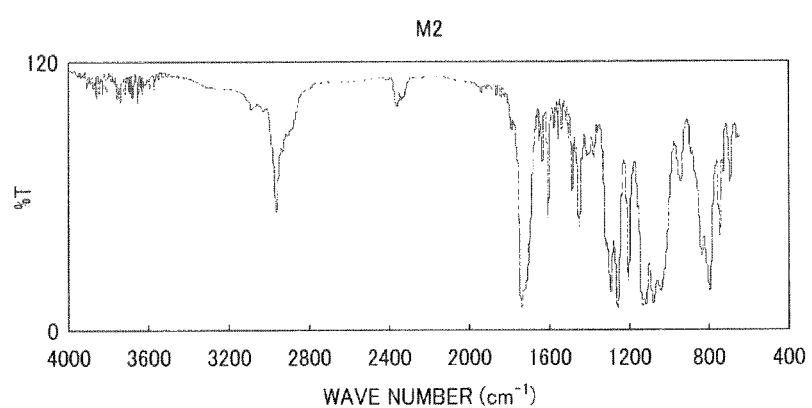
FIG. 4G is a graph illustrating an infrared absorption spectrum of a silicone compound b-M2.

Drip 2 parts of the compound b-II (2-methacyloxy-benzoate aryl ester, 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5-hexamethyltrisiloxane (manufactured by Sigma-Aldrich Co.) and 2.0 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 8.24 parts of the target silicone compound b-M2. The infra-red absorption spectrum graph is shown as FIG. 4G

Synthesis Example b-VII-3

Synthesis of Silicone Compound: l=n=0, m=1 in the Chemical Structure 2, Ortho-subtituent in Substituent B-2

Figure 4H:
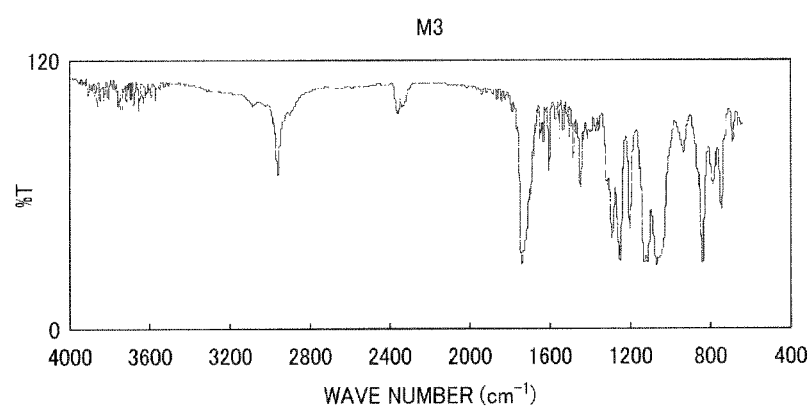
FIG. 4H is a graph illustrating an infrared absorption spectrum of a silicone compound b-M3.

Drip 2.77 parts of the Compound b-II (2-methacyloxy-benzoate aryl ester, 10 parts of toluene, and 0.021 parts of xylene solution of 2% by weight platinum/1,3-divinyl-1,1,3,3-tetramethyl disiloxane complex (manufactured by Sigma-Aldrich Co.) to a solution of 2.5 parts of silicone compound: (1,1,1,3,5,5,5-heptamethyl trisiloxane (manufactured by Tokyo Chemical Industry Co., Ltd.) and 2.5 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.25 parts of the target silicone compound b-M3. The infra-red absorption spectrum graph is shown as FIG. 4H.

Synthesis Example b-VII-4

Synthesis of Silicone Compound: 1 is Nearly Equal to 6, m is Nearly Equal to 3, n is Nearly Equal to 3, Metha-substitutene in the Substituent B-2, Y=Phenoxypropyl Group, in the Chemical Structure 2

Drip 2.28 parts of the Compound b-III (3-methacyloxy-benzoate aryl ester, 10 parts of arylphenyl ether (manufactured by Tokyo Chemical Industry Co., Ltd.), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydrosiloxane with ends terminated by trimethyl silyl) (mol ratio: 50%, manufactured by Sigma-Aldrich Co.), and 3.0 parts of toluene in about 60 minutes while stirring at a room temperature followed by reaction under the same condition one night.

Figure 4I:
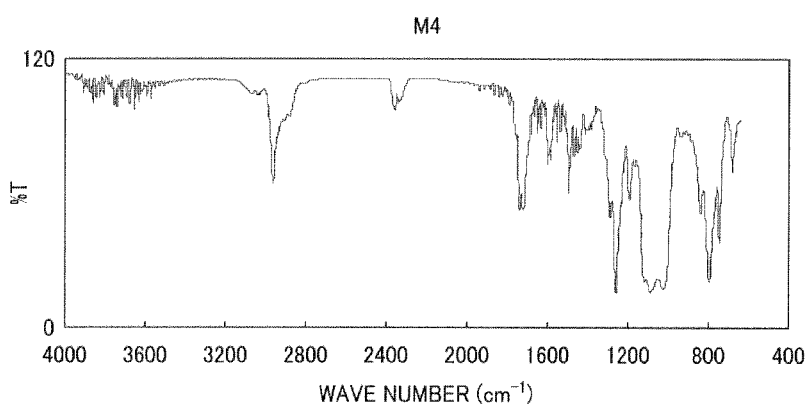
FIG. 4I is a graph illustrating an infrared absorption spectrum of a silicone compound b-M4.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.86 parts of the target silicone compound b-M4. The infra-red absorption spectrum graph is shown as FIG. 4I.

Synthesis Example b-VII-5

Synthesis of Silicone Compound: 1 is Nearly Equal to 6, m=n=0, X1=X3=Substituent A-2 in the Chemical Structure 1, R2=CH$_2$, R3=Simple Bonding, and Metha-Subtituent in Substituent A-2

Drip 4.24 parts of the compound b-III (3-methacyloxy-benzoate aryl ester, 10 parts of toluene, and 0.033 parts of xylene solution of 2% by weight platinum/1,3-divinyl-1,1,3,3-tetramethyl disiloxane complex (manufactured by Sigma-Aldrich Co.) to a solution of 5.0 parts of silicone compound: (polydimethyl silicone with ends terminated with hydrogen atom (molecular weight: up to 580, manufactured by Sigma-Aldrich Co.) and 5 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 9.23 parts of the target silicone compound b-M5.

Figure 4J:
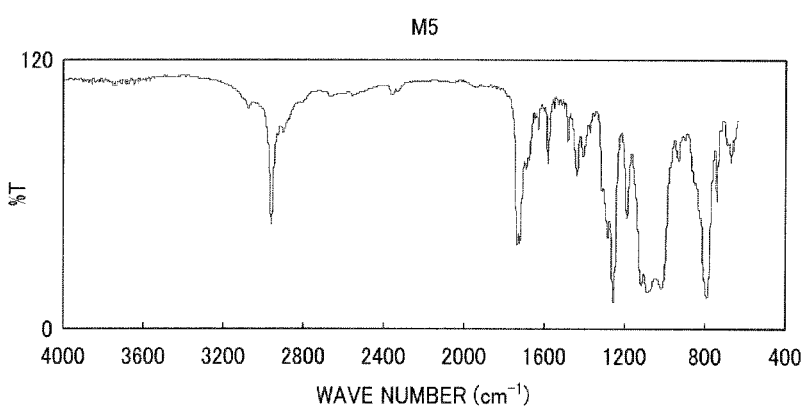
FIG. 4J is a graph illustrating an infrared absorption spectrum of a silicone compound b-M5.

The infra-red absorption spectrum graph is shown as FIG. 4J.

Synthesis Example b-VII-6

Synthesis of Silicone Compound: l=1, m=n=0, X1=X3=Substituent A-2 in the Chemical Structure 1, R2=CH$_2$, R3=Simple Bonding, and Metha-Subtituent in the Substituent A-2

Drip 7.09 parts of the compound b-III (3-methacyloxy-benzoate aryl ester), 10 parts of toluene, and 0.055 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,3,3,5,5-hexamethyltrisiloxane (manufactured by Sigma-Aldrich Co.) and 3.0 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 9.98 parts of the target silicone compound b-M6.

Figure 4K:
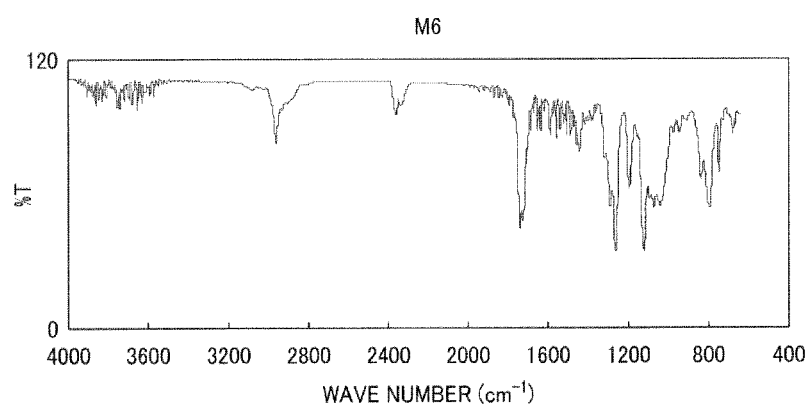
FIG. 4K is a graph illustrating an infrared absorption spectrum of a silicone compound b-M6.

The infra-red absorption spectrum graph is shown as FIG. 4K.

Synthesis Example b-VII-7

Synthesis of Silicone Compound: l=m=n=0, X1=X3=Substituent A-2 in the Chemical Structure 1, R2=CH$_2$, R3=Simple Bonding, and Metha-subtituent in the Substituent A-2

Drip 7.33 parts of the Compound b-III (3-methacyloxy-benzoate aryl ester), 10 parts of toluene, and 0.057 parts of xylene solution of 2% by weight platinum/1,3-divinyl-1,1,3, 3-tetramethyl disiloxane complex (manufactured by Sigma-Aldrich Co.) to a solution of 2.0 parts of silicone compound: (1,1,3,3-tetramethyl trisiloxane (manufactured by Tokyo Chemical Industry Co., Ltd.) and 2.0 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 7.66 parts of the target silicone compound b-M7.

Figure 4L:
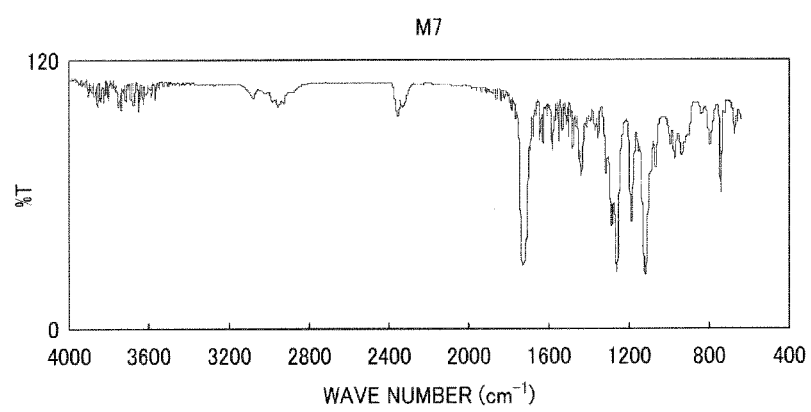
FIG. 4L is a graph illustrating an infrared absorption spectrum of a silicone compound b-M7.

The infra-red absorption spectrum graph is shown as FIG. 4L.

Synthesis Example b-VII-8

Synthesis of Silicone Compound: 1=n=0, m=1, Metha-substituent in Substituent B-2 in the Chemical Structure 2

Drip 4.43 parts of the Compound b-III (3-methacyloxybenzoate aryl ester, 10 parts of toluene, and 0.034 parts of xylene solution of 2% by weight platinum/1,3-divinyl-1,1,3,3-tetramethyl disiloxane complex (manufactured by Sigma-Aldrich Co.) to a solution of 4.0 parts of silicone compound: (1,1,1,3,5,5,5-heptamethyl trisiloxane (manufactured by Tokyo Chemical Industry Co., Ltd.) and 4.0 parts of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (21555 cm$^{-1}$ of Si—H in infra-red absorption spectrum to obtain 8.08 parts of the target silicone compound b-M8.

Figure 4M:
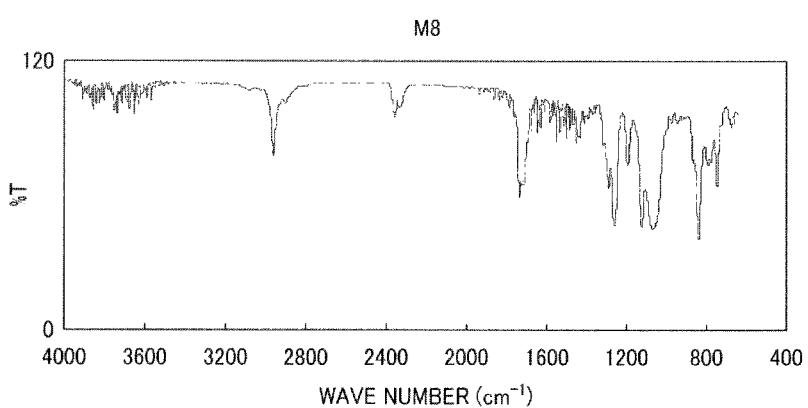
FIG. 4M is a graph illustrating an infrared absorption spectrum of a silicone compound b-M8.

The infra-red absorption spectrum graph is shown as FIG. 4M

Synthesis Example b-VII-9

Synthesis of Silicone Compound: 1 is Nearly Equal to 6, m is Nearly Equal to 3, n is Nearly Equal to 3, Para-Substituent in Substituent B-2, and Y=phenoxypropyl Group in the Chemical Structure 2

Drip 2.28 parts of the Compound b-IV (4-methacyloxybenzoate aryl ester, 1.30 parts of arylphenyl ether (manufactured by Tokyo Chemical Industry Co., Ltd.), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydrosiloxane with ends terminated by trimethyl silyl) (mol ratio: 50%, manufactured by Sigma-Aldrich Co.), and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.64 parts of the target silicone compound b-M9.

Figure 4N:
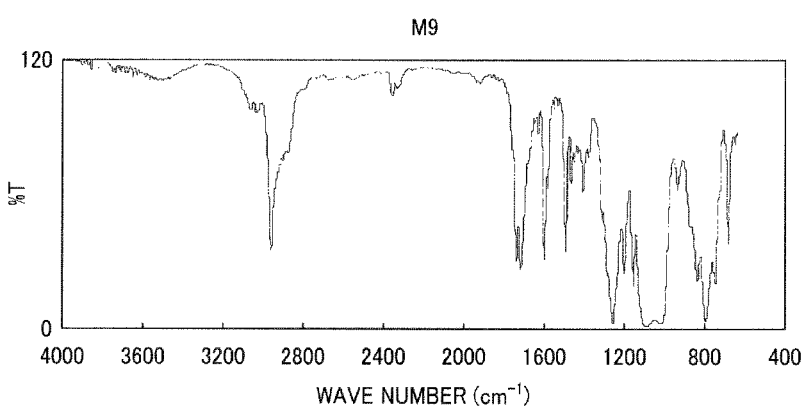
FIG. 4N is a graph illustrating an infrared absorption spectrum of a silicone compound b-M9.

The infra-red absorption spectrum graph is shown as FIG. 4N.

Synthesis Example b-VII-10

Synthesis of Silicone Compound: 1=1, m=n=0, X1=X3=Substituent A-2 in the Chemical Structure 1, R2=CH$_2$, R3=Simple Bonding and Para-subtituent in the Substituent A-2

Drip 7.44 parts of the compound b-IV (4-methacyloxybenzoate aryl ester), 10 parts of toluene, and 0.055 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,3,3,5,5-hexamethyl trisiloxane (manufactured by Sigma-Aldrich Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 01 mmHg at 40° C. and confirm disappearance of absorption (2155 cm$^{-1}$ of Si—H in infra-red absorption spectrum to obtain 10.23 parts of the target silicone compound b-M10.

Figure 4O:
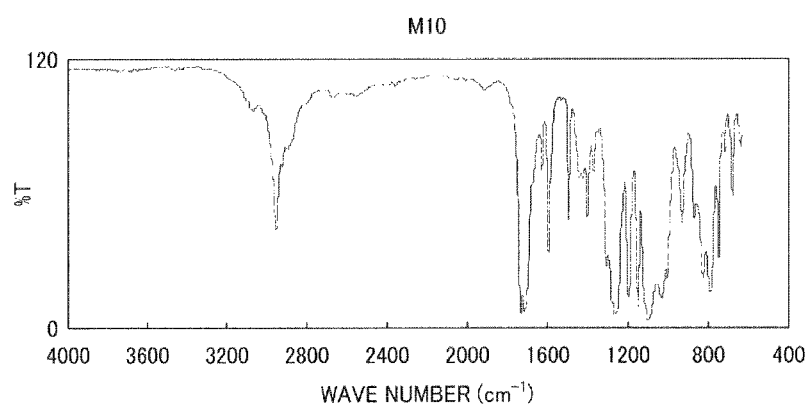
FIG. 4O is a graph illustrating an infrared absorption spectrum of a silicone compound b-M10.

The infra-red absorption spectrum graph is shown as FIG. 4O.

Synthesis Example b-VII-11

Synthesis of Silicone Compound: 1=n=0, m=1 in the Chemical Structure 2, Metha-subtituent in the Substituent A-2

Drip 4.65 parts of the Compound b-IV (4-methacyloxybenzoate aryl ester, 10 parts of toluene, and 0.034 parts of xylene solution of 2% by weight platinum/1,3-divinyl-1,1,3,3-tetramethyl disiloxane complex (manufactured by Sigma-Aldrich Co.) to a solution of 4.0 parts of silicone compound: (1,1,1,3,5,5,5-heptamethyl trisiloxane (manufactured by Tokyo Chemical Industry Co., Ltd.) and 4.0 parts of toluene in about 60 minutes while stirring at a room temperature followed by reaction under the same condition one night. Thereafter, distill away the solvent with a reduced pressure, conduct stripping treatment for two hours with a reduced pressure of 01 mmHg at 40° C. and confirm disappearance of absorption (2155 cm$^{-1}$ of Si—H in infra-red absorption spectrum to obtain 8.38 parts of the target silicone compound b-M11.

Figure 4P:
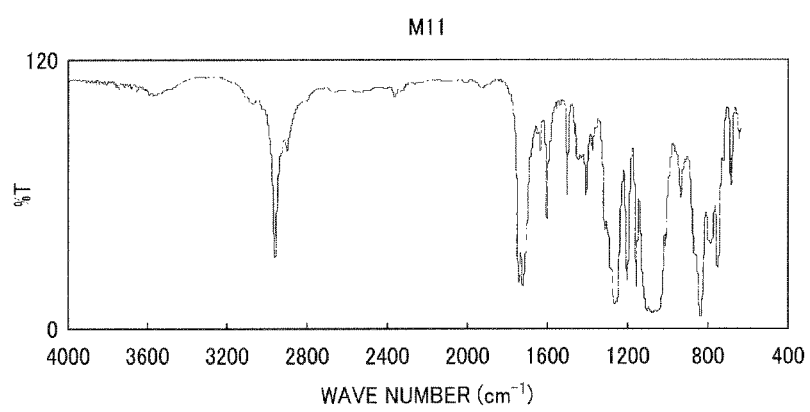
FIG. 4P is a graph illustrating an infrared absorption spectrum of a silicone compound b-M11.

The infra-red absorption spectrum graph is shown as FIG. 4P.

Synthesis Example b-VII-12

Synthesis of Silicone Compound: 1=1, m=n=0, X1=X3=Substituent A-2 in the Chemical Structure 1, R2=CH$_2$, R3=OCH$_2$CH$_2$, Ortho-subtituent in the Substituent A-2

Drip 5.81 parts of the compound b-V: {2-methacyloxybenzoate (2-aryloxy) ethyl ester}, 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5-hexamethyltrisiloxane (manufactured by Sigma-Aldrich Co.) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 7.35 parts of the target silicone compound b-M12.

Figure 4Q:
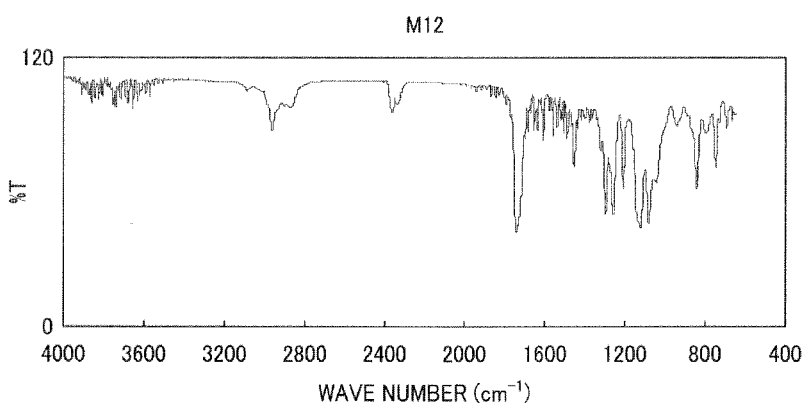
FIG. 4Q is a graph illustrating an infrared absorption spectrum of a silicone compound b-M12.

The infra-red absorption spectrum graph is shown as FIG. 4Q.

Synthesis Example b-VII-13

Synthesis of Silicone Compound: 1=m=n=0, X1=X3=Substituent A-2 in the Chemical Structure 1, R2=CH$_2$, R3=OCH$_2$CH$_2$ and Ortho-subtituent in Substituent A-2

Drip 4.51 parts of the compound b-V: {2-methacyloxybenzoate (2-aryloxy) ethyl ester}, 10 parts of toluene, and 0.028 parts of xylene solution of 2% by weight platinum/1,3-divinyl-1,1,3,3-tetramethyl disiloxane complex (manufactured by Sigma-Aldrich Co.) to a solution of 1.0 part of silicone compound: (1,1,3,3-tetramethyl trisiloxane (manufactured by Tokyo Chemical Industry Co., Ltd.) and 1.0 part of toluene in about 60 minutes while stirring at a room temperature followed by reaction under the same condition one night. Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.90 parts of the target silicone compound b-M13.

Figure 4R:
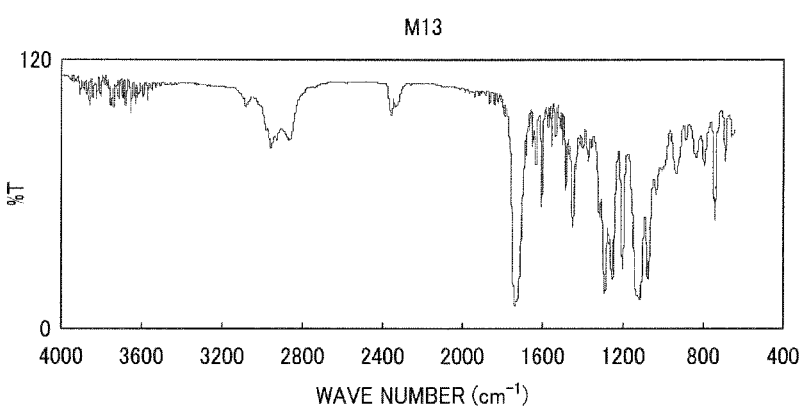
FIG. 4R is a graph illustrating an infrared absorption spectrum of a silicone compound b-M13.

The infra-red absorption spectrum graph is shown as FIG. 4R.

Synthesis Example b-VII-14

Synthesis of Silicone Compound: 1 is nearly equal to 6, m=n=0, X1=X3=Substituent A-2 in the Chemical Structure 1, R2=CH$_2$, R3=OCH$_2$CH$_2$, Metha-subtituent in the Substituent A-2

Drip 3.16 parts of the compound b-VI: {3-methacyloxy-benzoate (2-aryloxy) ethyl ester}, 10 parts of toluene, and 0.020 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (polydimethyl silicone with ends terminated with hydrogen atom (molecular weight: up to 580, manufactured by Sigma-Aldrich Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.95 parts of the target silicone compound b-M14.

Figure 4S:
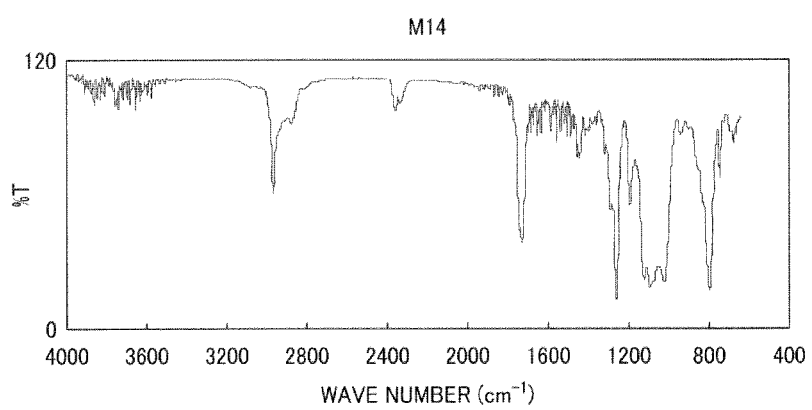
FIG. 4S is a graph illustrating an infrared absorption spectrum of a silicone compound b-M14.

The infra-red absorption spectrum graph is shown as FIG. 4S.

Synthesis Example b-VII-15

Synthesis of Silicone Compound: 1 is Nearly Equal to 4, m=n=0, X1=X3=Substituent A-2 in the Chemical Structure 1, R2=CH$_2$, R3=OCH$_2$CH$_2$, Metha-subtituent in the Substituent A-2

Drip 3.16 parts of the compound b-VI: {3-methacryloxy-benzoate (2-aryloxy) ethyl ester}, 10 parts of toluene, and 0.025 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (polydimethyl silicone with ends terminated with hydrogen atom (molecular weight: up to 500, manufactured by AZmax. Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.85 parts of the target silicone compound b-M15.

Figure 4T:
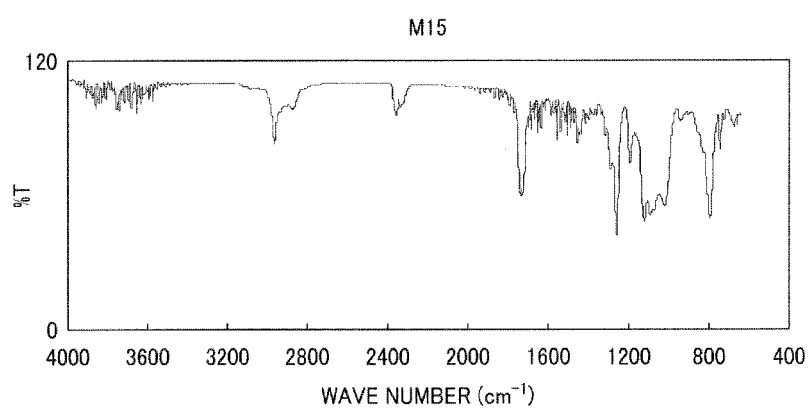
FIG. 4T is a graph illustrating an infrared absorption spectrum of a silicone compound b-M15.

The infra-red absorption spectrum graph is shown as FIG. 4T.

Synthesis Example b-VII-16

Synthesis of Silicone Compound: 1=m=n=0, X1=X3=Substituent A-2 in the Chemical Structure 1, R2=CH$_2$, R3=OCH$_2$CH$_2$, Metha-subtituent in the Substituent A-2

Drip 4.51 parts of the compound b-VI: {3-methacyloxy-benzoate (2-aryloxy) ethyl ester}, 10 parts of toluene, and 0.028 parts of xylene solution of 2% by weight platinum/1,3-divinyl-1,1,3,3-tetramethyl disiloxane complex (manufactured by Sigma-Aldrich Co.) to a solution of 1.0 part of silicone compound: (1,1,3,3-tetramethyl trisiloxane (manufactured by Tokyo Chemical Industry Co., Ltd.) and 1.0 part of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.72 parts of the target silicone compound b-M16.

Figure 4U:
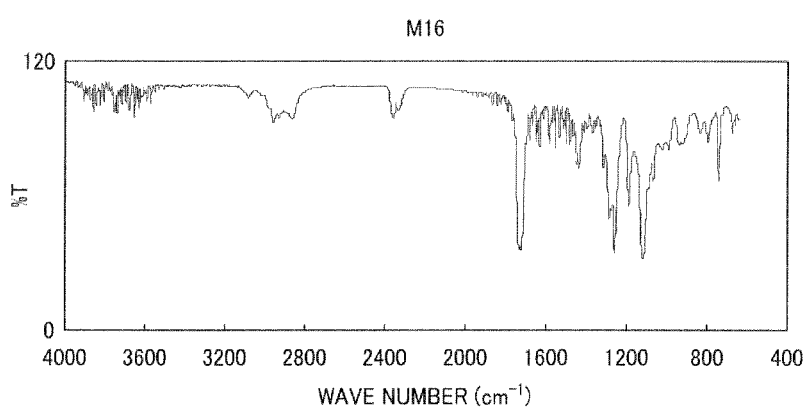
FIG. 4U is a graph illustrating an infrared absorption spectrum of a silicone compound b-M16.

The infra-red absorption spectrum graph is shown as FIG. 4U.

Example b-1

Place 1.0 part of the coloring resin particle (α), 18.56 parts of the silicone compound (b-M2), and 0.43 parts of silicone oil compound having an epoxy group (3-glycidoxy propyl (bis trimethylsiloxy)methylsilane)(manufactured by Tokyo Chemical Industry Co., Ltd.), which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example b-2

Place 1.0 part of the coloring resin particle (α), 18.76 parts of the silicone compound (b-M4), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-2.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-3

Place 1.0 part of the coloring resin particle (α), 18.71 parts of the silicone compound (b-M5), and 0.29 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-3.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-4

Place 1.0 part of the coloring resin particle (α), 18.71 parts of the silicone compound (b-M6), and 0.29 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-4.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-5

Place 1.0 part of the coloring resin particle (α), 18.71 parts of the silicone compound (b-M7), and 0.29 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-5.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-6

Place 1.0 part of the coloring resin particle (α), 18.76 parts of the silicone compound (b-M9), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-6.

The volume average particle diameter of the ink is 0.20 μm and the relative standard deviation (CV value) is 28%.

After the ink is preserved for 20 days, no agglomeration is observed and the volume average particle diameter is still 0.20 μm. That is, the ink has an excellent preservation stability.

Example b-7

Place 1.0 part of the coloring resin particle (α), 18.76 parts of the silicone compound (b-M10), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-7.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-8

Place 1.0 part of the coloring resin particle (α), 18.76 parts of the silicone compound (b-M13), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-8.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-9

Place 1.0 part of the coloring resin particle (α), 18.76 parts of the silicone compound (b-M14), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-9.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-10

Place 1.0 part of the coloring resin particle (α), 18.76 parts of the silicone compound (b-M15), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-10.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example b-11

Place 1.0 part of the coloring resin particle (α), 18.76 parts of the silicone compound (b-M16), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink b-11.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Inks of Examples b-1 to b-11 are evaluated in the same manner as in Those of Examples a-1 to a-13 by the evaluation tests 1 to 3.

The results are shown in Tables 2-1 to 2-3.

Evaluation Test 1
Evaluation on Photocurability

TABLE 2-1

|  | Curing energy (mJ/cm$^2$) |
| --- | --- |
| Example b-1 (Liquid ink b-1) | 450 |
| Example b-2 (Liquid ink b-2) | 180 |
| Example b-3 (Liquid ink b-3) | 360 |
| Example b-4 (Liquid ink b-4) | 250 |
| Example b-5 (Liquid ink b-5) | 640 |
| Example b-6 (Liquid ink b-6) | 750 |
| Example b-7 (Liquid ink b-7) | 180 |
| Example b-8 (Liquid ink b-8) | 910 |
| Example b-9 (Liquid ink b-9) | 505 |
| Example b-10 (Liquid ink b-10) | 500 |
| Example b-11 (Liquid ink b-11) | 670 |

Evaluation Test 2
Image Evaluation By Electrophotographic Image Forming Apparatus

TABLE 2-2

|  | Definition |
| --- | --- |
| Example b-1 (Liquid ink b-1) | G |
| Example b-2 (Liquid ink b-2) | G |
| Example b-3 (Liquid ink b-3) | G |
| Example b-4 (Liquid ink b-4) | G |
| Example b-5 (Liquid ink b-5) | G |
| Example b-6 (Liquid ink b-6) | G |
| Example b-7 (Liquid ink b-7) | G |
| Example b-8 (Liquid ink b-8) | G |
| Example b-9 (Liquid ink b-9) | G |
| Example b-10 (Liquid ink b-10) | G |
| Example b-11 (Liquid ink b-11) | G |

Evaluation Test 3
Results of Image Evaluation for Inkjet System

TABLE 2-3

|  | Definition |
| --- | --- |
| Example b-1 (Liquid ink b-1) | G |
| Example b-2 (Liquid ink b-2) | G |
| Example b-3 (Liquid ink b-3) | G |
| Example b-4 (Liquid ink b-4) | G |
| Example b-5 (Liquid ink b-5) | G |
| Example b-6 (Liquid ink b-6) | G |
| Example b-7 (Liquid ink b-7) | G |
| Example b-8 (Liquid ink b-8) | G |
| Example b-9 (Liquid ink b-9) | G |
| Example b-10 (Liquid ink b-10) | G |
| Example b-11 (Liquid ink b-11) | G |

Synthesis Example c-II

Synthesis of Alkenyl Body of Substituent A-3: $R2=CH_2$, R3=Single Bonding, 4-Substituent Place 35.84 parts of 4-hydroxy cyclohexane carbonate aryl ester, 18.08 parts of methacrylic acid (manufactured by Tokyo Chemical Industry Co., Ltd.), 2.44 parts of dimethylamino pyridine (manufactured by Tokyo Chemical Industry Co., Ltd.), and 250 parts of toluene in a container equipped with a stirrer, a thermometer, and dripping funnel and drip 18.08 part of diisopropyl carbodimide in about 30 minutes to the container while stirring followed by six-hour stirring at room temperature to obtain a reaction product.

Next, condense the filtrate in which diisopropyl urine is filtered from the reaction product to about a half by volume followed by silica gel chromatography using toluene as a developing solvent to obtain 31.97 parts of the target compound c-II (4-methachloxy cyclohexane carbonate aryl ester).

Figure 5A:
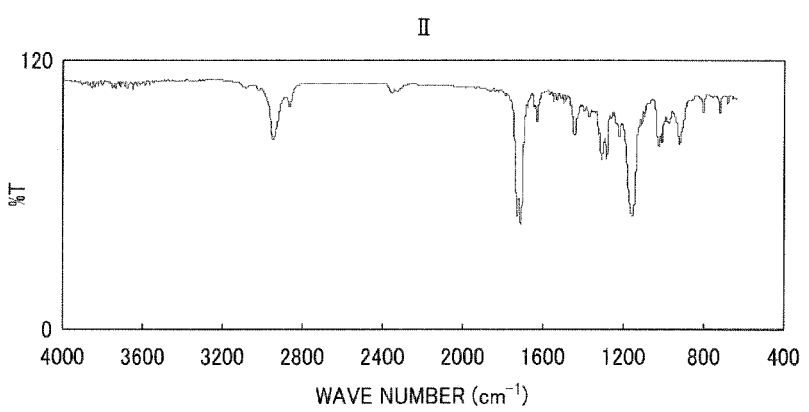
FIG. 5A is a graph illustrating an infrared absorption spectrum of a compound c-II.

The infra-red absorption spectrum graph is shown as FIG. 5A.

Synthesis Example c-III

Synthesis of Alkenyl Body of Substituent A-3: $R2=CH_2$, $R3=OCH_2CH_2$, 4-Substituent 42.79 parts of the target product (Compound c-III: 4-methacloxy cyclohexane carbonate (2-aryloxy) ethyl ester) is obtained in the same manner as in Synthesis Example c-II except that, instead of 35.84 parts of 4-hydroxycyclohexane carbonate aryl ester, 45.66 parts of 4-hydroxycyclohexane carbonate (2-aryloxy) ethyl ester is used.

Figure 5B:
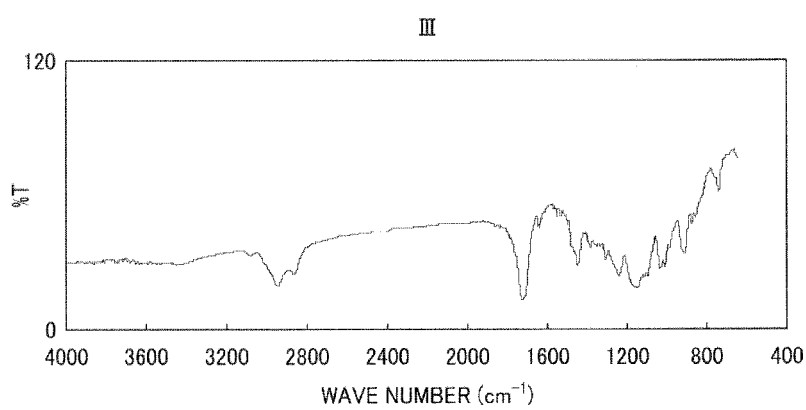
FIG. 5B is a graph illustrating an infrared absorption spectrum of a compound c-III.

The infra-red absorption spectrum graph is shown as FIG. 5B.

Synthesis Example c-IV-1

Synthesis of Silicone Compound: 1 is Nearly Equal to 6, m is Nearly Equal to 3, n=0 in the Chemical Structure 2

Drip 3.99 parts of the compound c-II: {4-methacryloxy-cyclohexane carbonate aryl ester, 10 parts of toluene, and 0.029 parts of xylene solution of 2% by weight platinum/1,3-divinyl-1,1,3,3-tetramethyl disiloxane complex (manufactured by Sigma-Aldrich Co.) to a solution of 2.5 parts of silicone compound: copolymer of poly(dimethyl siloxane-methylhydroxy siloxane with ends terminated by trimethyl silyl (mol ratio: 50%) and 4 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.26 parts of the target silicone compound c-M1.

Figure 5C:
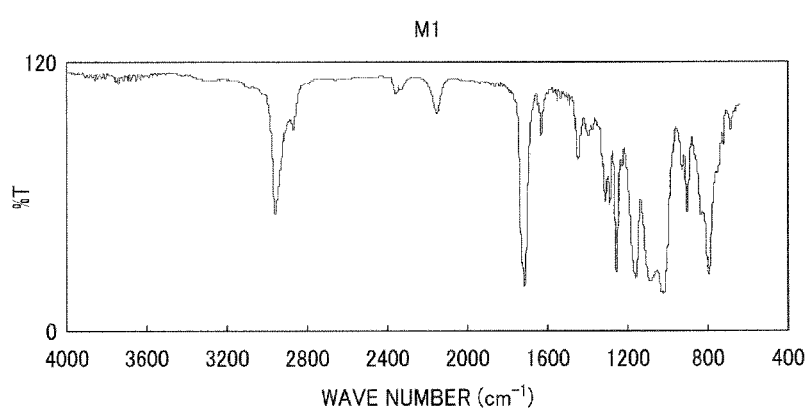
FIG. 5C is a graph illustrating an infrared absorption spectrum of a silicone compound c-M1.

The infra-red absorption spectrum graph is shown as FIG. 5C.

Synthesis Example c-IV-2

Synthesis of Silicone Compound: 1 is Nearly Equal to 6, m is Nearly Equal to 3, n is Nearly Equal to 3 and Y=phenoxypropyl in the Chemical Structure 2

Drip 1.90 parts of the compound c-II: {4-methacryloxy-cyclohexane carbonate aryl ester, 1.04 parts of arylphenyl ether (manufactured by Tokyo Chemical Industry Co., Ltd.), 10 parts of toluene, and 0.029 parts of xylene solution of 2% by weight platinum/1,3-divinyl-1,1,3,3-tetramethyl disiloxane complex (manufactured by Sigma-Aldrich Co.) to a solution of 2.5 parts of silicone compound: copolymer of poly(dimethyl siloxane-methylhydroxy siloxane with ends terminated by trimethyl silyl (mol ratio: 50%) and 4 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.40 parts of the target silicone compound c-M2.

Synthesis Example c-IV-3

Synthesis of Silicone Compound: 1=1, m=n=0, X1=X3=Substituent A-3 in the Chemical Structure 1, R2=CH$_2$, R3=single bonding, 4-subtituent in Substituent A-3

Drip 3.66 parts of the compound c-II: 4-methacyloxy cyclohexane carbonate aryl ester, 10 parts of toluene, and 0.027 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5,7,7-octamethyltetrasiloxane (manufactured by AZmax. Co) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.55 parts of the target silicone compound c-M3.

Figure 5D:
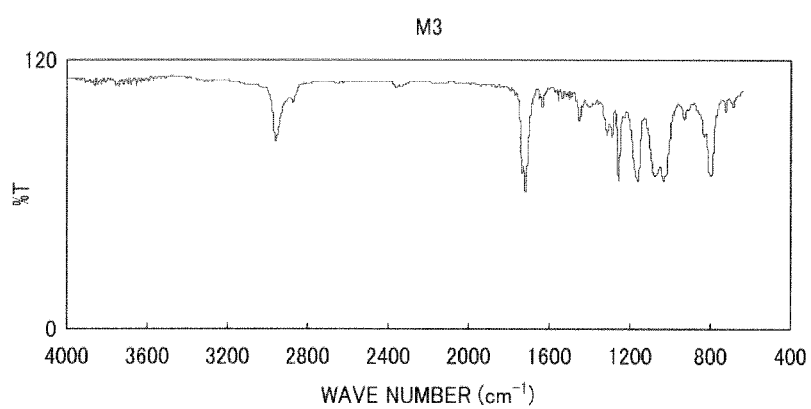
FIG. 5D is a graph illustrating an infrared absorption spectrum of a silicone compound c-M3.

The infra-red absorption spectrum graph is shown as FIG. 5D.

Synthesis Example c-IV-4

Synthesis of Silicone Compound: 1=1, m=n=0, X1=X3=Substituent A-3 in the Chemical Structure 1, R2=CH$_2$, R3=Single Bonding, 4-subtituent in Substituent A-3

Drip 4.96 parts of the compound c-II: 4-methacyloxy cyclohexane carbonate aryl ester, 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5-hexamethyl trisiloxane (manufactured by Sigma-Aldrich Co.) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.89 parts of the target silicone compound c-M4.

Figure 5E:
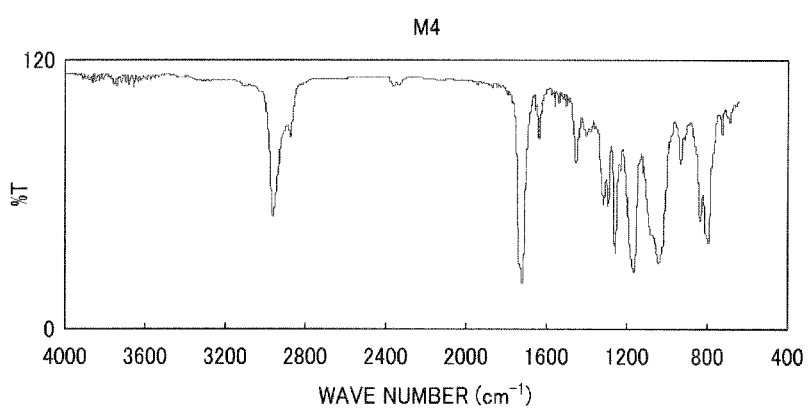
FIG. 5E is a graph illustrating an infrared absorption spectrum of a silicone compound c-M4.

The infra-red absorption spectrum graph is shown as FIG. 5E.

Synthesis Example c-IV-5

Synthesis of Silicone Compound: 1=m=n=0, X1=X3=Substituent A-3 in the Chemical Structure 1, R2=CH$_2$, R3=Single Bonding, 4-subtituent in Substituent A-3

Drip 5.77 parts of the compound c-II: 4-methacyloxy cyclohexane carbonate aryl ester, 10 parts of toluene, and 0.043 parts of xylene solution of 2% by weight platinum/1,3-divinyl-1,1,3,3-tetramethyl disiloxane complex (manufactured by Sigma-Aldrich Co.) to a solution of 1.5 parts of silicone compound: (1,1,3,3-tetramethyl trisiloxane (manufactured by Tokyo Chemical Industry Co., Ltd.) and 1.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.15 parts of the target silicone compound c-M5.

Figure 5F:
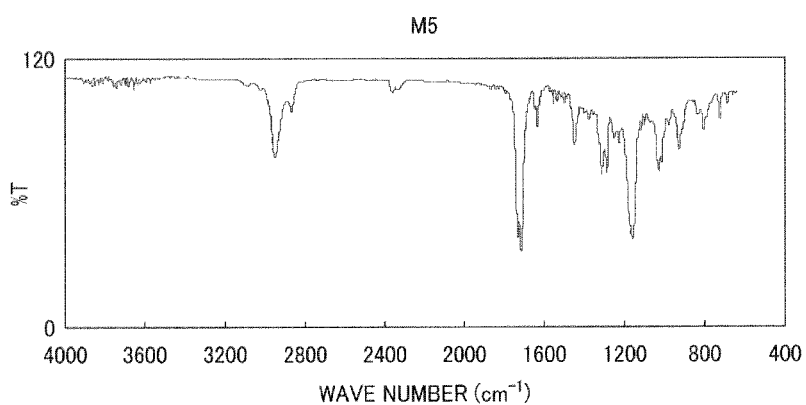
FIG. 5F is a graph illustrating an infrared absorption spectrum of a silicone compound c-M5.

The infra-red absorption spectrum graph is shown as FIG. 5F.

Synthesis Example c-IV-6

Synthesis of Silicone Compound: 1=n=0, m=1 in the Chemical Structure 2

Drip 3.49 parts of the compound c-II: 4-methacyloxy cyclohexane carbonate aryl ester, 10 parts of toluene, and 0.026 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,1,3,5,5,5-heptamethyl trisiloxane (manufactured by Tokyo Chemical Industry Co., Ltd.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.81 parts of the target silicone compound c-M6.

Figure 5G:
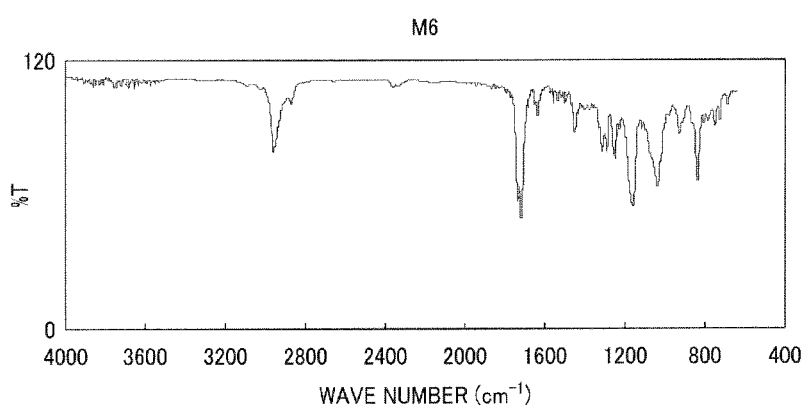
FIG. 5G is a graph illustrating an infrared absorption spectrum of a silicone compound c-M6.

The infra-red absorption spectrum graph is shown as FIG. 5G

Synthesis Example c-IV-7

Synthesis of Silicone Compound: 1 is Nearly Equal to 6, m=n=0, X1=X3=CH3, X2=Substituent A-3 in the Chemical Structure 1, R2=CH$_2$, R3=OCH$_2$CH$_2$, 4-Subtituent in Substituent A-3

Drip 2.68 parts of the compound c-III: {4-methacryloxy-cyclohexane carbonate (2-aryloxy) ethyl ester, 10 parts of toluene, and 0.016 parts of xylene solution of 2% by weight platinum/1,3-divinyl-1,1,3,3-tetramethyl disiloxane complex (manufactured by Sigma-Aldrich Co.) to a solution of 2.5 parts of silicone compound: copolymer of poly(dimethyl siloxane-methylhydroxy siloxane with ends terminated by trimethyl silyl (mol ratio: 50%) and 2.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.14 parts of the target silicone compound c-M7.

Figure 5H:
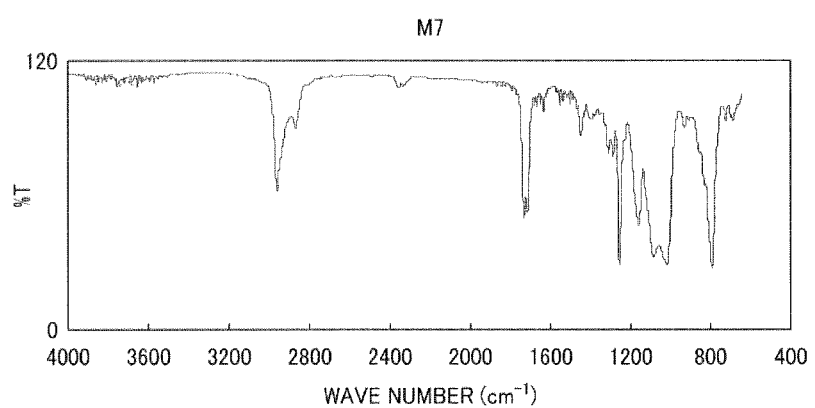
FIG. 5H is a graph illustrating an infrared absorption spectrum of a silicone compound c-M7.

The infra-red absorption spectrum graph is shown as FIG. 5H.

Example c-1

Place 1.0 part of the coloring resin particle (α), 18.56 parts of the silicone compound (c-M1), and 0.43 parts of silicone oil compound having an epoxy group (3-glycidoxy propyl (bis trimethylsiloxy)methylsilane)(manufactured by Tokyo Chemical Industry Co., Ltd.), which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example c-2

Place 1.0 part of the coloring resin particle (α), 18.76 parts of the silicone compound (c-M1), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-2.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example c-3

Place 1.0 part of the coloring resin particle (α), 18.71 parts of the silicone compound (c-M2), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-3.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example c-4

Place 1.0 part of the coloring resin particle (α), 18.71 parts of the silicone compound (c-M3), and 0.29 parts of silicone oil compound having an epoxy group (3-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-4.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example c-5

Place 1.0 part of the coloring resin particle (α), 18.71 parts of the silicone compound (c-M4), and 0.29 parts of silicone oil compound having an epoxy group (4-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-5.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example c-6

Place 1.0 part of the coloring resin particle (α), 18.76 parts of the silicone compound (c-M5), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-6.

The volume average particle diameter of the ink is 0.20 μm and the relative standard deviation (CV value) is 28%.

After the ink is preserved for 20 days, no agglomeration is observed and the volume average particle diameter is still 0.20 μm. That is, the ink has an excellent preservation stability.

Example c-7

Place 1.0 part of the coloring resin particle (α), 18.76 parts of the silicone compound (c-M7), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink c-7.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Inks of Examples c-1 to c-7 are evaluated in the same manner as in those of Examples a-1 to a-13 by the evaluation tests 1 to 3.

The results are shown in Tables 3-1 to 3-3.

Evaluation Test 1
Evaluation on Photocurability

TABLE 3-1

|  | Curing energy (mJ/cm$^2$) |
| --- | --- |
| Example c-1 (Liquid ink c-1) | 61 |
| Example c-2 (Liquid ink c-2) | 105 |
| Example c-3 (Liquid ink c-3) | 156 |
| Example c-4 (Liquid ink c-4) | 665 |
| Example c-5 (Liquid ink c-5) | 470 |
| Example c-6 (Liquid ink c-6) | 730 |
| Example c-7 (Liquid ink c-7) | 515 |

Evaluation Test 2
Image Evaluation By Electrophotographic Image Forming Apparatus

TABLE 3-2

|  | Definition |
| --- | --- |
| Example c-1 (Liquid ink c-1) | G |
| Example c-2 (Liquid ink c-2) | G |
| Example c-3 (Liquid ink c-3) | G |
| Example c-4 (Liquid ink c-4) | G |
| Example c-5 (Liquid ink c-5) | G |
| Example c-6 (Liquid ink c-6) | G |
| Example c-7 (Liquid ink c-7) | G |

Evaluation Test 3
Results of Image Evaluation for Inkjet System

TABLE 3-3

|  | Definition |
| --- | --- |
| Example c-1 (Liquid ink c-1) | G |
| Example c-2 (Liquid ink c-2) | G |
| Example c-3 (Liquid ink c-3) | G |
| Example c-4 (Liquid ink c-4) | G |
| Example c-5 (Liquid ink c-5) | G |
| Example c-6 (Liquid ink c-6) | G |
| Example c-7 (Liquid ink c-7) | G |

Synthesis Example d-II

Synthesis of Alkenyl Body of Substituent A-4: R4=R5=H

Place 33.93 parts of glycol acid aryl ester, 28.41 parts of methacrylic acid (manufactured by Tokyo Chemical Industry Co., Ltd.), 3.67 parts of dimethylamino pyridine (manufactured by Tokyo Chemical Industry Co., Ltd.), and 270 parts of toluene in a container equipped with a stirrer, a thermometer, and dripping funnel and drip 41.65 part of diisopropyl carbodimide in about 30 minutes to the container while stirring followed by six-hour stirring at room temperature to obtain a reaction product.

Next, condense the filtrate in which diisopropyl urine is filtered from the reaction product to about a half by volume followed by silica gel chromatography using toluene as a developing solvent to obtain 40.70 parts of the target compound d-II (methachloxy acetate aryl ester).

Figure 6A:
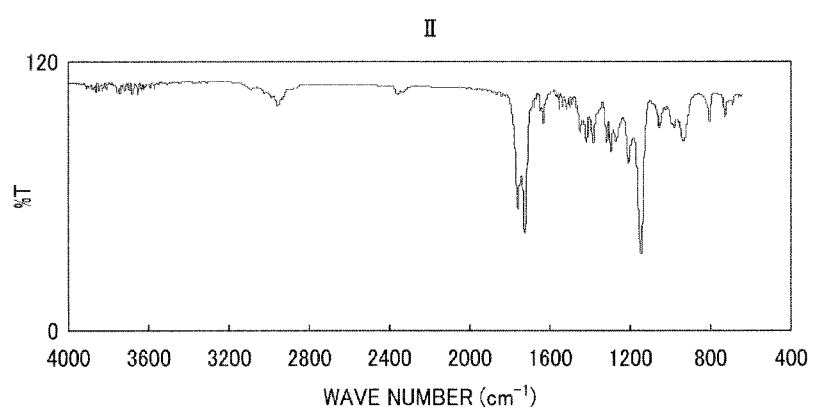
FIG. 6A is a graph illustrating an infrared absorption spectrum of a compound d-II.
Figure 6B:
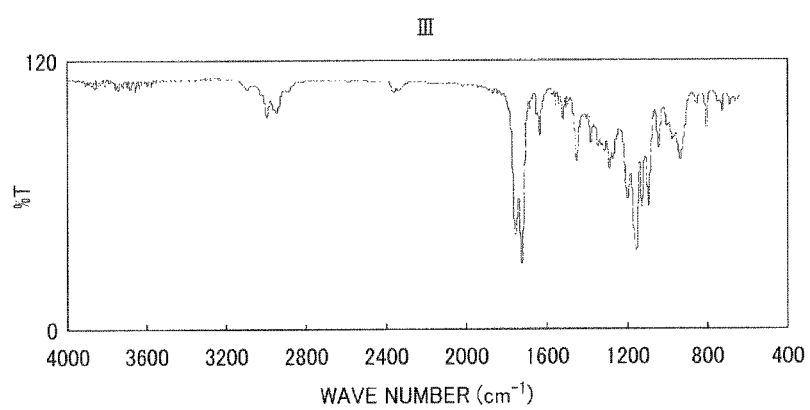
FIG. 6B is a graph illustrating an infrared absorption spectrum of a compound d-III.

The infra-red absorption spectrum graph is shown as FIG. 6A.

Synthesis Example d-III

Synthesis of Alkenyl Body of Substituent A-4: R4=CH$_3$, R5=H

Place 37.83 parts of lactic acid aryl ester, 28.41 parts of methacrylic acid (manufactured by Tokyo Chemical Industry Co., Ltd.), 3.67 parts of dimethylamino pyridine (manufactured by Tokyo Chemical Industry Co., Ltd.), and 270 parts of toluene in a container equipped with a stirrer, a thermometer, and dripping funnel and drip 41.65 parts of diisopropyl carbodimide in about 30 minutes to the container while stirring followed by six-hour stirring at room temperature to obtain a reaction product.

Next, condense the filtrate in which diisopropyl urine is filtered from the reaction product to about a half by volume followed by silica gel chromatography using toluene as a developing solvent to obtain 23.90 parts of the target compound d-III (2-methachloxy propionate aryl ester).

The infra-red absorption spectrum graph is shown as FIG. 6B.

Synthesis Example d-IV

Synthesis of Alkenyl Body of Substituent A-4: R4=R5=CH₃

Place 41.74 parts of 2-hydroxyisobutylic acid aryl ester, 28.41 parts of methacrylic acid (manufactured by Tokyo Chemical Industry Co., Ltd.), 3.67 parts of dimethylamino pyridine (manufactured by Tokyo Chemical Industry Co., Ltd.), and 270 parts of toluene in a container equipped with a stirrer, a thermometer, and dripping funnel and drip 41.65 parts of diisopropyl carbodimide in about 30 minutes to the container while stirring followed by six-hour stirring at room temperature to obtain a reaction product.

Next, condense the filtrate in which diisopropyl urine is filtered from the reaction product to about a half by volume followed by silica gel chromatography using toluene as a developing solvent to obtain 26.44 parts of the target compound d-IV (2-methachloxy propionate aryl ester).

Figure 6C:
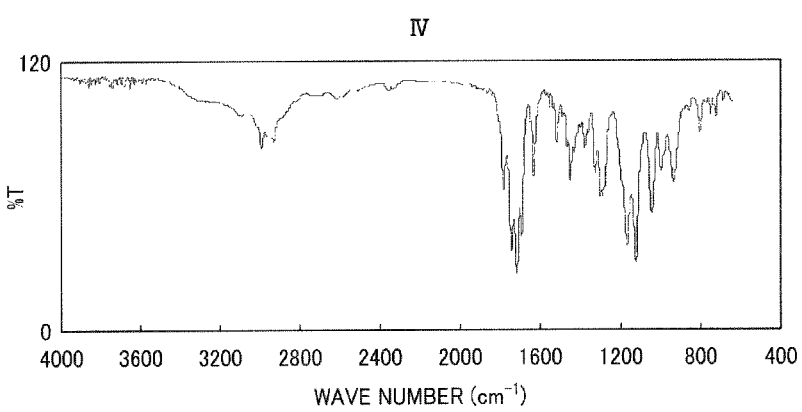
FIG. 6C is a graph illustrating an infrared absorption spectrum of a compound d-IV.

The infra-red absorption spectrum graph is shown as FIG. 6C.

Synthesis Example d-V-1

Synthesis of Silicone Compound: 1 is nearly equal to 6, m is nearly equal to 3, n=0 in the Chemical Structure 6, R4=R5=H in the Substituent A-4

Drip 3.52 parts of the compound d-II: {methacryloxy-acetic acid aryl ester, 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl) (mol ratio: 50%, manufactured by Sigma-Aldrich Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm⁻¹ of Si—H in infra-red absorption spectrum to obtain 6.46 parts of the target silicone compound d-M1.

Figure 6D:
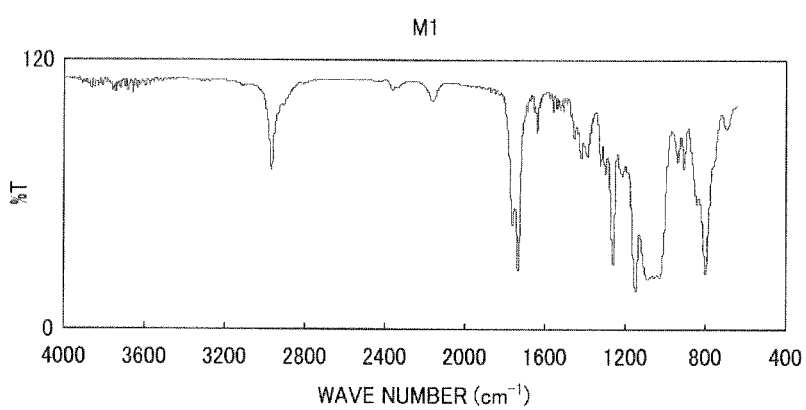
FIG. 6D is a graph illustrating an infrared absorption spectrum of a silicone compound d-M1.

The infra-red absorption spectrum graph is shown as FIG. 6D.

Synthesis Example d-V-2

Synthesis of Silicone Compound: 1 is nearly equal to 6, m is nearly equal to 3, n is Nearly equal to 3, R4=R5=H in the Substituent A-4, Y=phenoxypropyl in the Chemical Structure 6

Drip 1.68 parts of the compound d-II: methacryloxy acetic acid aryl ester, 1.24 parts of arylphenyl ether (manufactured by Tokyo Chemical Industry Co., Ltd.), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl (mol ratio: 50%) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm⁻¹ of Si—H in infra-red absorption spectrum to obtain 5.90 parts of the target silicone compound d-M2.

Synthesis Example d-V-3

Synthesis of Silicone Compound: 1=2, m=n=0, X1=X3=Substituent A-4 in the Chemical Structure 1 and R4=R5=H in the Substituent A-4

Drip 4.04 parts of the compound d-II: 4-methacyloxy acetic acid aryl ester, 10 parts of toluene, and 0.041 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5,7,7-octamethyl tetrasiloxane (manufactured by AZmax. Co) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm⁻¹ of Si—H in infra-red absorption spectrum to obtain 6.06 parts of the target silicone compound d-M3.

Figure 6E:
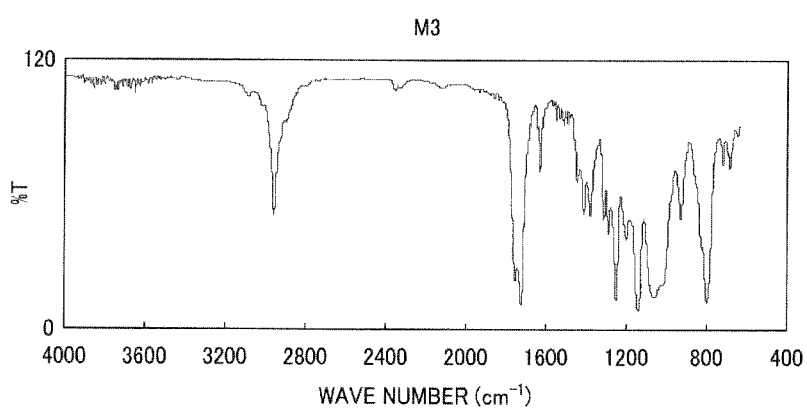
FIG. 6E is a graph illustrating an infrared absorption spectrum of a silicone compound d-M3.

The infra-red absorption spectrum graph is shown as FIG. 6E.

Synthesis of Silicone Compound: 1=1, m=n=0, X1=X3=Substituent A-4 in the Chemical Structure 1 and R4=R5=H in the Substituent A-4

Drip 3.45 parts of the compound d-II: methacyloxy acetic acid aryl ester, 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5-hexamethyl trisiloxane (manufactured by Sigma-Aldrich Co) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm⁻¹ of Si—H in infra-red absorption spectrum to obtain 4.18 parts of the target silicone compound d-M4.

Figure 6F:
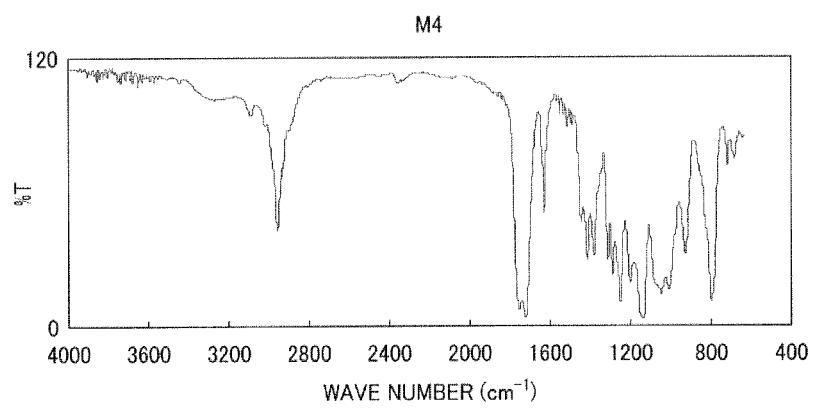
FIG. 6F is a graph illustrating an infrared absorption spectrum of a silicone compound d-M4.

The infra-red absorption spectrum graph is shown as FIG. 6F.

Synthesis Example d-V-5

Synthesis of Silicone Compound: 1=m=n=0, X1=X3=Substituent A-4 in the Chemical Structure 1 and R4=R5=H in the Substituent A-4

Drip 4.25 parts of the compound d-II: 4-methacyloxy acetic acid aryl ester, 10 parts of toluene, and 0.043 parts of xylene solution of 2% by weight platinum/1,3-divinyl-1,1,3,3-tetramethyl disiloxane complex (manufactured by Sigma-Aldrich Co.) to a solution of 1.5 parts of silicone compound: (1,1,3,3-tetramethyl trisiloxane (manufactured by Tokyo Chemical Industry Co., Ltd.) and 1.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm⁻¹ of Si—H in infra-red absorption spectrum to obtain 4.24 parts of the target silicone compound d-M5.

Figure 6G:
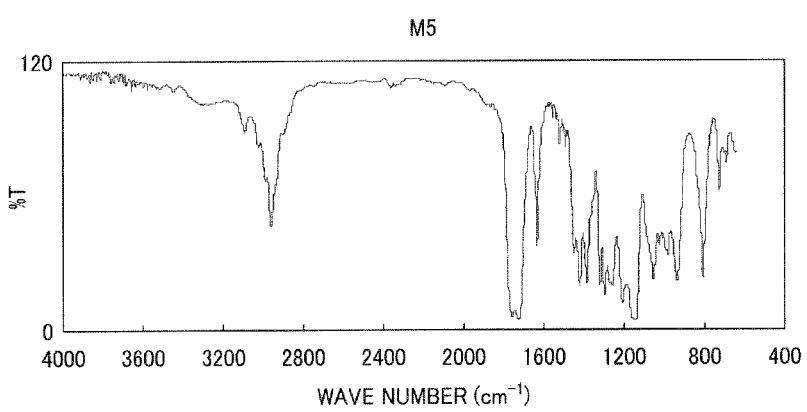
FIG. 6G is a graph illustrating an infrared absorption spectrum of a silicone compound d-M5.

The infra-red absorption spectrum graph is shown as FIG. 6G

Synthesis Example d-V-6

Synthesis of Silicone Compound: l=n=0, m=1 in the Chemical Structure 6 and R4=R5=H in the Substituent A-4

Drip 2.56 parts of the compound d-II: 4-methacyloxy acetic acid aryl ester, 10 parts of toluene, and 0.026 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,1,3,5,5,5-heptamethyl trisiloxane (manufactured by Tokyo Chemical Industry Co., Ltd.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 2.93 parts of the target silicone compound d-M6.

Figure 6H:
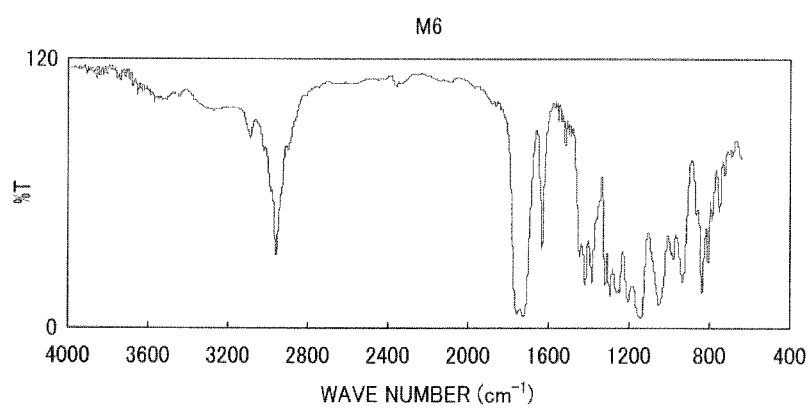
FIG. 6H is a graph illustrating an infrared absorption spectrum of a silicone compound d-M6.

The infra-red absorption spectrum graph is shown as FIG. 6H.

Synthesis Example d-V-7

Synthesis of Silicone Compound: l is Nearly Equal to 6, m=is Nearly Equal to 3, n=0 in the Chemical Structure 6 and R4=$CH_3$, R5=H in the Substituent A-4

Drip 3.78 parts of the compound d-III: 2-methacryloxy propionic acid aryl ester, 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl) (mol ratio: 50%, manufactured by Sigma-Aldrich Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 6.32 parts of the target silicone compound d-M7.

Figure 6I:
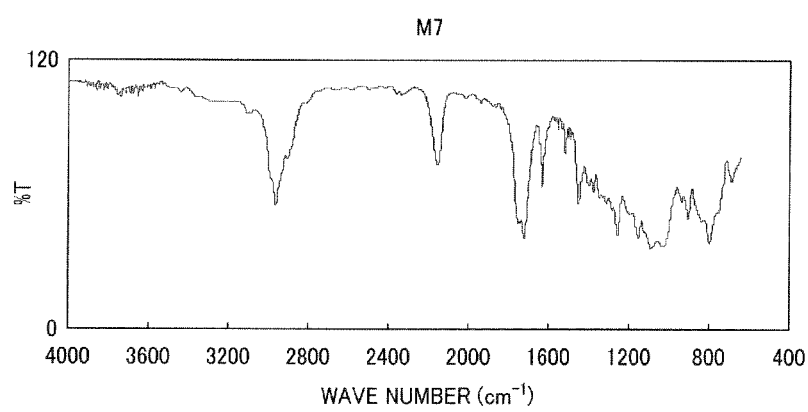
FIG. 6I is a graph illustrating an infrared absorption spectrum of a silicone compound d-M7.

The infra-red absorption spectrum graph is shown as FIG. 6I.

Synthesis Example d-V-8

Synthesis of Silicone Compound: l is Nearly Equal to 6, m=n=0, X1=X3=Substituent A-4 in the Chemical Structure 1 and R4=$CH_3$, R5=H in the Substituent A-4

Drip 2.11 parts of the compound d-III: 2-methacryloxy propionic acid aryl ester, 10 parts of toluene, and 0.020 parts of xylene solution of 2% by weight platinum/1,3-divinyl-1,1,3,3-tetramethyl disiloxane complex (manufactured by Sigma-Aldrich Co.) to a solution of 3.0 parts of silicone compound: polydimethyl siloxane with ends terminated by hydride) (molecular weight: Mn=580, manufactured by Sigma-Aldrich Co.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 4.87 parts of the target silicone compound d-M8.

Figure 6J:
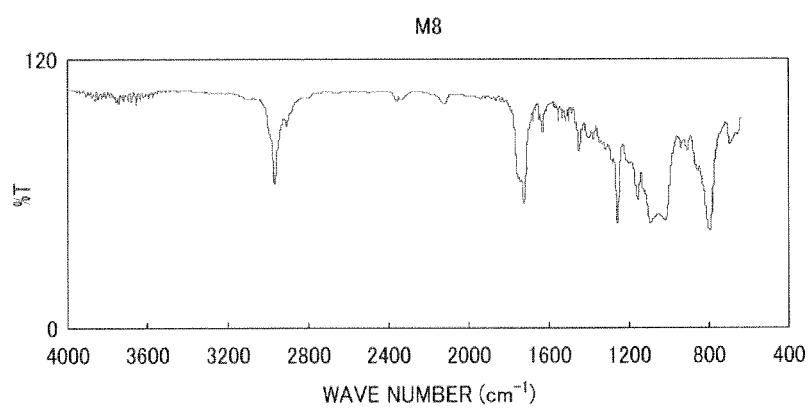
FIG. 6J is a graph illustrating an infrared absorption spectrum of a silicone compound d-M8.

The infra-red absorption spectrum graph is shown as FIG. 6J.

Synthesis Example d-V-9

Synthesis of Silicone Compound: l=1, m=n=0, X1=X3=Substituent A-4 in the Chemical Structure 1, R4=$CH_3$, R5=H in the Substituent A-4

Drip 3.91 parts of the compound d-III: methacyloxy propionic acid aryl ester, 10 parts of toluene, and 0.037 parts of xylene solution of 2% by weight platinum/1,3-divinyl-1,1,3,3-tetramethyl disiloxane complex (manufactured by Sigma-Aldrich Co.) to a solution of 2.0 parts of silicone compound: (1,1,3,3,5,5-hexamethyl trisiloxane (manufactured by Sigma-Aldrich Co) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 4.53 parts of the target silicone compound d-M9.

Figure 6K:
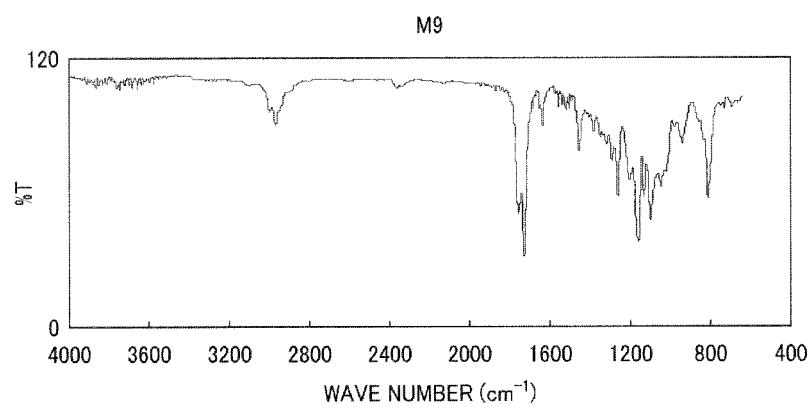
FIG. 6K is a graph illustrating an infrared absorption spectrum of a silicone compound d-M9.

The infra-red absorption spectrum graph is shown as FIG. 6K.

Synthesis Example d-V-10

Synthesis of Silicone Compound: l is Nearly Equal to 6, m is Nearly Equal to 3, n=0 in the Chemical Structure 6 and R4=R5=$CH_3$ in the Substituent A-4

Drip 3.36 parts of the compound d-IV: 2-methacryloxy isobutylic acid aryl ester, 10 parts of toluene, and 0.029 parts of xylene solution of 2% by weight platinum/1,3-divinyl-1,1,3,3-tetramethyl disiloxane complex (manufactured by Sigma-Aldrich Co.) to a solution of 2.5 parts of silicone compound: copolymer of poly(dimethyl siloxane-methylhydroxy siloxane with ends terminated by trimethyl silyl) (mol ratio: 50%, manufactured by Sigma-Aldrich Co.) and 2.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 5.52 parts of the target silicone compound d-M10.

Figure 6L:
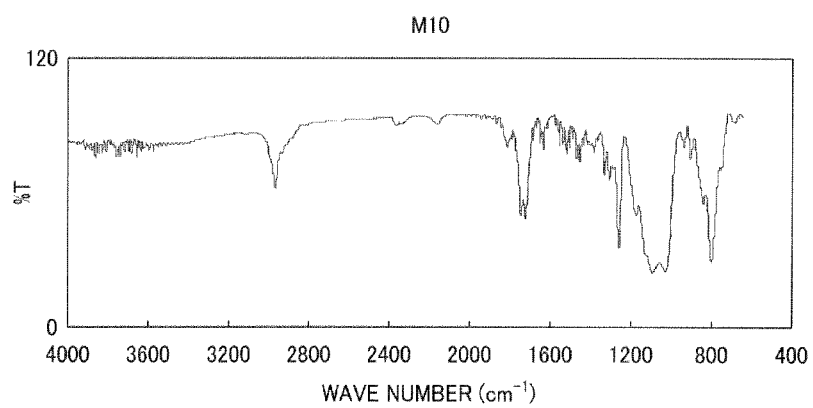
FIG. 6L is a graph illustrating an infrared absorption spectrum of a silicone compound d-M10.

The infra-red absorption spectrum graph is shown as FIG. 6L.

Synthesis Example d-V-11

Synthesis of Silicone Compound: l is Nearly Equal to 4, m=n=0 in the Chemical Structure 6 and R4=R5=$CH_3$ in the Substituent A-4

Drip 2.90 parts of the compound d-IV: 2-methacryloxy isobutylic acid aryl ester, 10 parts of toluene, and 0.025 parts of xylene solution of 2% by weight platinum/1,3-divinyl-1,1,3,3-tetramethyl disiloxane complex (manufactured by Sigma-Aldrich Co.) to a solution of 2.5 parts of silicone compound: copolymer of polydimethyl siloxane with ends terminated by methylsilyl) (molecular weight Mn; up to 500, manufactured by AzMax Co.) and 2.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.59 parts of the target silicone compound d-M11.

Figure 6M:
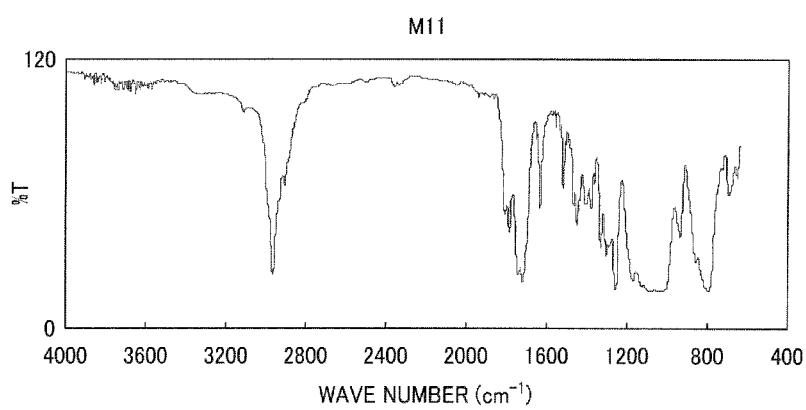
FIG. 6M is a graph illustrating an infrared absorption spectrum of a silicone compound d-M11.

The infra-red absorption spectrum graph is shown as FIG. 6M.

Example d-1

Place 1.0 part of the coloring resin particle ($\alpha$), 18.56 parts of the silicone compound (d-M1), and 0.43 parts of silicone oil compound having an epoxy group (3-glycidoxy propyl (bis trimethylsiloxy)methylsilane)(manufactured by Tokyo Chemical Industry Co., Ltd.), which is the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-1.

The volume average particle diameter of the ink is 0.22 µm and the relative standard deviation (CV value) is 28%.

After the ink is preserved for 20 days, no agglomeration is observed and the volume average particle diameter is still 0.22 µm. That is, the ink has an excellent preservation stability.

Example d-2

Place 1.0 part of the coloring resin particle ($\alpha$), 18.76 parts of the silicone compound (d-M1), and 0.24 parts of silicone oil compound having an epoxy group (2-ethylhexyl glycidyl ether, manufactured by Tokyo Chemical Industry Co., Ltd.) which is the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-2.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example d-3

Place 1.0 part of the coloring resin particle ($\alpha$), 18.71 parts of the silicone compound (d-M2), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-3.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example d-4

Place 1.0 part of the coloring resin particle ($\alpha$), 18.71 parts of the silicone compound (d-M3), and 0.29 parts of silicone oil compound having an epoxy group (3-ethylhexyl glycidyl ether, manufactured by Tokyo Chemical Industry Co., Ltd.) which is 1.2 times the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-4.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example d-5

Place 1.0 part of the coloring resin particle ($\alpha$), 18.71 parts of the silicone compound (d-M4), and 0.29 parts of silicone oil compound having an epoxy group (4-ethylhexyl glycidyl ether, manufactured by Tokyo Chemical Industry Co., Ltd.) which is 1.2 times the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-5.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example d-6

Place 1.0 part of the coloring resin particle ($\alpha$), 18.76 parts of the silicone compound (d-M7), and 0.24 parts of silicone oil compound having an epoxy group (2-ethylhexyl glycidyl ether, manufactured by Tokyo Chemical Industry Co., Ltd.) which is the equivalent to the acid value of the coloring resin particles ($\alpha$) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-6.

The volume average particle diameter of the ink is 0.20 µm and the relative standard deviation (CV value) is 28%.

After the ink is preserved for 20 days, no agglomeration is observed and the volume average particle diameter is still 0.20 µm. That is, the ink has an excellent preservation stability.

Example d-7

Place 1.0 part of the coloring resin particle ($\alpha$), 18.76 parts of the silicone compound (d-M8), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-7.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example d-8

Place 1.0 part of the coloring resin particle (α), 18.76 parts of the silicone compound (d-M10), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink d-8.

The volume average particle diameter of the ink is 0.20 μm and the relative standard deviation (CV value) is 28%.

After the ink is preserved for 20 days, no agglomeration is observed and the volume average particle diameter is still 0.20 μm That is, the ink has an excellent preservation stability.

Inks of Examples d-1 to d-8 are evaluated in the same manner as in Those of Examples a-1 to a-13 by the evaluation tests 1 to 3.

The results are shown in Tables 4-1 to 4-3.

Evaluation Test 1
Evaluation on Photocurability

TABLE 4-1

|  | Curing energy (mJ/cm$^2$) |
| --- | --- |
| Example d-1 (Liquid ink d-1) | 385 |
| Example d-2 (Liquid ink d-2) | 350 |
| Example d-3 (Liquid ink d-3) | 460 |
| Example d-4 (Liquid ink d-4) | 950 |
| Example d-5 (Liquid ink d-5) | 735 |
| Example d-6 (Liquid ink d-6) | 200 |
| Example d-7 (Liquid ink d-7) | 655 |
| Example d-8 (Liquid ink d-8) | 775 |

Evaluation Test 2
Image Evaluation By Electrophotographic Image Forming Apparatus

TABLE 4-2

|  | Definition |
| --- | --- |
| Example d-1 (Liquid ink d-1) | G |
| Example d-2 (Liquid ink d-2) | G |
| Example d-3 (Liquid ink d-3) | G |
| Example d-4 (Liquid ink d-4) | G |
| Example d-5 (Liquid ink d-5) | G |
| Example d-6 (Liquid ink d-6) | G |
| Example d-7 (Liquid ink d-7) | G |
| Example d-8 (Liquid ink d-8) | G |

Evaluation Test 3
Results of Image Evaluation for Inkjet System

TABLE 4-3

|  | Definition |
| --- | --- |
| Example d-1 (Liquid ink d-1) | G |
| Example d-2 (Liquid ink d-2) | G |
| Example d-3 (Liquid ink d-3) | G |
| Example d-4 (Liquid ink d-4) | G |
| Example d-5 (Liquid ink d-5) | G |
| Example d-6 (Liquid ink d-6) | G |
| Example d-7 (Liquid ink d-7) | G |
| Example d-8 (Liquid ink d-8) | G |

Synthesis Example e-II

Synthesis of Alkenyl Body of Substituent A-5

Place 19.82 parts of 3-aryloxy-1,2-propane diol (manufactured by Tokyo Chemical Industry Co., Ltd.), 28.41 parts of methacrylic acid (manufactured by Tokyo Chemical Industry Co., Ltd.), 3.67 parts of dimethylamino pyridine (manufactured by Tokyo Chemical Industry Co., Ltd.), and 200 parts of toluene in a container equipped with a stirrer, a thermometer, and dripping funnel and drip 41.65 parts of diisopropyl carbodiimide in about 30 minutes to the container while stirring followed by six-hour stirring at room temperature to obtain a reaction product.

Next, condense the filtrate in which diisopropyl urine is filtered from the reaction product to about a half by volume followed by silica gel chromatography using toluene as a developing solvent to obtain 23.67 parts of the target compound e-II (3-aryloxy-1,2-propane diol dimethacrylate).

Synthesis Example e-III-1

Synthesis of Silicone Compound: 1 is Nearly Equal to 6, m is Nearly Equal to 3, n is Nearly Equal to 3, and Y=phenoxypropyl in the Chemical Structure 6

Drip 2.48 parts of the compound e-II: {3-aryloxy 1,2-propane diol dimethacrylate, 1.24 parts of arylphenyl ether (manufactured by Tokyo Chemical Industry Co., Ltd.), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl (mol ratio: 50%) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 6.83 parts of the target silicone compound e-M1.

Figure 7A:
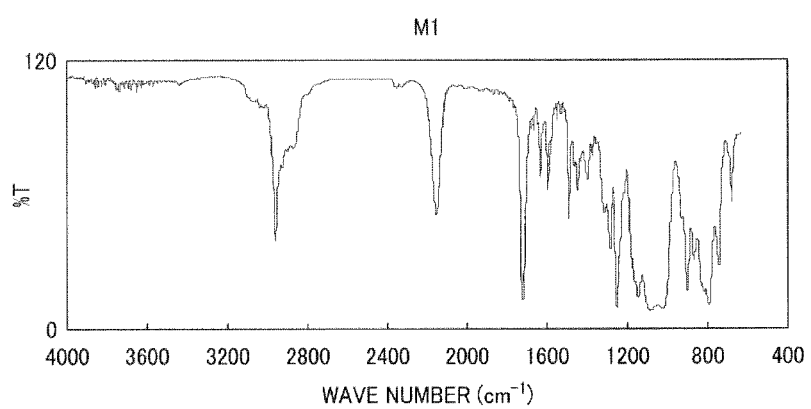
FIG. 7A is a graph illustrating an infrared absorption spectrum of a silicone compound e-M1.

The infra-red absorption spectrum graph is shown as FIG. 7A.

Synthesis Example e-III-2

Synthesis of Silicone Compound: 1 is nearly equal to 6, m=n=0, X1=X3=Substituent A-5 in the Chemical Structure 1

Drip 2.59 parts of the compound e-II: 3-aryloxy 1,2-propane diol dimethacrylate, 10 parts of toluene, and 0.018 parts of xylene solution of 2% by weight platinum/1,3-divinyl-1, 1,3,3-tetramethyl disiloxane complex (manufactured by Sigma-Aldrich Co.) to a solution of 2.8 parts of silicone compound: polydimethyl siloxane with ends terminated by hydride) (molecular weight: Mn=580, manufactured by Sigma-Aldrich Co.) and 2.8 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 5.60 parts of the target silicone compound e-M2.

Figure 7B:
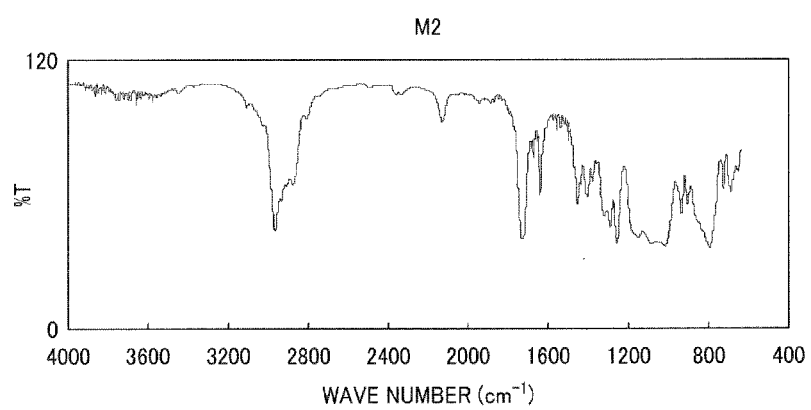
FIG. 7B is a graph illustrating an infrared absorption spectrum of a silicone compound e-M2.

The infra-red absorption spectrum graph is shown as FIG. 7B.

Synthesis Example e-III-3

Synthesis of Silicone Compound: l=1, m=n=0, X1=X3=Substituent A-5 in the Chemical Structure 1

Drip 3.86 parts of the compound e-II: 3-aryloxy 1,2-propane diol dimethacrylate, 10 parts of toluene, and 0.027 parts of xylene solution of 2% by weight platinum/1,3-divinyl-1,1,3,3-tetramethyl disiloxane complex (manufactured by Sigma-Aldrich Co.) to a solution of 1.5 parts of silicone compound: 1,1,3,3,5,5-hexamethyl trisiloxane (manufactured by Sigma-Aldrich Co.) and 1.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 3.91 parts of the target silicone compound e-M3.

Figure 7C:
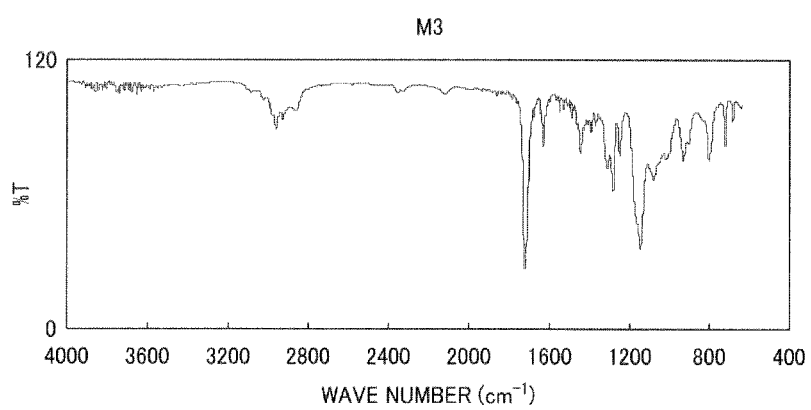
FIG. 7C is a graph illustrating an infrared absorption spectrum of a silicone compound e-M3.

The infra-red absorption spectrum graph is shown as FIG. 7C.

Synthesis Example e-III-4

Synthesis of Silicone Compound: l=m=n=0, X1=X3=Substituent A-5 in the Chemical Structure 1

Drip 4.00 parts of the compound e-II: 3-aryloxy 1,2-propane diol dimethacrylate, 10 parts of toluene, and 0.028 parts of xylene solution of 2% by weight platinum/1,3-diyinyl-1,1,3,3-tetramethyl disiloxane complex (manufactured by Sigma-Aldrich Co.) to a solution of 1.0 parts of silicone compound: 1,1,3,3-tetramethyl trisiloxane (manufactured by Tokyo Chemical Industry Co., Ltd.) and 1.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 3.85 parts of the target silicone compound e-M4.

Figure 7D:
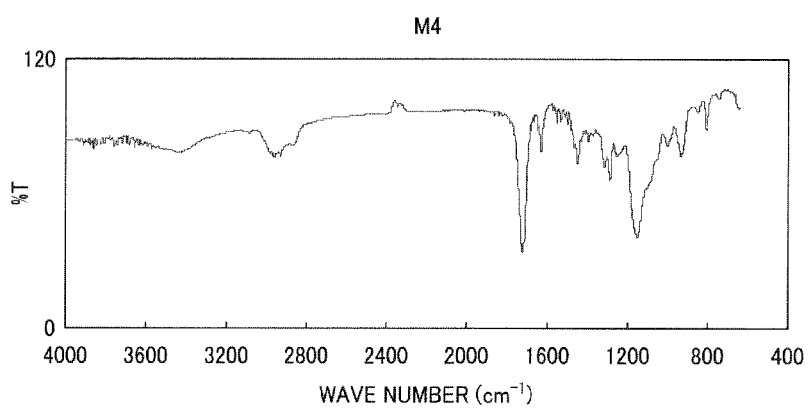
FIG. 7D is a graph illustrating an infrared absorption spectrum of a silicone compound e-M4.

The infra-red absorption spectrum graph is shown as FIG. 7D.

Synthesis Example e-III-5

Synthesis of Silicone Compound: l=n=0, m=1 in the Chemical Structure 6

Drip 3.62 parts of the compound e-II: 3-aryloxy 1,2-propane diol dimethacrylate, 10 parts of toluene, and 0.026 parts of xylene solution of 2% by weight platinum/1,3-diyinyl-1,1,3,3-tetramethyl disiloxane complex (manufactured by Sigma-Aldrich Co.) to a solution of 3.0 parts of silicone compound: 1,1,1,3,5,5,5-heptamethyl trisiloxane (manufactured by Tokyo Chemical Industry Co., Ltd.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 3.76 parts of the target silicone compound e-M5.

Figure 7E:
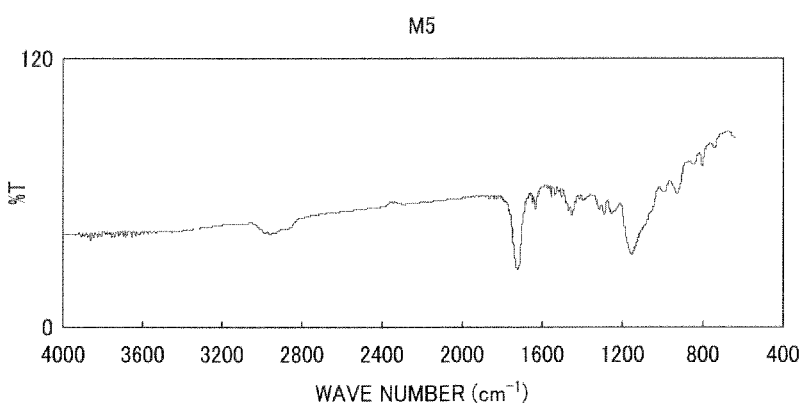
FIG. 7E is a graph illustrating an infrared absorption spectrum of a silicone compound e-M5.

The infra-red absorption spectrum graph is shown as FIG. 7E.

Example e-1

Place 1.0 part of the coloring resin particle (α), 18.56 parts of the silicone compound (e-M1), and 0.43 parts of silicone oil compound having an epoxy group (3-glycidoxy propyl (bis trimethylsiloxy)methylsilane)(manufactured by Tokyo Chemical Industry Co., Ltd.), which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example e-2

Place 1.0 part of the coloring resin particle (α), 18.76 parts of the silicone compound (e-M1), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-2.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example e-3

Place 1.0 part of the coloring resin particle (α), 18.71 parts of the silicone compound (e-M2), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-3.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example e-4

Place 1.0 part of the coloring resin particle (α), 18.71 parts of the silicone compound (e-M3), and 0.29 parts of silicone oil compound having an epoxy group (3-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-4.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example e-5

Place 1.0 part of the coloring resin particle (α), 18.71 parts of the silicone compound (e-M4), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-5.

The volume average particle diameter of the ink is 0.21 µm and the relative standard deviation (CV value) is 28%.

After the ink is preserved for 20 days, no agglomeration is observed and the volume average particle diameter is still 0.21 µm. That is, the ink has an excellent preservation stability.

Example e-6

Place 1.0 part of the coloring resin particle (α), 18.76 parts of the silicone compound (e-M5), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink e-6.

The volume average particle diameter of the ink is 0.20 µm and the relative standard deviation (CV value) is 28%.

After the ink is preserved for 20 days, no agglomeration is observed and the volume average particle diameter is still 0.20 µm. That is, the ink has an excellent preservation stability.

Inks of Examples e-1 to e-6 are evaluated in the same manner as in Those of Examples a-1 to a-13 by the evaluation tests 1 to 3.

The results are shown in Tables 5-1 to 5-3.

Evaluation Test 1
Evaluation on Photocurability

TABLE 5-1

|  | Curing energy (mJ/cm$^2$) |
| --- | --- |
| Example e-1 (Liquid ink e-1) | 280 |
| Example e-2 (Liquid ink e-2) | 255 |
| Example e-3 (Liquid ink e-3) | 425 |
| Example e-4 (Liquid ink e-4) | 212 |
| Example e-5 (Liquid ink e-5) | 167 |
| Example e-6 (Liquid ink e-6) | 135 |

Evaluation Test 2
Image Evaluation By Electrophotographic Image Forming Apparatus

TABLE 5-2

|  | Definition |
| --- | --- |
| Example e-1 (Liquid ink e-1) | G |
| Example e-2 (Liquid ink e-2) | G |
| Example e-3 (Liquid ink e-3) | G |
| Example e-4 (Liquid ink e-4) | G |
| Example e-5 (Liquid ink e-5) | G |
| Example e-6 (Liquid ink e-6) | G |

Evaluation Test 3
Results of Image Evaluation for Inkjet System

TABLE 5-3

|  | Definition |
| --- | --- |
| Example e-1 (Liquid ink e-1) | G |
| Example e-2 (Liquid ink e-2) | G |
| Example e-3 (Liquid ink e-3) | G |
| Example e-4 (Liquid ink e-4) | G |
| Example e-5 (Liquid ink e-5) | G |
| Example e-6 (Liquid ink e-6) | G |

Synthesis Example f-II

Synthesis of Alkenyl Body of Substituent A-6

Drip 11.42 parts of aryl amine (manufactured by Tokyo Chemical Industry Co., Ltd.) to a solution of 274 parts of 1,2-dichloroethane of 28.62 parts of maleic anhydride (manufactured by Tokyo Chemical Industry Co., Ltd.) in a container equipped with a stirrer, a condenser, a thermometer, and a dripping funnel in an about 30 minutes while stirring at room temperature followed by a two-hour stirring at room temperature to obtain a reaction solution.

Add 29.98 parts of zinc chlorate (manufactured by Kanto Chemical Co., Inc.) to the reaction solution and heat the liquid to the reflux point (82° C.) and drip 53.26 parts of hexamethyl silazane (manufactured by Tokyo Chemical Industry Co., Ltd.) thereto in an about one hour followed by reaction for three hours under while in reflux.

Subsequent to cooling down, pour the reaction liquid to iced water to have an acidity of hydrochloric acid followed by stirring for a while. Subsequent to extraction by 1,2-dichloroethane and washing twice, dehydrate the 1,2-dichloroethane phase with anhydrous magnesium sulfate.

Thereafter, filter magnesium sulfate, distill away 1,2-dichloroethane from the filtrate. Subsequent to silica gel chromatography for the residual using toluen/ethylacetate (5/1) as a developing solvent, re-crystalize the obtained crystal by toluene to obtain 20.38 parts of the target compound (Compound f-II: N-aryl maleimide).

The melting point thereof is 43.5° C. to 45.0° C.

Figure 8A:
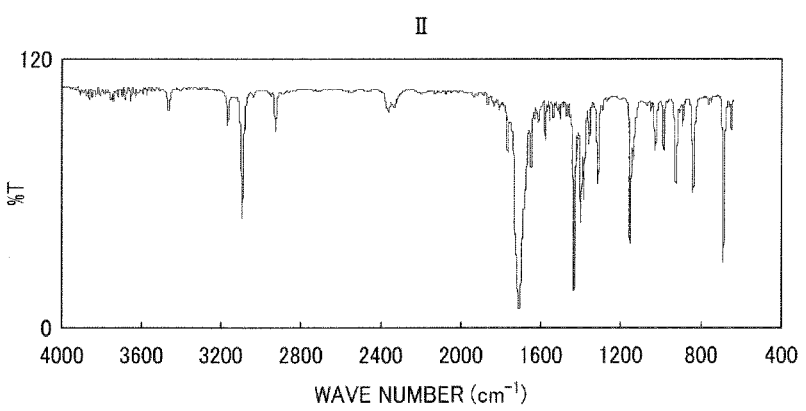
FIG. 8A is a graph illustrating an infrared absorption spectrum of a compound f-II.

The infra-red absorption spectrum graph is shown as FIG. 8A.

Synthesis Example f-III-1

Synthesis of Silicone Compound: 1 is nearly equal to 6, m is nearly equal to 3, n is nearly equal to 3, and Y=phenoxypropyl in the Chemical Structure 6

Drip 1.27 parts of the compound f-II: N-aryl maleimide, 1.24 parts of arylphenyl ether (manufactured by Tokyo Chemical Industry Co., Ltd.), 10 parts of toluene, and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl (mol ratio: 50%) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.81 parts of the target silicone compound f-M1.

Synthesis Example f-III-2

Synthesis of Silicone Compound: 1 is Nearly Equal to 6, m is Nearly Equal to 3, n is Nearly Equal to 3, and Y=phenoxypropyl in the Chemical Structure 6

Drip 1.27 parts of the compound f-II: N-aryl maleimide, 1.61 parts of vinyl pentamethyl disiloxane (manufactured by Azmax Co.), and 0.035 parts of xylene solution of 2% by weight platinum/1,3-divinyl-1,1,3,3-tetramethyl disiloxane complex (manufactured by Sigma-Aldrich Co.) to a solution of 3.0 parts of silicone compound: copolymer of poly(dimethyl siloxane-methylhydroxy siloxane with ends terminated by trimethyl silyl (mol ratio: 50%) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.68 parts of the target silicone compound f-M2.

Figure 8B:
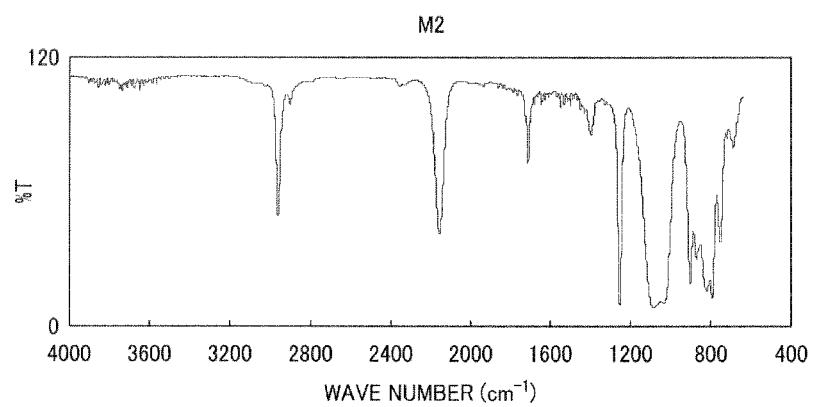
FIG. 8B is a graph illustrating an infrared absorption spectrum of a silicone compound f-M2.

The infra-red absorption spectrum graph is shown as FIG. 8B.

Synthesis Example f-III-3

Synthesis of Silicone Compound: 1 is Nearly Equal to 6, m=n=0, X1=X3=Substituent A-6 in the Chemical Structure 1

Drip 2.84 parts of the compound f-III: N-aryl maleimide, 10 parts of toluene, and 0.040 parts of xylene solution of 2% by weight platinum/1,3-divinyl-1,1,3,3-tetramethyl disiloxane complex (manufactured by Sigma-Aldrich Co.) to a solution of 6.0 parts of silicone compound: polydimethyl siloxane with ends terminated by hydride) (molecular weight Mn; 580, manufactured by Sigma-Aldrich Co.) and 6.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 9.87 parts of the target silicone compound f-M3.

Figure 8C:
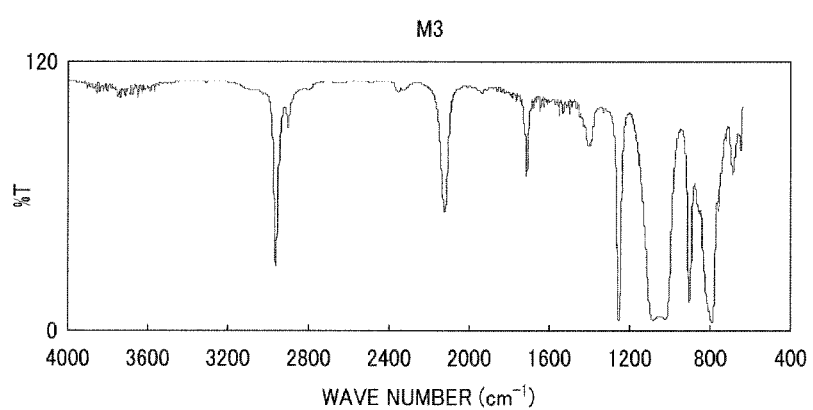
FIG. 8C is a graph illustrating an infrared absorption spectrum of a silicone compound f-M3.

The infra-red absorption spectrum graph is shown as FIG. 8C.

Synthesis Example f-III-4

Synthesis of Silicone Compound: 1=1, m=n=0, X1=X3=Substituent A-6 in the Chemical Structure 1

Drip 3.95 parts of the compound f-II: N-aryl maleimide, 10 parts of toluene, and 0.055 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,3,3,5,5-hexamethyl trisiloxane (manufactured by Sigma-Aldrich Co) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.85 parts of the target silicone compound f-M4.

Figure 8D:
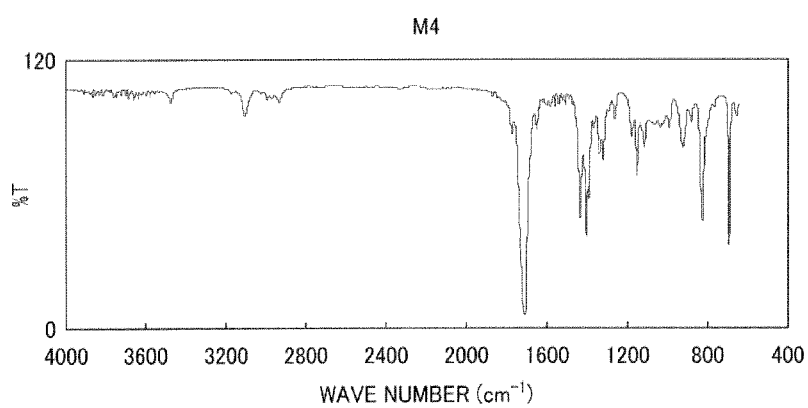
FIG. 8D is a graph illustrating an infrared absorption spectrum of a silicone compound f-M4.

The infra-red absorption spectrum graph is shown as FIG. 8D.

Synthesis Example f-III-5

Synthesis of Silicone Compound: 1=m=n=0, and X1=X3=Substituent A-6 in the Chemical Structure 1

Drip 4.14 parts of the compound f-II: N-aryl maleimide, 10 parts of toluene, and 0.055 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,3,3-tetramethyl trisiloxane (manufactured by Tokyo Chemical Industry Co., Ltd.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 4.14 parts of the target silicone compound f-M5.

Figure 8E:
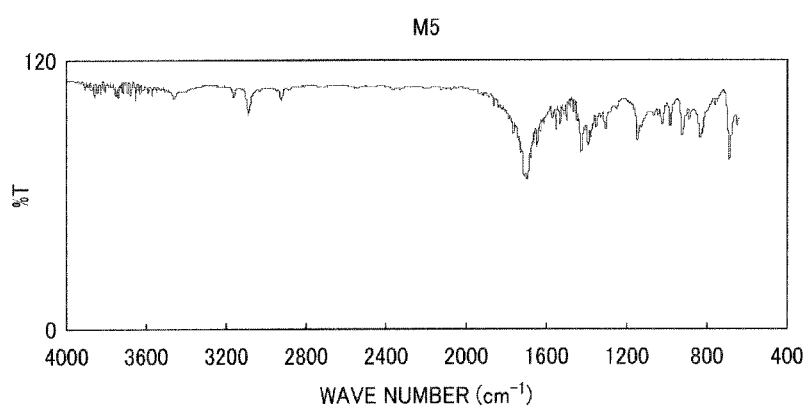
FIG. 8E is a graph illustrating an infrared absorption spectrum of a silicone compound f-M5.

The infra-red absorption spectrum graph is shown as FIG. 8E.

Synthesis Example f-III-6

Synthesis of Silicone Compound: 1=n=0, m=1 in the Chemical Structure 6

Drip 3.08 parts of the compound f-II: N-aryl maleimide, 10 parts of toluene, and 0.043 parts of xylene solution of 2% by weight platinum/1,3-divinyl-1,1,3,3-tetramethyl disiloxane complex (manufactured by Sigma-Aldrich Co.) to a solution of 5.0 parts of silicone compound: (1,1,1,3,5,5,5-heptamethyl trisiloxane (manufactured by Sigma-Aldrich Co) and 5.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 5.01 parts of the target silicone compound f-M6.

Figure 8F:
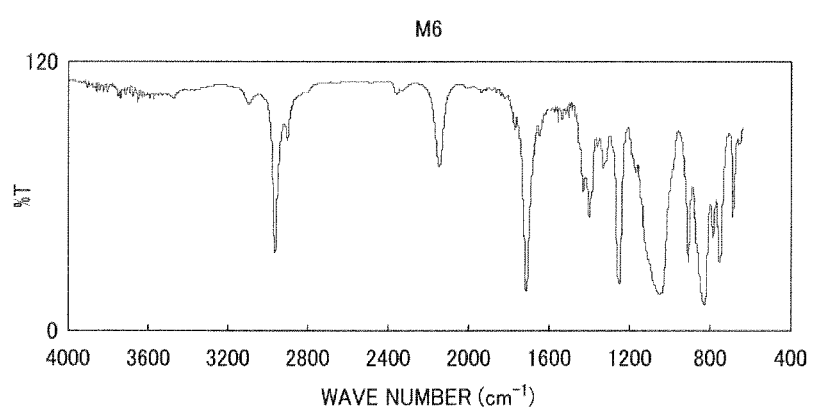
FIG. 8F is a graph illustrating an infrared absorption spectrum of a silicone compound f-M6.

The infra-red absorption spectrum graph is shown as FIG. 8F.

Example f-1

Place 1.0 part of the coloring resin particle (α), 18.56 parts of the silicone compound (f-M1), and 0.43 parts of silicone oil compound having an epoxy group (3-glycidoxy propyl(bis trimethylsiloxy)methylsilane)(manufactured by Tokyo Chemical Industry Co., Ltd.), which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink f-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example f-2

Place 1.0 part of the coloring resin particle (α), 18.76 parts of the silicone compound (f-M1), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink f-2.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example f-3

Place 1.0 part of the coloring resin particle (α), 18.71 parts of the silicone compound (f-M3), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink f-3.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example f-4

Place 1.0 part of the coloring resin particle (α), 18.71 parts of the silicone compound (f-M4), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink f-4.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example f-5

Place 1.0 part of the coloring resin particle (α), 18.71 parts of the silicone compound (f-M5), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink f-5.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Inks of Examples f-1 to f-5 are evaluated in the same manner as in Those of Examples a-1 to a-13 by the evaluation tests 1 to 3.

The results are shown in Tables 6-1 to 6-3.

Evaluation Test 1

Evaluation on Photocurability

TABLE 6-1

|  | Curing energy (mJ/cm$^2$) |
|---|---|
| Example f-1 (Liquid ink f-1) | 620 |
| Example f-2 (Liquid ink f-2) | 590 |
| Example f-3 (Liquid ink f-3) | 1050 |
| Example f-4 (Liquid ink f-4) | 520 |
| Example f-5 (Liquid ink f-5) | 475 |

Evaluation Test 2
Image Evaluation By Electrophotographic Image Forming Apparatus

TABLE 6-2

|  | Definition |
| --- | --- |
| Example f-1 (Liquid ink f-1) | G |
| Example f-2 (Liquid ink f-2) | G |
| Example f-3 (Liquid ink f-3) | G |
| Example f-4 (Liquid ink f-4) | G |
| Example f-5 (Liquid ink f-5) | G |

Evaluation Test 3
Results of Image Evaluation for Inkjet System

TABLE 6-3

|  | Definition |
| --- | --- |
| Example f-1 (Liquid ink f-1) | G |
| Example f-2 (Liquid ink f-2) | G |
| Example f-3 (Liquid ink f-3) | G |
| Example f-4 (Liquid ink f-4) | G |
| Example f-5 (Liquid ink f-5) | G |

Synthesis Example g-II

Synthesis of Alkenyl Body of Substituent A-7

Drip 13.88 parts of diisopropyl carbodiimide (manufactured by Tokyo Chemical Industry Co., Ltd.) to a solution of 200 parts of toluene of 14.41 parts of itaconic acid monomethyl ester (manufactured by Tokyo Chemical Industry Co., Ltd.) in a container equipped with a stirrer, a condenser, a thermometer, and a dripping funnel in an about 30 minutes while stirring at room temperature followed by dripping of 6.28 parts of aryl amine (manufactured by Tokyo Chemical Industry Co., Ltd.) in about 30 minutes at room temperature thereto followed by a two-hour stirring at room temperature.

Thereafter, conduct reaction for six hours under heating while refluxing.

Next, condense the filtrate in which diisopropyl urine is filtered from the reaction product to about a half by volume followed by silica gel chromatography using toluene as a developing solvent to obtain 15.01 parts of the target compound g-II (N-aryl itaconicimide).

Figure 9A:
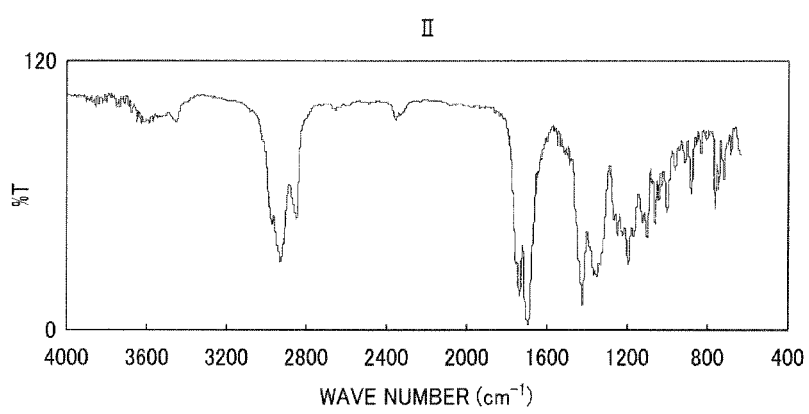
FIG. 9A is a graph illustrating an infrared absorption spectrum of a compound g-II.

The infra-red absorption spectrum graph is shown as FIG. 9A.

Synthesis Example g-III-1

Synthesis of Silicone Compound: 1 is Nearly Equal to 6, m is Nearly Equal to 3, n is Nearly Equal to 3, and Y=phenoxypropyl in the Chemical Structure 6

Drip 0.93 parts of the compound g-II: N-aryl itaconicimide, 0.83 parts of arylphenyl ether (manufactured by Tokyo Chemical Industry Co., Ltd.), 10 parts of toluene, and 0.024 parts of xylene solution of 2% by weight platinum/1,3-divinyl-1,1,3,3-tetramethyl disiloxane complex (manufactured by Sigma-Aldrich Co.) to a solution of 2.0 parts of silicone compound: copolymer of poly(dimethyl siloxane-methylhydroxy siloxane with ends terminated by trimethyl silyl (mol ratio: 50%) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 3.88 parts of the target silicone compound g-M1.

Figure 9B:
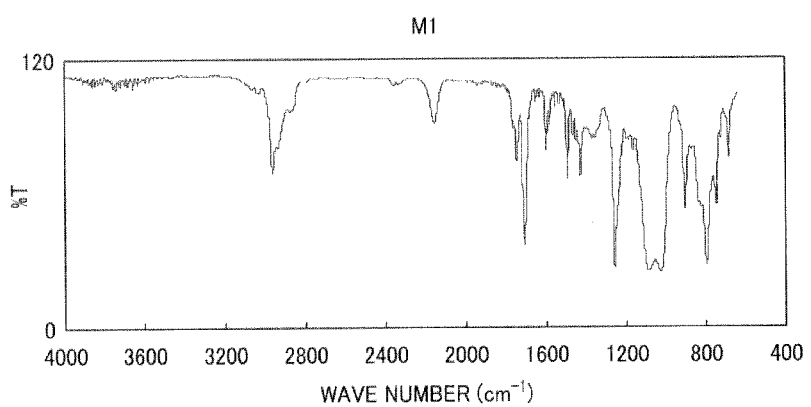
FIG. 9B is a graph illustrating an infrared absorption spectrum of a silicone compound g-M1.

The infra-red absorption spectrum graph is shown as FIG. 9B.

Synthesis Example g-III-2

Synthesis of Silicone Compound: 1 is Nearly Equal to 6, m=n=0, X1=X3=Substituent A-7 in the Chemical Structure 1

Drip 1.04 parts of the compound g-II: N-aryl itaconic imide, 10 parts of toluene, and 0.013 parts of xylene solution of 2% by weight platinum/1,3-divinyl-1,1,3,3-tetramethyl disiloxane complex (manufactured by Sigma-Aldrich Co.) to a solution of 2.0 parts of silicone compound: polydimethyl siloxane with ends terminated by hydride) (molecular weight: Mn=580, manufactured by Sigma-Aldrich Co.) and 2.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 2.14 parts of the target silicone compound g-M2.

Figure 9C:
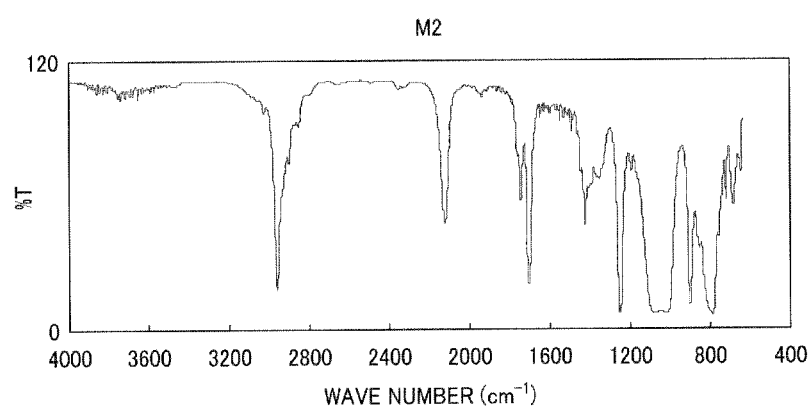
FIG. 9C is a graph illustrating an infrared absorption spectrum of a silicone compound g-M2.

The infra-red absorption spectrum graph is shown as FIG. 9C.

Synthesis Example g-III-3

Synthesis of Silicone Compound: 1=1, m=n=0, and X1=X3=Substituent A-7 in the Chemical Structure 1

Drip 2.18 parts of the compound g-II: N-aryl itaconic imide, 10 parts of toluene, and 0.027 parts of xylene solution of 2% by weight platinum/1,3-divinyl-1,1,3,3-tetramethyl disiloxane complex (manufactured by Sigma-Aldrich Co.) to a solution of 1.5 parts of silicone compound: (1,1,3,3,5,5-hexamethyl trisiloxane (manufactured by Sigma-Aldrich Co) and 1.5 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 $cm^{-1}$ of Si—H in infra-red absorption spectrum to obtain 2.53 parts of the target silicone compound g-M3.

Figure 9D:
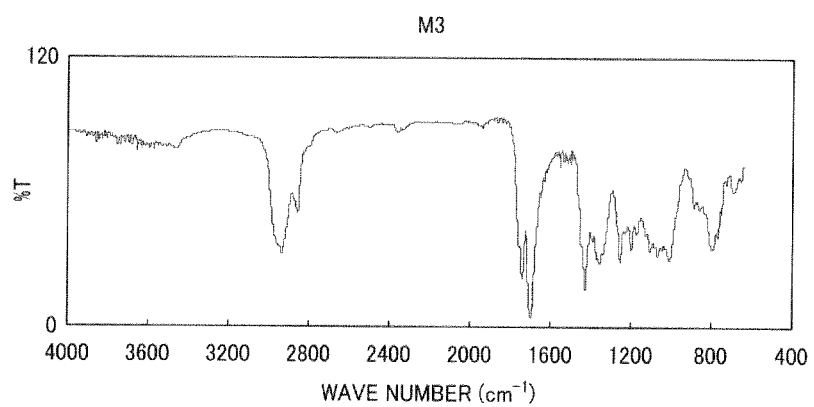
FIG. 9D is a graph illustrating an infrared absorption spectrum of a silicone compound g-M3.

The infra-red absorption spectrum graph is shown as FIG. 9D.

Synthesis Example g-III-4

Synthesis of Silicone Compound: 1=m=n=0, X1=X3=Substituent A-7 in the Chemical Structure 1

Drip 2.25 parts of the compound g-II: N-aryl itaconic imide, 10 parts of toluene, and 0.028 parts of xylene solution of 2% by weight platinum/1,3-divinyl-1,1,3,3-tetramethyl disiloxane complex (manufactured by Sigma-Aldrich Co.) to a solution of 1.0 part of silicone compound: (1,1,3,3-tetramethyl trisiloxane (manufactured by Tokyo Chemical Industry Co., Ltd.) and 1.0 part of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 2.39 parts of the target silicone compound g-M4.

Figure 9E:
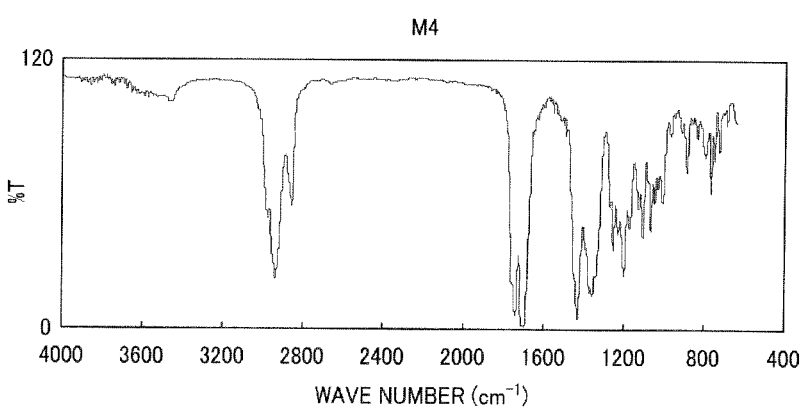
FIG. 9E is a graph illustrating an infrared absorption spectrum of a silicone compound g-M4.

The infra-red absorption spectrum graph is shown as FIG. 9E.

Synthesis Example g-III-5

Synthesis of Silicone Compound: l=n=0, m=1 in the Chemical Structure 6

Drip 2.04 parts of the compound g-II: N-aryl itaconic imide, 10 parts of toluene, and 0.026 parts of xylene solution of 2% by weight platinum/1,3-divinyl-1,1,3,3-tetramethyl disiloxane complex (manufactured by Sigma-Aldrich Co.) to a solution of 3.0 parts of silicone compound: (1,1,1,3,5,5,5-heptamethyl trisiloxane (manufactured by Tokyo Chemical Industry Co., Ltd.) and 3.0 parts of toluene in about 60 minutes while stirring at a room temperature followed by reaction under the same condition one night.

Thereafter, distill away the solvent with a reduced pressure, conduct stripping treatment for two hours with a reduced pressure of 10 mmHg at 40° C. and confirm disappearance of absorption (2155 cm$^{-1}$ of Si—H in infra-red absorption spectrum to obtain 3.37 parts of the target silicone compound g-M5.

Example g-1

Place 1.0 part of the coloring resin particle (α), 18.56 parts of the silicone compound (g-M1), and 0.43 parts of silicone oil compound having an epoxy group (3-glycidoxy propyl (bis trimethylsiloxy)methylsilane)(manufactured by Tokyo Chemical Industry Co., Ltd.), which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink g-1.

The volume average particle diameter of the ink is 0.22 μm and the relative standard deviation (CV value) is 28%.

After the ink is preserved for 20 days, no agglomeration is observed and the volume average particle diameter is still 0.22 μm. That is, the ink has an excellent preservation stability.

Example g-2

Place 1.0 part of the coloring resin particle (α), 18.76 parts of the silicone compound (g-M1), and 0.24 parts of silicone oil compound having an epoxy group (2-ethylhexyl glycidyl ether, manufactured by Tokyo Chemical Industry Co., Ltd.) which is the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink g-2.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example g-3

Place 1.0 part of the coloring resin particle (α), 18.71 parts of the silicone compound (g-M2), and 0.29 parts of silicone oil compound having an epoxy group (2-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink g-3.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example g-4

Place 1.0 part of the coloring resin particle (α), 18.71 parts of the silicone compound (g-M3), and 0.29 parts of silicone oil compound having an epoxy group (3-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink g-4.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Example g-5

Place 1.0 part of the coloring resin particle (α), 18.71 parts of the silicone compound (g-M4), and 0.29 parts of silicone oil compound having an epoxy group (4-ethylhexyl glycidyl ether, manufactured by Tokyo Chemical Industry Co., Ltd.) which is 1.2 times the equivalent to the acid value of the coloring resin particles (α) in a beaker followed by a two-hour dispersion by an ultrasonic dispersion device (output: 130 W, frequency: 20 kHz, pulser system) and add 1.5 parts of 15% by weight of zirconium octylate (manufactured by NIHON KAGAKU SANGYO CO., LTD.) to the liquid dispersion to obtain a photocurable liquid ink g-5.

The volume average particle diameter of the ink is 0.21 μm and the relative standard deviation (CV value) is 28%.

After the ink is preserved for 20 days, no agglomeration is observed and the volume average particle diameter is still 0.21 μm. That is, the ink has an excellent preservation stability.

Inks of Examples g-1 to g-5 are evaluated in the same manner as in Those of Examples a-1 to a-13 by the evaluation tests 1 to 3.

The results are shown in Tables 7-1 to 7-3.

Evaluation Test 1
Evaluation on Photocurability

TABLE 7-1

| | Curing energy (mJ/cm$^2$) |
|---|---|
| Example g-1 (Liquid ink g-1) | 745 |
| Example g-2 (Liquid ink g-2) | 720 |
| Example g-3 (Liquid ink g-3) | 940 |
| Example g-4 (Liquid ink g-4) | 515 |
| Example g-5 (Liquid ink g-5) | 845 |

Evaluation Test 2
Image Evaluation By Electrophotographic Image Forming Apparatus

TABLE 7-2

| | Definition |
|---|---|
| Example g-1 (Liquid ink g-1) | G |
| Example g-2 (Liquid ink g-2) | G |
| Example g-3 (Liquid ink g-3) | G |
| Example g-4 (Liquid ink g-4) | G |
| Example g-5 (Liquid ink g-5) | G |

Evaluation Test 3
Results of Image Evaluation for Inkjet System

TABLE 7-3

| | Definition |
|---|---|
| Example g-1 (Liquid ink g-1) | G |
| Example g-2 (Liquid ink g-2) | G |
| Example g-3 (Liquid ink g-3) | G |
| Example g-4 (Liquid ink g-4) | G |
| Example g-5 (Liquid ink g-5) | G |

What is claimed is:

1. A silicone compound represented by the following Chemical Structure 1:

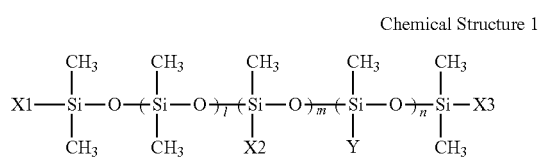

Chemical Structure 1 wherein Y represents a substituted or non-substituted alkyl group having one to ten carbon atoms, X1, X2, and X3 independently represent methyl groups or any of the following Substituents A-2, A-4, A-5 and A-7, at least one of X1, X2, and X3 is any of the Substituents A-2, A-4, A-5 and A-7, and l, m, and n are independently zero or an integer of from 1 to 6,

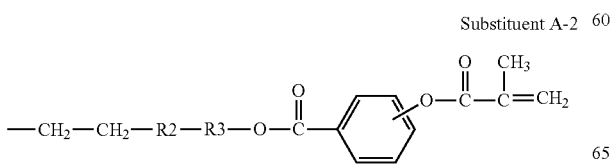

Substituent A-2 wherein R2 represents a single bonding or an alkylene group having one to four carbon atoms and R3 represents a single bonding or an alkyleneoxy group having one to four carbon atoms,

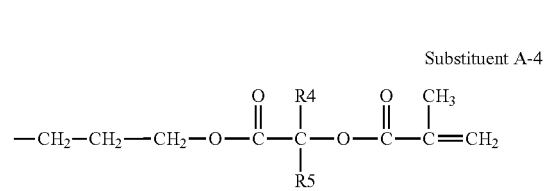

Substituent A-4 wherein R4 and R5 independently represent hydrogen atoms or methyl groups,

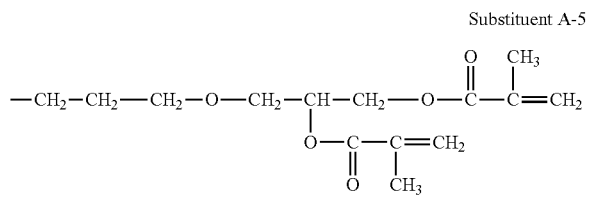

Substituent A-5 and

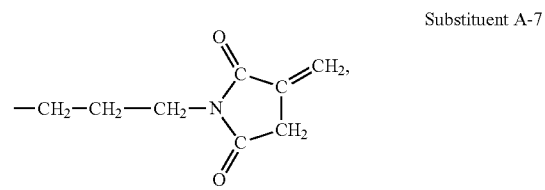

Substituent A-7 and wherein the silicone compound contains at least one of the Substituents A-2, A-4, A-5 and A-7.

2. A silicone compound, satisfying the following Chemical Structure 5:

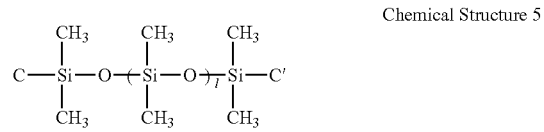

Chemical Structure 5 wherein C' represents the following Substituent C and l presents zero or an integer of from 1 to 6,

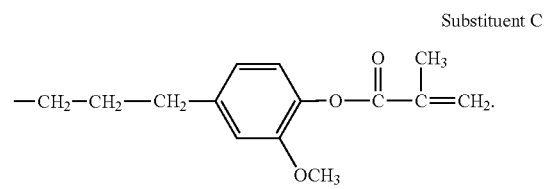 [SMILES: C=C(C)C(=O)Oc1ccc(CCCC)cc1OC]

Substituent C

3. The silicone compound according to claim 1, satisfying the following Chemical Structure 6:

Chemical Structure 6

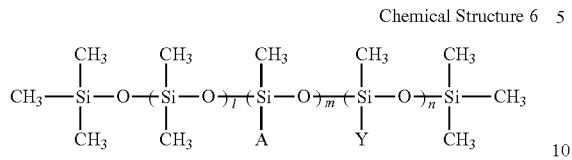

wherein Y represents a substituted or non-substituted alkyl group having one to ten carbon atoms, A represents any of the following Substituents A-4, A-5 and A-7, and l, m, and n are independently zero or an integer of from 1 to 6, Substituent A-4

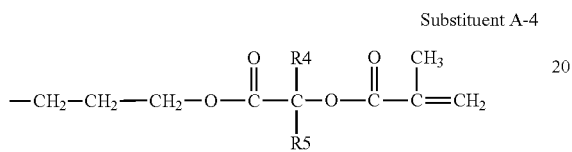

wherein R4 and R5 independently represent hydrogen atoms or methyl groups,

Substituent A-5

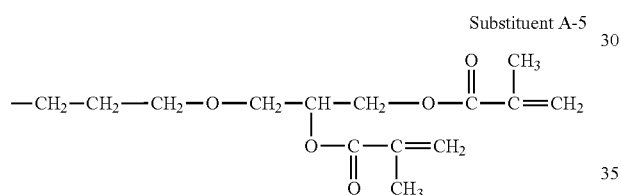

and

Substituent A-7

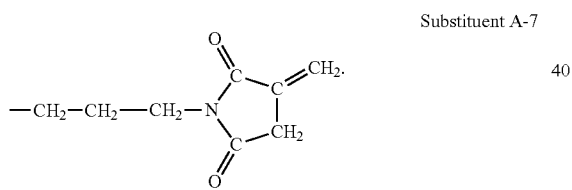

4. A photocurable liquid ink comprising:
a coloring agent; and
a photocurable liquid comprising the silicone compound of claim 1.

5. The photocurable liquid ink according to claim 4, wherein a coloring resin particle having an acid group on a surface thereof which is chemically modified, via the acid group, by at least one of a silicone compound having an epoxy group and a long chain alkyl compound having an epoxy group is used as the coloring agent.

6. A method of manufacturing photocurable liquid ink comprising:
dispersing a coloring resin particle having an acid group on a surface thereof in liquid that contains at least one of a silicone compound having an epoxy group and a long chain alkyl compound having an epoxy group to conduct reaction of the coloring resin particle and the at least one of a silicone compound having an epoxy group and a long chain alkyl compound having an epoxy group to chemically modify the coloring resin particle to obtain a liquid dispersion; and blending a photocurable liquid comprising a silicone compound with the liquid dispersion
wherein the silicone compound is represented by the following Chemical Structure 1:

Chemical Structure 1

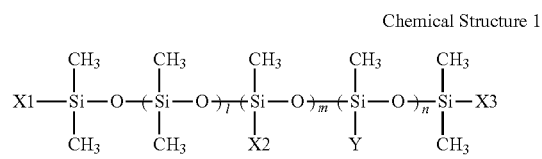

wherein Y represents a substituted or non-substituted alkyl group having one to ten carbon atoms, X1, X2, and X3 independently represent methyl groups or any of the following Substituents A-1 to A-7, at least one of X1, X2, and X3 is any of the Substituents A-1 to A-7, and l, m, and n are independently zero or an integer of from 1 to 6, Substituent A-1

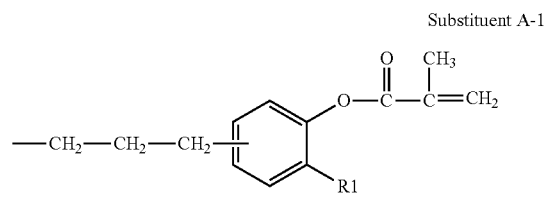

wherein R1 is a hydrogen atom, an alkyl group having one to four carbon atoms, or an alkoxy group having one to four carbon atoms, Substituent A-2

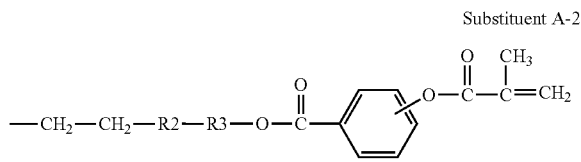

wherein R2 represents a single bonding or an alkylene group having one to four carbon atoms and R3 represents a single bonding or an alkyleneoxy group having one to four carbon atoms, Substituent A-3

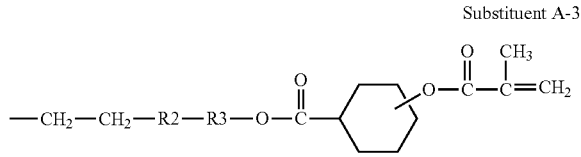

wherein R2 represents a single bonding or an alkylene group having one to four carbon atoms and R3 represents a single bonding or an alkyleneoxy group having one to four carbon atoms, Substituent A-4

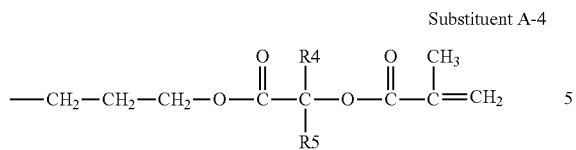

wherein R4 and R5 independently represent hydrogen atoms or methyl groups,

Substituent A-5

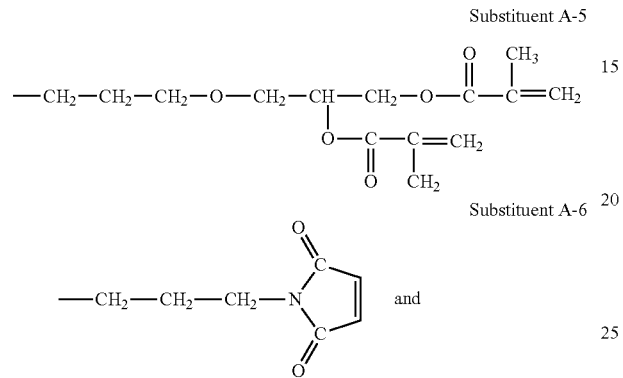

Substituent A-6

Substituent A-7

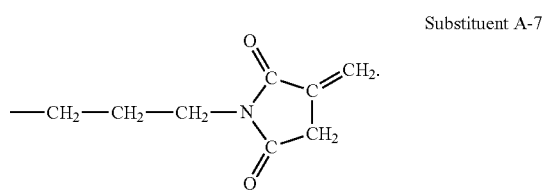

7. The method of manufacturing photocurable liquid ink according to claim 6, wherein the coloring resin particle having an acid group on a surface thereof is manufactured by precipitating a resin having an acid group, which is neutrally-dissolved in an aqueous solution, on a surface of a pigment or dye by a salting-out method using a dispersion body of the resin having an acid group which is neutrally-dissolved in an aqueous solution and the pigment or dye.

* * * * *